(12) United States Patent
Miao et al.

(10) Patent No.: US 11,708,417 B2
(45) Date of Patent: Jul. 25, 2023

(54) MINIATURIZED ANTIBODY OF ANTI-GLUCOCORTICOID-INDUCED TUMOR NECROSIS FACTOR RECEPTOR (GITR), AND POLYMER AND USE THEREOF

(71) Applicant: INNOVENT BIOLOGICS (SUZHOU) CO., LTD., Jiangsu (CN)

(72) Inventors: Xiaoniu Miao, Jiangsu (CN); Zhihui Kuang, Jiangsu (CN); Weifeng Huang, Jiangsu (CN); Junjian Liu, Jiangsu (CN)

(73) Assignee: INNOVENT BIOLOGICS (SUZHOU) CO., LTD, Jiangsu (CN)

( * ) Notice: Subject to any disclaimer, the term of this patent is extended or adjusted under 35 U.S.C. 154(b) by 339 days.

(21) Appl. No.: 16/771,777

(22) PCT Filed: Mar. 26, 2019

(86) PCT No.: PCT/CN2019/079625
§ 371 (c)(1),
(2) Date: Jun. 11, 2020

(87) PCT Pub. No.: WO2019/184898
PCT Pub. Date: Oct. 3, 2019

(65) Prior Publication Data
US 2022/0267458 A1  Aug. 25, 2022

(30) Foreign Application Priority Data
Mar. 26, 2018 (CN) .......................... 201810255332.2

(51) Int. Cl.
| C07K 16/28 | (2006.01) |
| C07K 19/00 | (2006.01) |
| C12N 15/62 | (2006.01) |
| C12N 15/85 | (2006.01) |
| G01N 33/68 | (2006.01) |
| A61K 39/00 | (2006.01) |

(52) U.S. Cl.
CPC .......... *C07K 16/2878* (2013.01); *C07K 19/00* (2013.01); *C12N 15/62* (2013.01); *C12N 15/85* (2013.01); *G01N 33/68* (2013.01); *A61K 2039/505* (2013.01); *C07K 2317/24* (2013.01); *C07K 2317/31* (2013.01); *C07K 2317/569* (2013.01); *C07K 2317/622* (2013.01); *C07K 2317/92* (2013.01)

(58) Field of Classification Search
CPC ................ C07K 16/2878; C07K 19/00; C07K 2317/24; C07K 2317/31; C07K 2317/569; C07K 2317/622; C07K 2317/92; C07K 16/2818; C07K 2317/22; C07K 2317/35; C07K 2317/732; C07K 2317/75; C07K 2317/94; C07K 2317/56; C07K 2319/00; C12N 15/62; C12N 15/85; G01N 33/68; G01N 2333/715; G01N 33/6863; G01N 33/6872; A61K 2039/505; A61K 2039/507; A61K 2039/54; A61K 2039/545; A61P 35/00
See application file for complete search history.

(56) References Cited

FOREIGN PATENT DOCUMENTS

| CN | 103951753 A | 7/2014 |
| CN | 106459203 A | 2/2017 |
| WO | 2015/031667 A2 | 3/2015 |
| WO | 2016/196792 A1 | 12/2016 |
| WO | WO-2017068186 A1 * | 4/2017 .............. A61P 31/04 |
| WO | 2017/068186 A9 | 6/2017 |

OTHER PUBLICATIONS

Nocentini et al: "GITR: a multifaceted regulator of immunity belonging to the tumor necrosis factor receptor superfamily", Eur. J. Immunol., 2005, 35: 1016-1022.
Nocentini et al: "GITR/GITRL: More than an effector T cell co-stimulatory system", Eur. J Immunol. 2007, 37: 1165-1169.
International Search Report and Written Opinion of PCT/CN2019/079625, dated Jul. 2, 2019.

* cited by examiner

Primary Examiner — Hong Sang
Assistant Examiner — Sung Min Yoon
(74) Attorney, Agent, or Firm — Leason Ellis LLP

(57) ABSTRACT

An antibody that specifically binds to a glucocorticoid-induced tumor necrosis factor receptor (GITR), an antibody fragment and a polymer thereof, and a conjugate and a fusion comprising the antibody or the antibody fragment are provided in the present invention. A nucleic acid encoding the antibody, the antibody fragment, the polymer, the conjugate and the fusion, a vector, and a host cell expressing the nucleic acid are also provided in the present invention. In addition, a composition comprising the antibody and the antibody fragment thereof, the polymer, the conjugate or the fusion, and use thereof in therapy and diagnosis are also provided in the present invention.

25 Claims, 10 Drawing Sheets
Specification includes a Sequence Listing.

MINIATURIZED ANTIBODY OF ANTI-GLUCOCORTICOID-INDUCED TUMOR NECROSIS FACTOR RECEPTOR (GITR), AND POLYMER AND USE THEREOF

CROSS REFERENCE TO RELATED APPLICATIONS

This application is a 371 national stage of International Application No. PCT/CN2019/079625 filed on Mar. 26, 2019, which claims priority of Chinese Patent Application No. 201810255332.2 filed on Mar. 26, 2018, the disclosure of each of which is hereby incorporated by reference in its entirety as part of this application.

INCORPORATION-BY-REFERENCE OF SEQUENCE LISTING

A sequence listing, filed as the ASCII text file "11275-008742-USO_ST25" which was created on Jun. 10, 2021 and is 107 kb in size, is incorporated herein by reference in its entirety.

TECHNICAL FIELD

The present invention relates to the field of antibody. The present invention particularly relates to an antibody (including a miniaturized antibody) that specifically binds to a glucocorticoid-induced tumor necrosis factor receptor (GITR), an antibody fragment thereof and a polymer thereof, and a conjugate and a fusion comprising the antibody or the antibody fragment. The present invention further relates to a nucleic acid encoding the antibodies, the antibody fragments, the polymers, the conjugates and the fusions, and a vector and a host cell expressing the nucleic acid. The present invention also relates to a product comprising the antibodies and the antibody fragments thereof, the polymers, the immunoconjugate or the fusion, and a use of the product in treatment and diagnosis.

BACKGROUND

Glucocorticoid-induced tumor necrosis factor receptor (GITR), also known as TNFRSF18, activation-inducible tumor necrosis factor receptor family member (AITR), CD357 and GITR-D, is the 18th member of the tumor necrosis factor receptor (TNFR) superfamily A GITR is activated by homologous ligand thereof, GITR ligand (GITRL), which can bind to an NF-κB dimer and activate the downstream NF-κB signaling pathway.

A GITR is expressed at low levels on resting responder T cells and is up-regulated on activated T cells. A GITR is expressed constitutively at high levels on regulatory T cells (Treg, e.g., CD4$^+$CD25$^+$ or CD8$^+$CD25$^+$ cells) and is further up-regulated when the cells are activated (Nocentini and Riccardi (2005) E. J. Immunol. 35:1016-1022). A GITR is expressed not only on T cells, but also, as reported, on NK cells, macrophages, B cells, dendritic cells, mast cells and monocytes (Nocentini and Riccardi (2005) E. J. Immunol. 35:1016-1022).

GITR ligands (GITRLs) are mainly expressed on antigen-presenting cells (APCs), including macrophages, B cells, dendritic cells, and endothelial cells. Binding of a GITRL on an APC to a GITR on a responder T cell triggers GITR signaling, which co-stimulates responder T cells and inhibits the inhibitory activity of Treg cells. Therefore, a GITR has several effects on effector T cells and regulatory T cells, including: co-stimulation and activation of effector T cells to make T cells more resistant to inhibition, inhibition of regulatory T cells, reduction of the sensitivity of effector T cells to the suppression induced by regulatory T cells, etc. (Nocentini, et al. (2007) Eur. J. Immunol. 37:1165-1169).

These effects suggest that the activation of GITRs can lead to an enhanced immune response and an increased resistance to tumors and viral infections. Therefore, substances capable of activating GITRs can enhance the required immune responses (e.g., antitumous effect and treatment of viral infections), induce or enhance immune responses in individuals, and treat immune disorders and proliferative disorders (e.g., tumors and cancers), etc.

Currently, substances capable of activating GITRs in the prior art mainly include anti-GITR antibodies having a standard structure (see CN103951753A, CN105829343A, CN106459203A, WO2016196792A1, WO2017068186A9, etc.). Such antibodies are GITR agonists (i.e., activated antibodies), which can induce or enhance GITR signaling, and are effective in the treatment of a variety of GITR-related diseases or conditions that require an enhanced immune response. Since such anti-GITR antibodies are activated antibodies, in terms of exerting its activity, e.g., activity of immunological enhancement, the level of activation activity is a more critical index than the binding affinity to antigens.

However, the above-mentioned anti-GITR antibodies having a standard structure have some inherent defects: high production cost, long preparation period, complicated preparation process, large volume (poor tissue permeability), poor stability, large differences between different batches, etc., which greatly limit the scope of use thereof.

Besides, miniaturized antibodies including single-chain variable fragments (scFvs), single-domain antibodies (sdAds), heavy-chain antibodies (hcAbs), nanobodies (Nbs) (or variable domains of heavy chains of heavy-chain antibodies (VHHs)) and small antibody-like scaffold proteins (e.g., Affibody, DARPins, etc.) have, in the field of biotechnology application, attracted extensive attention on the research and development due to overcoming some inherent defects of the antibodies having a standard structure, and have gained rapid development in recent years.

Among the miniaturized antibodies, single-domain antibodies and heavy-chain antibodies, which have no light chain and have a single heavy chain variable region retaining the intact antigen binding activity, are characterized by small molecules, high stability, good permeability to in vivo tissues, good solubility, high melting temperature and easy expression.

For example, among the miniaturized antibodies, nanobodies have the advantages described below:

1. The unique structure of nanobodies leads to beneficial antigen binding properties, i.e., the long CDR3 (complementarity determining region 3) of nanobodies is able to form a stable, exposed convex ring structure, which has a structure-stabilizing disulfide bond inside, to penetrate deeper into antigens, thus better binding to the antigens and improving the specificity for and binding affinity to the antigens, while antigen binding surfaces of Fab fragments of traditional antibodies and single-chain variable fragments (scFvs) often form concave topologies, usually resulting in the recognition of only sites on antigen surfaces. Therefore, nanobodies have more beneficial antigen binding properties, and, even when antigen proteins are so tightly wrapped as to hide epitopes unrecognizable by ordinary antibodies, are still able to recognize such epitopes.

2. When VH domains of an antibody having a standard structure are expressed alone, the expressed VH domains usually form an inclusion body, or the exposed hydrophobic domains adhere to each other. In contract, because hydrophobic residues in the FR2 region are replaced by hydrophilic residues, nanobodies have excellent solubility and less aggregation, and can be easily condensed to 10 mg/mL in ordinary buffers without accumulation. Moreover, due to the reversible refolding ability, namely nanobodies can still maintain the antigen binding activity under the action of high temperature (80-92° C.) and high concentration of denatured agents, and have the strong ability of renaturation even when expressed in the form of an inclusion body, nanobodies are able to, in a transient denaturation during chromatography or aseptic treatment, or in adverse environments such as contamination or organic solvents, well maintain the bioactivity over a long period of time, which greatly improves the utilization rate of nanobodies as drugs.

3. Because of the small molecular weight, the simple structure and the coding by a single gene, nanobodies are easily synthesized in microorganisms and can be expressed in large quantities in inexpensive bacteriophages, yeasts and other microorganisms for mass production. It has been reported that the yield of nanobodies can be increased to 1 g/L by a yeast reactor.

Meanwhile, since nanobodies have only one heavy chain variable region, which does not require pairing, the screening process is simpler and often requires a library only.

4. Because of small molecules and strong tissue permeability, nanobodies are able to penetrate or transfer into blood-brain barriers, and are also able to be quickly filtered by kidneys (the renal retention value is about 60 kDa). Besides, nanobodies have a half-life of about 2 hours in blood, as well as a unique epitope target, and are therefore an excellent therapeutic vector.

5. Compared with sdAbs, scFvs, etc., nanobodies also have the following outstanding advantages: simple structure, strong ability in binding to a receptor, ability to recognize hidden antigenic epitopes embedded in ligand grooves or sandwiched between two subunits, lower relative molecular weight, lower immunogenicity, lower tendency of accumulation and precipitation, better biological dispersibility, easier expression (high expression in a prokaryotic or eukaryotic system), better solubility, higher stability, better stability in adverse physical and chemical environments such as extreme pH, high concentration of denaturants or high temperature, long shelf life, and oral or respiratory administration. Besides, nanobodies do not tend to adhere to each other and even aggregate as single-chain variable fragments (scFvs) do.

Detection kits made of nanobodies can even be stored directly at room temperature without refrigeration, which saves a lot on refrigeration.

Based on the functions and advantages of the above-mentioned substances capable of activating GITRs, there is a need in the art to prepare miniaturized antibodies capable of activating GITRs, such as nanobodies capable of activating GITRs, in order to better induce or enhance immune responses in individuals and treat immune disorders and proliferative disorders (such as tumor and cancer).

SUMMARY OF THE INVENTION

As mentioned above, the anti-GITR antibodies having a standard structure have such disadvantages as complex screening process, poor tissue permeability and high production cost, so the development of anti-GITR miniaturized antibodies can well make up for these shortcomings, produce many other advantages, and achieve the performance of anti-GITR antibodies.

However, obtaining corresponding VHHs is not accomplished by simply separating heavy chain variable regions of the known antibodies having a standard structure, because, as mentioned above, the amino acid sequence and length of CDRs 1-3 in a VHH, especially the amino acid selection and length of the CDR3, are different from the same of the corresponding HCDRs 1-3, e.g., the HCDR3, in an antibody having a standard structure, so is the structure, which requires a careful design and a lot of screening to be done.

The object of the present invention is to provide an isolated antibody that specifically binds to a glucocorticoid-induced tumor necrosis factor receptor (GITR) or an antigen binding fragment thereof (referred to as "the antibody or the antigen-binding fragment thereof disclosed herein"), which has one or more of the following characteristics:

(i) binding, with high binding affinity, to human GITRs (such as a polypeptide of SEQ ID NO: 123 or 127);
(ii) binding, with a low dissociation constant, to human GITRs (such as a polypeptide of SEQ ID NO: 123 or 127);
(iii) binding, with high binding affinity, to antigens on cell surfaces;
(iv) efficiently activating the NF-KB signaling pathway downstream of a GITR;
(v) cross-competed with GITRLs for binding to GITRs;
(vi) being able to be internalized into human CD4 cells;
(vii) inhibiting the inhibitory effect of regulatory T cells;
(viii) activating effector T cells;
(ix) reducing circulating regulatory T cells;
(x) being able to bind to Fcγ receptors (FcγR); and
(xi) having a half-life of at least 6, 7, 9, or 12 days in human serum.

Another object of the present invention is to provide a nanobody (referred to as "the nanobody disclosed herein"), the HCDR3 (heavy chain complementarity determining region 3) in which comprises the HCDR3 of the antibody or the antigen binding fragment thereof disclosed herein.

In some embodiments, the HCDR1 (heavy chain complementarity determining region 1) and the HCDR2 (heavy chain complementarity determining region 2) of the nanobody disclosed herein respectively comprise the HCDR1 and the HCDR2 of the antibody or the antigen binding fragment thereof disclosed herein.

In some embodiments, the HCDR1, the HCDR2, and the HCDR3 of the nanobody disclosed herein respectively comprise the HCDR1, the HCDR2, and the HCDR3 of the antibody or the antigen binding fragment thereof disclosed herein.

In some embodiments, the nanobody disclosed herein comprises only the heavy chain variable region sequence set forth in any one of SEQ ID NOs: 64-85 or a variant thereof, or the nanobody disclosed herein consists of only the heavy chain variable region sequence set forth in any one of SEQ ID NOs: 64-85 or a variant thereof.

Another object of the present invention is to provide a heavy-chain antibody (referred to as "the heavy-chain antibody disclosed herein") comprising an Fc fragment of the nanobody disclosed herein and an IgG antibody.

Another object of the present invention is to provide a humanized heavy-chain antibody (referred to as "the humanized heavy-chain antibody disclosed herein") which is modified from the heavy-chain antibody disclosed herein.

In some embodiments, the humanized heavy-chain antibody disclosed herein is a fully humanized heavy-chain antibody.

Another object of the present invention is to provide an antibody in a polymeric form (referred to as "the antibody in a polymeric form disclosed herein"), which is a polymeric form of the nanobody disclosed herein, a heavy chain variable region of the heavy-chain antibody disclosed herein, or a heavy chain variable region of the humanized heavy-chain antibody disclosed herein.

In some embodiments, the antibody in a polymeric form disclosed herein is a tetrameric or hexameric form of the nanobody disclosed herein, a heavy chain variable region of the heavy-chain antibody disclosed herein, or a heavy chain variable region of the humanized heavy-chain antibody disclosed herein, preferably, a tetrameric form of the nanobody disclosed herein, a heavy chain variable region of the heavy-chain antibody disclosed herein, or a heavy chain variable region of the humanized heavy-chain antibody disclosed herein.

In some embodiments, the antibody in a polymeric form disclosed herein is polymerized from new structures formed by linking the nanobody disclosed herein, a heavy chain variable region of the heavy-chain antibody disclosed herein, or a heavy chain variable region of the humanized heavy-chain antibody disclosed herein to the heavy-chain antibody disclosed herein, preferably, the humanized heavy-chain antibody disclosed herein.

In some embodiments, the antibody in a polymeric form disclosed herein is polymerized from new structures formed by linking the nanobody disclosed herein, a heavy chain variable region of the heavy-chain antibody disclosed herein, or a heavy chain variable region of the humanized heavy-chain antibody disclosed herein to the C-terminus of the heavy-chain antibody disclosed herein; or polymerized from new structures formed by linking the nanobody disclosed herein, a heavy chain variable region of the heavy-chain antibody disclosed herein, or a heavy chain variable region of the humanized heavy-chain antibody disclosed herein to the N-terminus of the heavy-chain antibody disclosed herein, preferably, the humanized heavy-chain antibody disclosed herein.

In some embodiments, in the antibody in a polymeric form disclosed herein, the nanobody disclosed herein, a heavy chain variable region of the heavy-chain antibody disclosed herein, or a heavy chain variable region of the humanized heavy-chain antibody disclosed herein is linked to the heavy-chain antibody disclosed herein, preferably the humanized heavy-chain antibody disclosed herein, via a linker peptide.

Another object of the present invention is to provide a fusion protein, an immunoconjugate, a composition or a kit comprising the antibody disclosed herein.

Another object of the present invention is to provide an isolated nucleic acid encoding the antibody disclosed herein; a vector comprising the nucleic acid; a host cell comprising the vector; and a pharmaceutical composition comprising one or more of the nucleic acid, the vector and the host cell.

Another object of the present invention is to provide a method for preparing the antibody or the antigen binding fragment disclosed herein, the fusion protein disclosed herein, the immunoconjugate or the composition (including the pharmaceutical composition) disclosed herein.

Another object of the present invention is to provide a method for detecting the presence of GITRs in a sample, comprising using the antibody or the antigen binding fragment thereof disclosed herein.

Another object of the present invention is to provide a method for treating cancer, inducing or enhancing immune responses in individuals, and/or stimulating an antigen-specific T cell response, wherein the method comprises administering to the individuals an effective amount of the antibody or the antibody binding fragment thereof disclosed herein, the fusion protein disclosed herein or the immunoconjugate disclosed herein.

Compared with the anti-GITR antibody having a standard structure of the prior art, the antibody disclosed herein has advantages of simple screening process, good tissue permeability and low production cost and the like, and compared with single-chain variable fragments, single-domain antibodies, and heavy-chain antibodies and the like directly obtained from the anti-GITR antibody having a standard structure, the antibody disclosed herein gets rid of disadvantage of easily forming an inclusion body or easily adhering to each other. Further, the inventors of the present invention have surprisingly found that the antibody disclosed herein is highly specific for GITRs without interfering with the activity of other receptors, and is able to stimulate GITR signaling at a relatively low dose. In addition, the antibody disclosed herein is able to efficiently activate the NF-κB signaling pathway downstream of a GITR, thus producing beneficial effects against immune diseases/disorders and proliferative diseases/disorders.

The present invention is further illustrated in the following drawings and specific embodiments. However, these drawings and specific embodiments should not be constructed as limiting the scope of the present invention, and changes easily conceived by those skilled in the art will be included in the spirit of the present invention and the protection scope of the appended claims.

DETAILED DESCRIPTION

Figure 1:
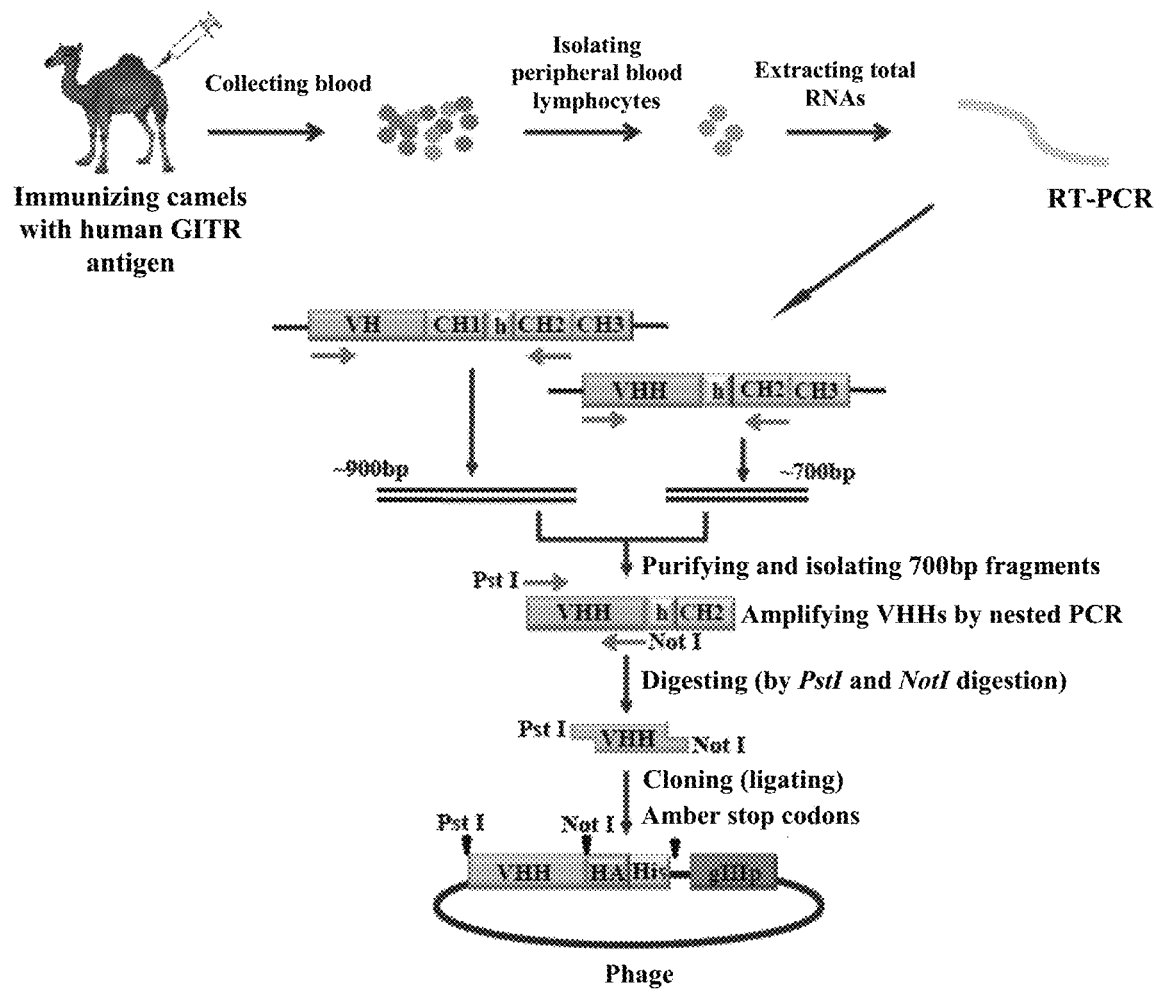
FIG. 1 is a flow diagram of construction of a nanobody phage library.

The present invention will be described in detail below in conjunction with examples. All experimental reagents, instruments and equipments used are, unless otherwise specified, ordinary commercially available reagents, instruments and equipments.

1. Definition

Unless otherwise defined herein, all terms used herein have the meaning commonly understood by those of ordinary skill in the art. Furthermore, unless otherwise required by context, terms used herein in the singular shall be deemed to include the plural and vice versa. For a better explanation and understanding of the present invention, some terms used herein are specifically defined below.

As used herein, the term "about", when used in combination with a numerical value, is intended to cover a numerical value within a range of 5% less than the specified numerical value and 5% greater than the specified numerical value.

As used herein, the term "and/or" means any one or two of the options.

As used herein, the term "comprise" or "include" is intended to mean that the described elements, integers or steps are included, but not to the exclusion of any other elements, integers or steps. The term "comprise" or "include" used herein, unless otherwise specified, also encompasses the situation where the entirety consists of the described elements, integers or steps. For example, when referring to "comprise" an antibody variable region of a particular sequence, it is also intended to encompass an antibody variable region consisting of the particular sequence.

As used herein, the term "GITR" refers to "glucocorticoid-induced TNF-related gene and/or polypeptide" and is also known in the art as "TNF receptor superfamily 18 (TNFRSF18)" Amino acid and nucleic acid sequences of human and murine GITRs are described in WO98/06842, which are incorporated herein by reference. See also GenBank accession numbers Q9Y5U5 (human amino acid sequence) and AF109216 (murine nucleic acid and amino acid sequences). The amino acid sequence of a specific mature human GITR polypeptide is set forth in SEQ ID NO: 123. The term GITR as used herein also comprises naturally occurring alleles or variants of the GITR.

The terms "antigen binding molecule", "antigen binding protein" and "antibody" are used interchangeably herein, and all refer to a molecule comprising an antigen binding region or antigen binding portion capable of binding to a target antigen, such as a protein or a peptide. In the present invention, when the target antigen is a glucocorticoid-induced tumor necrosis factor receptor (GITR), the antigen binding molecule that binds to a GITR is also called a GITR binding molecule, a GITR antibody, or an anti-GITR antibody. The antigen binding molecule comprises, for example, an antibody and an antigen binding fragment thereof, a single-chain variable fragment (scFv), a single-domain antibody (sdAd), a heavy-chain antibody (hcAb) and a nanobody (Nb or VHH); or a polymeric form of the antibodies, a variety of fusions and conjugates based on the antibodies, immunoconjugates, antibody-drug conjugates (ADCs), multi-specific/bispecific antibodies, chimeric antigen receptors (CARs), etc. As known to those skilled in the art, the antigen binding portion of an antibody generally comprises amino acid residues from a "complementarily determining region" or a "CDR". Therefore, in the present invention, the term "GITR-binding molecule" may be used interchangeably with any one of "the antibody disclosed herein", "GITR antibody" or "anti-GITR antibody".

As used herein, the term "antibody" refers to a polypeptide (immunoglobulin) comprising at least an immunoglobulin light chain or heavy chain variable region that specifically recognizes and binds to an antigen. The term covers a variety of antibody structures, including, but not limited to, monoclonal antibodies; multi-specific antibodies; Fab fragments, Fab' fragments, F(ab')$_2$ fragments or Fv fragments; diabodies, single-chain variable fragments (scFvs), single-domain antibodies (sdAds), heavy-chain antibodies (hcAbs), nanobodies (Nbs or VHHs) or polymeric forms of the antibodies; human antibodies, humanized antibodies or chimeric antibodies; or labeled antibodies, as long as the desired antigen binding activity is present.

The terms "whole antibody", "full-length antibody", "complete antibody" and "intact antibody" are used interchangeably herein, and all refer to an antibody generally having a structure similar to the structure of a natural antibody and comprising at least two heavy chains (H) and two light chains (L). Each heavy chain consists of a heavy chain variable region (abbreviated herein as VH) and a heavy chain constant region (abbreviated herein as CH). The heavy chain constant region consists of 3 domains, CH1, CH2 and CH3. Each light chain consists of a light chain variable region (abbreviated herein as VL) and a light chain constant region (abbreviated herein as CL). The light chain constant region consists of a domain CL. The constant regions are not directly involved in binding of antibodies to antigens, but exhibit a variety of effector functions.

The terms "variable region (V region, Fv)" and "variable domain" are used interchangeably herein, and all refer to a domain of a heavy or light chain of an antibody that is involved in binding of an antibody to an antigen. Heavy chain variable domains (VHs) and light chain variable domains (VLs) of natural antibodies often have similar structures, wherein each domain comprises four conserved framework regions (FRs) and three complementarity determining regions (CDRs, See, for example, Kindt et al. *Kuby Immunology*, 6th edition, W. H. Freeman and Co., page 91 (2007)). A single VH or VL can be sufficient to provide antigen binding specificity. A light chain variable region and a heavy chain variable region generally comprise domains FR1, CDR1, FR2, CDR2, FR3, CDR3, and FR4 from the N-terminus to the C-terminus.

In a given VH or VL amino acid sequence, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) *Nature* 342:877-883; Al-Lazikani et al., "Standard conformations for the canonical structures of immunoglobulins", *Journal of Molecular Biology*, 273:927-948 (1997)), Kabat based on antibody sequence variability (Kabat et al., *Sequences of Proteins of Immunological Interest*, 4th edition, U.S. Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures. The exact boundary of CDRs of the antibody disclosed herein can be determined according to any scheme in the art or a combination thereof, and according to human evaluation.

A light chain of an antibody can be divided into two types, kappa (κ) and lambda (λ), based on the amino acid sequence of a constant domain thereof. A heavy chain of an antibody can be divided into 5 major types, i.e. IgA, IgD, IgE, IgG, and IgM, depending on the amino acid sequence of a heavy chain constant region thereof, several types of which can be further divided into subtypes, e.g., IgG1, IgG2, IgG3, IgG4, IgA1 and IgA2. Heavy chain constant regions corresponding to different antibody types are called α, δ, ε, γ, and μ, respectively. See, e.g., *Fundamental Immunology*, Ch. 7 (Paul, W. (editor), 2nd edition, Raven Press, N.Y. (1989)) which is incorporated herein by reference in its entirety for all purposes.

The terms "antibody fragment" and "antigen-binding fragment (of antibody)" are used interchangeably herein, both referring to an incomplete antibody molecule that comprises a portion of an intact antibody for binding to an antigen to which the intact antibody binds, and can bind to the antigen and compete with the intact antibody (i.e., with the intact antibody from which the antigen binding fragment is derived) for binding to the antigen. An antigen-binding fragment may be prepared by recombinant DNA techniques, or by enzymatic or chemical cleavage of an intact antibody. The antigen-binding fragment includes, but is not limited to, an Fab, an scFab, an Fab', an F(ab')2, an Fab'-SH, an Fragment of variable (Fv), a single-chain Fv, a diabody, a triabody, a tetrabody, a minibody, a single-domain antibody (sdAb), and a multispecific antibody formed from the antibody fragments. An Fab fragment is a monovalent fragment comprising VL, VH, CL, and CH1 domains, and can be obtained, for example, by papain digestion of an intact antibody. The light chain (L chain) and heavy chain (H chain) of the Fab may be fused into a single polypeptide chain, i.e., a single-chain Fab (scFab), by means of a linker (see e.g., U.S. 20070274985A1). An F(ab')$_2$, a dimer of Fab', is a bivalent antibody fragment, and can be produced by digesting a portion below disulfide bonds in a hinge region of an intact antibody using pepsin. The F(ab')$_2$ may be reduced to Fab' monomers by disrupting the disulfide bonds of the hinge region under neutral conditions. The Fab' monomer is substantially an Fab fragment with a hinge region. The Fv fragment comprises the VL and VH domains of a single arm of an antibody.

As used herein, the term "diabody" refers to an antibody fragment with two antigen antibody-binding sites, which comprises one VL and one VH connected by a short linker in each polypeptide chain. In the diabody, due to the short linker, the two domains VH and VL on one chain cannot pair with each other, but are forced to pair with the complementarity domain on the other chain, thus forming two antigen-binding sites. A diabody may be bivalent or bispecific. More detailed descriptions of the diabody may be found, e.g., in EP 404,097; WO 1993/01161; Hudson et al., *Nat. Med.* 9:129-134 (2003); and Hollinger et al., *PNAS USA* 90:6444-6448 (1993).

Triabodies, tetrabodies and minibodies are also described in Hudson et al., *Nat. Med.* 9:129-134(2003), and Shao Rongguang et al. (eds.), *Antibody Drug Research and Application*, People's Medical Publishing House (2013).

As used herein, the term "single-chain variable fragment (scFv)", or "single-chain variable region", refers to a single polypeptide chain comprising a heavy chain variable region and a light chain variable region connected by a (flexible) linker or (flexible) linker peptide. For example, the genes respectively encoding VL and VH of Fv fragment may be linked by a nucleic acid sequence encoding a linker peptide (linker) through recombinant techniques. The single polypeptide chain forms an antigen-binding site. The single-chain variable fragments are described in detail in International Patent Application Publication No. WO88/01649 and U.S. Pat. Nos. 4,946,778 and 5,260,203.

The terms "(flexible) linker" and "(flexible) linker peptide" are used interchangeably herein, and refer to short peptides (peptide linkers) consisting of amino acids. Various variable domains, such as VH and VL regions, in antibodies disclosed herein may be linked by such peptide linkers. Peptide linkers are typically rich in glycine, which contributes to flexibility, and in serine/threonine, which contributes to solubility. For example, glycine and/or serine residues may be used alone or in combination. Non-limiting examples of the flexible linker peptides or peptide linkers are disclosed in Shen et al., *Anal. Chem.* 80 (6):1910-1917 (2008), WO 2012/138475 and WO 2014/087010, which are incorporated by reference in their entirety. As is known in the art, in construction of an scFv, the linker facilitates VH/VL pairing without interfering with the formation of a functionally effective antigen-binding site from the VH and VL pair.

As used herein, the term "single-domain antibody (sdAb)" refers to an antibody that comprises only one variable domain (e.g., a heavy chain variable domain (VH) or a light chain variable domain (VL)), but can bind to and recognize a target antigen with no interaction with the other variable domain. A single-domain antibody may be derived from a heavy chain variable domain of a camelid heavy chain antibody, a VH-like single domain (v-NAR) of fish IgNAR, and the like.

As used herein, the term "nanobody (Nb, or variable domain of heavy chain of heavy-chain antibody (VHH))" refers to an antibody comprising only one heavy chain variable region, and having an activity of binding to an antigen, i.e., an antibody comprising only one chain of FR4-VCDR3-FR3-VCDR2-FR2-VCDR1-FR1 from C-terminus to N-terminus, which may be produced naturally in camels or by genetic engineering techniques. Nanobody is the minimal unit known to bind target antigens.

As used herein, the term "heavy-chain antibody (hcAb)" refers to an antibody without a light chain, which may comprise VH-CH2-CH3 or VH-CH1-CH2-CH3 from N-terminus to C-terminus, and a homodimer thereof, such as a heavy-chain antibody dimer without light chains. The heavy-chain antibody disclosed herein may comprise a VH from a standard antibody or a VH from a miniaturized antibody. For example, the VH in the heavy-chain antibody disclosed herein may be a nanobody.

As used herein, the term "monoclonal antibody" refers to an antibody obtained from a substantially homogeneous population of antibodies, i.e., the antibodies constituting the population are identical and/or bind to the same epitope except for variant antibodies that are typically present in minor amounts (e.g., variant antibodies containing natural mutations or produced during the production of a monoclonal antibody preparation). Monoclonal antibodies may be prepared by a variety of techniques including, but not limited to, hybridoma, DNA recombination, yeast display, and methods using transgenic animals comprising all or part of human immunoglobulin loci.

The terms "human antibody" and "fully humanized antibody" are used interchangeably herein and refer to an antibody comprising variable regions in which both framework regions and CDR regions are derived from human germline immunoglobulin sequences. Furthermore, if the antibody comprises constant regions, the constant regions are also derived from human germline immunoglobulin sequences. The human antibody disclosed herein may comprise amino acid sequences (e.g., mutations introduced by in-vitro random or site-directed mutagenesis or in-vivo somatic mutation) not encoded by human germline immunoglobulin genes, for example, in CDRs, particularly in CDR3. However, the term "human antibody" is not intended to include antibodies in which CDR sequences derived from the germline of other mammalian species (e.g., mice) are grafted into human framework sequences.

As used herein, the term "humanized antibody" refers to an antibody in which CDR sequences derived from another mammalian species, such as mice, are linked to human framework sequences. Additional framework region modifications may be introduced in human framework sequences.

As used herein, the term "chimeric antibody" refers to an antibody in which the variable region sequences are derived from one species and the constant region sequences are derived from another species, e.g., an antibody in which the variable region sequences are derived from a mouse antibody and the constant region sequences are derived from a human antibody.

As used herein, the term "isolated" antibody is such an antibody that has been separated from components of its natural environment. In some embodiments, the antibody is purified to a purity greater than 95% or 99% as determined by, e.g., electrophoresis (e.g., SDS-PAGE, isoelectric focusing (IEF), and capillary electrophoresis) or chromatography (e.g., ion exchange or reversed phase HPLC). For a review of methods for assessing antibody purity, see, e.g., Flatman et al., J. Chromatogr., B848: 79-87 (2007).

As used herein, the term "epitope" refers to an antigen region to which an antibody binds. Epitopes may be formed by contiguous amino acids or noncontiguous amino acids juxtaposed due to tertiary folding of a protein.

As used herein, the term "specifically bind to" means that an antibody selectively or preferentially binds to an antigen. When an anti-GITR antibody does not substantially bind to non-GITR molecules, the antibody is considered to "specifically bind to" a GITR. However, antibodies specifically binding to a GITR may interact with GITR peptides derived from different species. If an antibody binds to a human GITR with a $K_D$ of about $5\times10^{-7}$ M or less, about $1\times10^{-7}$ M or less, about $5\times10^{-8}$ M or less, about $1\times10^{-8}$ M or less, and about $5\times10^{-9}$ M or less measured by biological optical interferometry, it is an antibody that "specifically binds to human GITR".

As used herein, the terms "affinity" or "binding affinity" refers to an inherent binding capacity that reflects interactions between the partners. Affinity of a molecule X for its partner Y may be generally represented by dissociation constant ($K_D$), which is the ratio of dissociation rate constant ($k_{dis}$) to association rate constant ($k_{on}$). Affinity may be measured by common methods known in the art. One specific method for measuring affinity is the ForteBio kinetic binding assay described herein.

The "antibody that competes for binding" is an antibody that blocks the binding of a reference antibody to an antigen (e.g., a GITR) by 50% or more in a competitive assay. Exemplary competitive assays are described in "Antibodies", Harbor and Lane (Cold Spring Harbor Press, Cold Spring Harbor, N.Y.). The antibody that competes for binding the reference antibody can bind to the same epitope region, e.g., the same epitope, adjacent epitopes or overlapping epitopes.

As used herein, the term "Fc region" defines the C-terminal region of an immunoglobulin heavy chain that comprises at least a part of constant regions. The term includes an Fc-region of native sequence and a variant Fc-region. In one embodiment, a human IgG heavy chain Fc-region extends from Cys226 or from Pro230 of a heavy chain to a carboxyl terminus. However, the C-terminal lysine (Lys447) of the Fc region may or may not be present. Unless otherwise indicated herein, the numbering of amino acid residues in the Fc-region or constant region is based on the EU numbering system, also known as the EU index, as described in Kabat, E. A., et al., Sequences of Proteins of Immunological Interest, 5th edition, Public Health Service, National Institutes of Health, Bethesda, Md. (1991), NIH Publication 91-3242.

The term "variant" related to an antibody herein refers to an antibody that comprises a target antibody region (e.g., a heavy chain variable region, a light chain variable region, a heavy chain CDR region or a light chain CDR region) having amino acid alterations by virtue of at least one, such as 1-30, 1-20 or 1-10, e.g., 1, 2, 3, 4 or 5 amino acid substitutions, deletions and/or insertions, wherein the variant substantially retains the biological properties of the antibody molecule prior to alteration.

As used herein, the term "sequence identity" refers to the degree to which sequences are identical on a nucleotide-by-nucleotide or amino acid-by-amino acid basis in a comparison window. The "percent sequence identity" can be calculated by the following steps: comparing two optimally aligned sequences in a comparison window; determining the number of positions in which nucleic acid bases (e.g., A, T, C, G and I) or amino acid residues (e.g., Ala, Pro, Ser, Thr, Gly, Val, Leu, Ile, Phe, Tyr, Trp, Lys, Arg, His, Asp, Glu, Asn, Gln, Cys, and Met) are the same in the two sequences to yield the number of matched positions; dividing the number of matched positions by the total number of positions in the comparison window (i.e., the window size); and multiplying the result by 100 to yield a percent sequence identity. Optimal alignment for determining the percent sequence identity may be implemented in a variety of ways known in the art, for example, using publicly available computer software such as BLAST, BLAST-2, ALIGN, or Megalign (DNASTAR) software. Those skilled in the art can determine suitable parameters for alignment of the sequences, including any algorithms necessary to yield an optimal alignment in a full-length range or target sequence region to be compared.

Herein, with respect to antibody sequences, the percent amino acid sequence identity is determined by optimally aligning a candidate antibody sequence with a reference antibody sequence, and in one preferred embodiment, optimal alignment is implemented according to the Kabat numbering scheme. After alignment, a target antibody region (e.g., the entire heavy or light chain variable region, or a portion thereof such as one or more CDR regions) is compared to the same region of the reference antibody. The percent sequence identity between the target antibody region and the reference antibody region is a percent obtained by the following steps: dividing the number of positions having same amino acids in both target and reference antibody regions by the total number of aligned positions for the two regions (gaps are not counted); and multiplying the result by 100. Herein, without specifying the target antibody region, it will be applicable to align over the full length of the reference antibody sequence. In some embodiments, with respect to antibodies, the sequence identity may be based on the entire heavy chain variable region and/or the entire light chain variable region, or the percent sequence identity may be limited to the framework regions only, while the sequences of corresponding CDR regions remain 100% identical.

The "conservative substitution" used herein refers to an amino acid alteration that results in the replacement of an amino acid with a chemically similar amino acid. Conservative substitution tables that provide functionally similar amino acids are well known in the art. In any of the embodiments herein, in one preferred aspect, conservatively substituted residues are selected from the Table A of conservative substitutions below, preferably the preferred substituted residues shown in Table A.

TABLE A

| Primitive residue | Exemplary substitution | Preferred conservative amino acid substitution |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Nle | Leu |
| Leu (L) | Nle, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Nle | Leu |

The terms "individual" and "subject" used herein can be used interchangeably and refer to a mammal. The mammals include, but are not limited to, domesticated animals (e.g., cows, sheep, cats, dogs, and horses), primates (e.g., human and non-human primates such as monkeys), rabbits and rodents (e.g., mice and rats). In particular, the subject is a human.

The term "treatment" used herein refers to a clinical intervention intended to alter the natural progress of the disease in an individual being treated. Desired therapeutic effects include, but are not limited to, preventing the occurrence or recurrence of diseases, alleviating symptoms, reducing any direct or indirect pathological outcomes of diseases, preventing metastasis, delaying disease progression, improving or alleviating conditions, and improving prognosis.

The terms "cancer", "tumor", "cancerous", and "malignant" used herein refer to or describe a physiological disease in mammals that is typically characterized by unregulated cell growth. Examples of cancers include, but are not limited to, carcinomas (including adenocarcinomas), lymphomas, blastomas, melanomas, sarcomas, and leukemias. More specific examples of such cancers include: squamous cell carcinoma, small cell lung cancer, non-small cell lung cancer, gastrointestinal cancer, Hodgkin's and non-Hodgkin's lymphoma, pancreatic cancer, glioblastoma, neuroglioma, cervical cancer, ovarian cancer, liver cancer such as hepatic carcinoma and hepatocellular carcinoma, bladder cancer, breast cancer, colon cancer, colorectal cancer, endometrial cancer, myeloma (such as multiple myeloma), salivary gland carcinoma, kidney cancers such as renal cell carcinoma and Wilms' tumor, basal cell carcinoma, melanoma, prostate cancer, vulval cancer, thyroid cancer, testicular cancer, esophageal cancer, and various types of head and neck cancer.

With the growth and proliferation of cancerous cells, cancerous masses, which are tumors that invade and destroy nearby tissues and organs, are formed. Malignant tumors are cancers. Malignant tumors are often resectable, but may regenerate. Cells of malignant tumors can invade and destroy nearby tissues and organs. In addition, cancer cells may depart from malignant tumors and enter blood or lymphatic system, which is a pathway for cancer cells to migrate from the primary lesion (i.e., the primary cancer) to new lesions in other organs. The migration of cancer in the body is known as metastasis (*What You Need to Know About Cancer-an Overview*, NIH Publication No. 00-1566; published on Sep. 26, 2000, and updated on Sep. 16, 2002 (2002)).

2. Detailed Descriptions

Unless otherwise indicated, conventional methods of chemistry, biochemistry, organic chemistry, molecular biology, microbiology, recombinant DNA techniques, genetics, immunology and cell biology that are known in the art will be employed for the implementation of the present invention. Descriptions of such methods may be found, for example, in Sambrook et al., *Molecular Cloning: A Laboratory Manual* (3rd edition, 2001); Sambrook et al., *Molecular Cloning: A Laboratory Manual* (2nd edition, 1989); Maniatis et al., *Molecular Cloning: A Laboratory Manual* (1982); Ausubel et al., *Current Protocols in Molecular Biology* (John Wiley and Sons, updated in July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I&II (IRL Press, Oxford, 1985); Anand, *Techniques for the Analysis of Complex Genomes*, (Academic Press, New York, 1992); *Transcription and Translation* (B. Hames & S. Higgins, eds., 1984); Perbal, *A Practical Guide to Molecular Cloning* (1984); Harlow and Lane, *Antibodies*, (Cold Spring Harbor Laboratory Press, Cold Spring Harbor, N.Y., 1998); *Current Protocols in Immunology*, (Q. E. Coligan, A. M. Kruisbeek, D. H. Margulies, E. M. Shevach and W. Strober, eds., 1991); *Annual Review of Immunology*; and journals and monographs such as *Advances in Immunology*.

In an aspect, the present invention provides an antibody or antigen-binding fragment thereof that can specifically bind to a glucocorticoid-induced tumor necrosis factor receptor (GITR), and effectively activate the NF-κB signaling pathway downstream of GITR (i.e., the antibody or antigen-binding fragment disclosed herein).

In some embodiments, the antibody disclosed herein is a monoclonal antibody or a multispecific antibody (including diabody); and/or is selected from IgG1, IgG2, IgG3, and IgG4; and/or is an antigen-binding fragment, such as Fab', $F(ab')_2$ or Fv; and/or is a human antibody, a humanized antibody or a chimeric antibody; and/or is a labeled antibody.

In some embodiments, the antibody disclosed herein is a miniaturized antibody specifically binding to GITR, such as a single-chain variable fragment (scFv) specifically binding to a GITR, a single-domain antibody (sdAd), a heavy-chain antibody (hcAb), and a nanobody (Nb or VHH); or a polymeric form thereof. Such a miniaturized antibody preferably comprises the HCDR3 (heavy chain complementarity determining region 3) in the heavy chain variable region of the antibody disclosed herein; more preferably comprises the HCDR1 (heavy chain complementarity determining region 1) and the HCDR2 (heavy chain complementarity determining region 2) in the heavy chain variable region of the antibody disclosed herein.

The present invention encompasses variants of any of the antibodies disclosed herein. In one embodiment, the antibody variant retains at least 60%, 70%, 80%, 90% or 100% of the bioactivity (e.g., antigen-binding capacity) of the antibody prior to alteration. In some embodiments, the alteration does not result in loss of binding capability of antibody variants to antigens, but optionally may confer properties such as increased antigen affinity and different effector functions. It will be appreciated that the heavy or light chain variable regions of the antibody, or each CDR region of the heavy or light chain variable regions may be altered independently or in combination. In some embodiments, there are no more than 1, 2, 3, 4, 5, 6, 7, 8, 9, or 10 amino acid alterations in one or more or all of the three heavy chain CDRs. Preferably, the amino acid alteration refers to an amino acid substitution, preferably a conservative substitution. In some embodiments, there are no more than 1, 2, 3, 4, 5, 6, 7, 8, 9, or 10 amino acid alterations in one or more or all of the three heavy chain CDRs. Preferably, the amino acid alteration refers to an amino acid substitution, preferably a conservative substitution. In some embodiments, the antibody variant has at least 80%, 85%, 90%, 95%, 99% or higher amino acid identity to a parent antibody in a target antibody sequence region. In one embodiment, the antibody disclosed herein has at least 80%, 85%, 90%, 91%, 92%, 93%, 94%, 95%, 96%, 97%, 98%, 99% or higher sequence identity to any one of the antibodies listed in Table B in the heavy chain variable region.

For example, the antibody disclosed herein comprises at least one, two, three, four, five, or six CDRs identical to corresponding CDRs of any one of the antibodies listed in Table B, or variants thereof. In some embodiments, the antibody disclosed herein comprises at least one, two, or three HCDRs identical to the corresponding heavy chain CDRs of any one of the antibodies listed in Table B, or variants thereof. The term "corresponding CDRs" used herein refers to CDRs located at substantially similar positions in a variable region amino acid sequence. A CDR variant described herein is a CDR that has been modified by at least one, e.g., 1 or 2 or 3 amino acid substitutions, deletions, and/or insertions, wherein an antibody molecule comprising the CDR variant substantially retains the biological properties of an antibody molecule comprising the unmodified CDR, e.g., retains at least 60%, 70%, 80%, 90%, or 100% of the bioactivity (e.g., antigen-binding capacity). It will be appreciated that each CDR may be modified independently or in combination. Preferably, an amino acid modification is an amino acid substitution, in particular a conservative amino acid substitution, such as a preferred conservative amino acid substitution listed in Table A.

In some embodiments, the antibody or the antigen-binding fragment thereof disclosed herein binds to a GITR with high specificity and high affinity.

In some embodiments, the antibody or the antigen-binding fragment thereof disclosed herein binds to a human GITR (such as a polypeptide set forth in SEQ ID NO: 123 or 127) with high affinity, e.g., with affinity of less than about 50 nM, less than about 30 nM, less than about 10-25 nM or less than about 20 nM, preferably less than about 10 nM.

For example, the antibody or the antigen-binding fragment thereof disclosed herein binds to a human GITR (such as a polypeptide set forth in SEQ ID NO: 123 or 127) with high affinity of about 1-50 nM, about 5-50 nM, about 10-50 nM, about 1-30 nM, about 5-30 nM, about 10-30 nM, about 1-25 nM, about 5-25 nM, about 10-25 nM, about 1-20 nM, about 5-20 nM, about 10-20 nM, about 0.1-10 nM, about 1-10 nM, about 5-10 nM, and about 10 nM.

In some embodiments, the antibody or the antigen-binding fragment thereof disclosed herein binds to a human GITR (such as a polypeptide set forth in SEQ ID NO: 123 or 127) with high affinity, e.g., with a dissociation constant of greater than about $0.01 \times 10^4$/Ms, greater than about $0.1 \times 10^4$/Ms, greater than about $1 \times 10^4$/Ms, or greater than about $3 \times 10^4$/Ms, preferably greater than about $5 \times 10^4$/Ms.

In some embodiments, the antibody or the antigen-binding fragment thereof disclosed herein binds to a human GITR (such as a polypeptide set forth in SEQ ID NO: 123 or 127) with a low dissociation constant, e.g., with a dissociation constant ($K_d$) of less than about $2 \times 10^{-2} s^{-1}$, less than about $1.5 \times 10^{-2} s^{-1}$, less than about $8 \times 10^{-3} s^{-1}$, or less than about $5 \times 10^{-3} s^{-1}$; preferably about $1$-$3 \times 10^{-3} s^{-1}$.

For example, the antibody or the antigen-binding fragment thereof disclosed herein binds to a human GITR (such as a polypeptide set forth in SEQ ID NO: 123 or 127) with a dissociation constant ($K_d$) of about $1 \times 10^{-4} s^{-1}$ to $2 \times 10^{-2} s^{-1}$, about $1 \times 10^{-3} s^{-1}$ to $2 \times 10^{-2} s^{-1}$, about $3 \times 10^{-3} s^{-1}$ to $2 \times 10^{-2} s^{-1}$, about $1 \times 10^{-4} s^{-1}$ to $1.5 \times 10^{-2} s^{-1}$, about $1 \times 10^{-3} s^{-1}$ to $1.5 \times 10^{-2} s^{-1}$, about $3 \times 10^{-3} s^{-1}$ to $1.5 \times 10^{-2} s^{-1}$, about $1 \times 10^{-4} s^{-1}$ to $8 \times 10^{-2} s^{-1}$, about $1 \times 10^{-3} s^{-1}$ to $8 \times 10^{-2} s^{-1}$, about $3 \times 10^{-3} s^{-1}$ to $1.5 \times 10^{-2} s^{-1}$, about $1 \times 10^{-4} s^{-1}$ to $5 \times 10^{-2} s^{-1}$, about $1 \times 10^{-3} s^{-1}$ to $5 \times 10^{-2} s^{-1}$, about $3 \times 10^{-3} s^{-1}$ to $1.5 \times 10^{-2} s^{-1}$, $1 \times 10^{-3} s^{-1}$ to $2 \times 10^{-2} s^{-1}$, and about $3 \times 10^{-3} s^{-1}$ to $1.5 \times 10^{-2} s^{-1}$.

In some embodiments, the antibody or the antigen-binding fragment thereof disclosed herein binds to antigens expressed on a cell surface with high affinity, e.g., to human GITRs (such as a polypeptide set forth in SEQ ID NO: 123 or 127) with affinity of less than about 50 nM, less than about 30 nM, less than about 25 nM or less than about 20 nM, preferably less than about 10 nM.

For example, the antibody or the antigen-binding fragment thereof disclosed herein binds to antigens expressed on a cell surface with affinity of about 1-50 nM, about 5-50 nM, about 10-50 nM, about 1-30 nM, about 5-30 nM, about 10-30 nM, about 1-25 nM, about 5-25 nM, about 10-25 nM, about 1-20 nM, about 5-20 nM, about 10-20 nM, about 0.1-10 nM, about 1-10 nM, about 5-10 nM, and about 10 nM.

In some embodiments, the antibody or the antigen-binding fragment thereof disclosed herein efficiently activates the NF-κB signaling pathway downstream of the GITR, e.g., with an $EC_{50}$ value of less than about 50 nM, less than about 30 nM, less than about 25 nM, or less than about 5 nM, and preferably less than about 1 nM, for activating the NF-κB signaling pathway.

For example, the antibody or the antigen-binding fragment thereof disclosed herein activates the NF-κB signaling pathway with an $EC_{50}$ value of about 1 nM to 50 nM, about 5 nM to 50 nM, about 10 nM to 50 nM, about 1 nM to 30 nM, about 5 nM to 30 nM, about 10 nM to 30 nM, about 1 nM to 25 nM, about 5 nM to 25 nM, about 10 nM to 25 nM, about 1 nM to 20 nM, about 5 nM to 20 nM, about 10 nM to 20 nM, about 0.1 nM to 10 nM, about 1 nM to 10 nM, about 5 nM to 10 nM, or about 10 nM.

In some embodiments, the antibody or the antigen-binding fragment thereof disclosed herein cross-competes with GITRLs for binding to GITRs, and preferably for binding to human GITRs (e.g., a polypeptide of SEQ ID NO: 123 or 127).

In some embodiments, the antibody or the antigen-binding fragment thereof disclosed herein can be internalized into human CD4 cells.

In some embodiments, the antibody or the antigen-binding fragment thereof disclosed herein inhibits the inhibitory effect of regulatory T cells.

In some embodiments, the antibody or the antigen-binding fragment thereof disclosed herein activates effector T cells.

In some embodiments, the antibody or the antigen-binding fragment thereof disclosed herein reduces the circulating regulatory T cells.

In some embodiments, the antibody or the antigen-binding fragment thereof disclosed herein can bind to an Fcγ receptor (FcγR).

In some embodiments, the antibody or the antigen-binding fragment thereof disclosed herein has a half-life of at least about 6, about 7, about 9 or about 12 days in human serum.

In another aspect, the present invention provides a nanobody that specifically binds to a GITR and efficiently activates the NF-κB signaling pathway downstream of the GITR (i.e., the nanobody disclosed herein), and HCDR3 of the nanobody comprises the HCDR3 of the antibody or the antigen-binding fragment thereof disclosed herein.

In some embodiments, the HCDR3 of the nanobody disclosed herein comprises HCDR3 contained in a heavy-chain variable region sequence set forth in any one of SEQ ID NOs: 64-85, or HCDR3 of the nanobody disclosed herein consists of HCDR3 contained in a heavy-chain variable region sequence set forth in any one of SEQ ID NOs: 64-85.

In some embodiments, the HCDR3 of the nanobody disclosed herein comprises HCDR3 contained in a heavy-chain variable region sequence having at least 90%, 91%, 92%, 93%, 94%, 95%, 96%, 97%, 98%, 99% or more sequence identity with a heavy-chain variable region sequence set forth in any one of SEQ ID NOs: 64-85, wherein preferably, the sequence difference does not exist in the CDR region; or the HCDR3 of the nanobody disclosed herein consists of HCDR3 contained in such a heavy-chain variable region sequence.

In some embodiments, the HCDR3 of the nanobody disclosed herein comprises HCDR3 contained in a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in any one of SEQ ID NOs: 64-85, wherein preferably, the amino acid alterations do not occur in the CDR region; or the HCDR3 of the nanobody disclosed herein consists of HCDR3 contained in such a heavy-chain variable region sequence.

In some embodiments, the HCDR3 of the nanobody disclosed herein comprises HCDR3 set forth in any one of SEQ ID NOs: 45-63, or the HCDR3 of the nanobody disclosed herein consists of HCDR3 set forth in any one of SEQ ID NOs: 45-63.

In some embodiments, the HCDR3 of the nanobody disclosed herein comprises HCDR3 having one or more (preferably 1 to 10, more preferably 1 to 5, and most preferably 1 to 3) amino acid alterations (preferably substitution, and more preferably conservative substitution) relative to HCDR3 set forth in any one of SEQ ID NOs: 45-63, or the HCDR3 of the nanobody disclosed herein consists of such HCDR3.

In some embodiments, the HCDR1 (heavy-chain complementarity determining region 1) and the HCDR2 (heavy-chain complementarity determining region 2) of the nanobody disclosed herein comprises HCDR1 and HCDR2 contained in a heavy-chain variable region sequence set forth in any one of SEQ ID NOs: 64-85, or the HCDR1 and the HCDR2 of the nanobody disclosed herein consists of HCDR1 and HCDR2 contained in a heavy-chain variable region sequence set forth in any one of SEQ ID NOs: 64-85.

In some embodiments, the HCDR1 and the HCDR2 of the nanobody disclosed herein comprises HCDR1 and HCDR2 contained in a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in any one of SEQ ID NOs: 64-85, wherein preferably, the amino acid alterations do not occur in the CDR region; or the HCDR1 and the HCDR2 of the nanobody disclosed herein consists of HCDR1 and HCDR2 contained in such a heavy-chain variable region sequence.

In some embodiments, the HCDR1 of the nanobody disclosed herein comprises HCDR1 set forth in any one of SEQ ID NOs: 1-22, or the HCDR1 of the nanobody disclosed herein consists of HCDR1 set forth in any one of SEQ ID NOs: 1-22.

In some embodiments, the HCDR1 of the nanobody disclosed herein comprises HCDR1 having one or more (preferably 1 to 10, more preferably 1 to 5, and most preferably 1 to 3) amino acid alterations (preferably substitution, and more preferably conservative substitution) relative to HCDR1 set forth in any one of SEQ ID NOs: 1-22, wherein preferably, the amino acid alterations do not occur in the CDR region; or the HCDR1 of the nanobody disclosed herein consists of such HCDR1.

In some embodiments, the HCDR2 of the nanobody disclosed herein comprises HCDR2 set forth in any one of SEQ ID NOs: 23-44, or the HCDR2 of the nanobody disclosed herein consists of HCDR2 set forth in any one of SEQ ID NOs: 23-44.

In some embodiments, the HCDR2 of the nanobody disclosed herein comprises HCDR2 having one or more (preferably 1 to 10, more preferably 1 to 5, and most preferably 1 to 3) amino acid alterations (preferably substitution, and more preferably conservative substitution) relative to HCDR2 set forth in any one of SEQ ID NOs: 23-44, or the HCDR2 of the nanobody disclosed herein consists of such HCDR2.

In some embodiments, the nanobody disclosed herein comprises a combination of HCDR1 set forth in SEQ ID NO: 1, HCDR2 set forth in SEQ ID NO: 23, and HCDR3 set forth in SEQ ID NO: 45.

In some embodiments, the nanobody disclosed herein comprises a combination of HCDR1 set forth in SEQ ID NO: 2, HCDR2 set forth in SEQ ID NO: 24, and HCDR3 set forth in SEQ ID NO: 46.

In some embodiments, the nanobody disclosed herein comprises a combination of HCDR1 set forth in SEQ ID NO: 3, HCDR2 set forth in SEQ ID NO: 25, and HCDR3 set forth in SEQ ID NO: 47.

In some embodiments, the nanobody disclosed herein comprises a combination of HCDR1 set forth in SEQ ID NO: 4, HCDR2 set forth in SEQ ID NO: 26, and HCDR3 set forth in SEQ ID NO: 48.

In some embodiments, the nanobody disclosed herein comprises a combination of HCDR1 set forth in SEQ ID NO: 5, HCDR2 set forth in SEQ ID NO: 27, and HCDR3 set forth in SEQ ID NO: 49.

In some embodiments, the nanobody disclosed herein comprises a combination of HCDR1 set forth in SEQ ID NO: 6, HCDR2 set forth in SEQ ID NO: 28, and HCDR3 set forth in SEQ ID NO: 50.

In some embodiments, the nanobody disclosed herein comprises a combination of HCDR1 set forth in SEQ ID NO: 7, HCDR2 set forth in SEQ ID NO: 29, and HCDR3 set forth in SEQ ID NO: 51.

In some embodiments, the nanobody disclosed herein comprises a combination of HCDR1 set forth in SEQ ID NO: 8, HCDR2 set forth in SEQ ID NO: 30, and HCDR3 set forth in SEQ ID NO: 52.

In some embodiments, the nanobody disclosed herein comprises a combination of HCDR1 set forth in SEQ ID NO: 9, HCDR2 set forth in SEQ ID NO: 31, and HCDR3 set forth in SEQ ID NO: 53.

In some embodiments, the nanobody disclosed herein comprises a combination of HCDR1 set forth in SEQ ID NO: 10, HCDR2 set forth in SEQ ID NO: 32, and HCDR3 set forth in SEQ ID NO: 51.

In some embodiments, the nanobody disclosed herein comprises a combination of HCDR1 set forth in SEQ ID NO: 11, HCDR2 set forth in SEQ ID NO: 33, and HCDR3 set forth in SEQ ID NO: 48.

In some embodiments, the nanobody disclosed herein comprises a combination of HCDR1 set forth in SEQ ID NO: 12, HCDR2 set forth in SEQ ID NO: 34, and HCDR3 set forth in SEQ ID NO: 46.

In some embodiments, the nanobody disclosed herein comprises a combination of HCDR1 set forth in SEQ ID NO: 13, HCDR2 set forth in SEQ ID NO: 35, and HCDR3 set forth in SEQ ID NO: 54.

In some embodiments, the nanobody disclosed herein comprises a combination of HCDR1 set forth in SEQ ID NO: 14, HCDR2 set forth in SEQ ID NO: 36, and HCDR3 set forth in SEQ ID NO: 55.

In some embodiments, the nanobody disclosed herein comprises a combination of HCDR1 set forth in SEQ ID NO: 15, HCDR2 set forth in SEQ ID NO: 37, and HCDR3 set forth in SEQ ID NO: 56.

In some embodiments, the nanobody disclosed herein comprises a combination of HCDR1 set forth in SEQ ID NO: 16, HCDR2 set forth in SEQ ID NO: 38, and HCDR3 set forth in SEQ ID NO: 57.

In some embodiments, the nanobody disclosed herein comprises a combination of HCDR1 set forth in SEQ ID NO: 17, HCDR2 set forth in SEQ ID NO: 39, and HCDR3 set forth in SEQ ID NO: 58.

In some embodiments, the nanobody disclosed herein comprises a combination of HCDR1 set forth in SEQ ID NO: 18, HCDR2 set forth in SEQ ID NO: 40, and HCDR3 set forth in SEQ ID NO: 59.

In some embodiments, the nanobody disclosed herein comprises a combination of HCDR1 set forth in SEQ ID NO: 19, HCDR2 set forth in SEQ ID NO: 41, and HCDR3 set forth in SEQ ID NO: 60.

In some embodiments, the nanobody disclosed herein comprises a combination of HCDR1 set forth in SEQ ID NO: 20, HCDR2 set forth in SEQ ID NO: 42, and HCDR3 set forth in SEQ ID NO: 61.

In some embodiments, the nanobody disclosed herein comprises a combination of HCDR1 set forth in SEQ ID NO: 21, HCDR2 set forth in SEQ ID NO: 43, and HCDR3 set forth in SEQ ID NO: 62.

In some embodiments, the nanobody disclosed herein comprises a combination of HCDR1 set forth in SEQ ID NO: 22, HCDR2 set forth in SEQ ID NO: 44, and HCDR3 set forth in SEQ ID NO: 63.

In some embodiments, the nanobody disclosed herein comprises a heavy-chain variable region sequence set forth in any one of SEQ ID NOs: 64-85, or consists of a heavy-chain variable region sequence set forth in any one of SEQ ID NOs: 64-85, and preferably consists of only one heavy-chain variable region sequence described above.

In some embodiments, the nanobody disclosed herein comprises a heavy-chain variable region sequence having at least 90%, 91%, 92%, 93%, 94%, 95%, 96%, 97%, 98%, 99% or more sequence identity with a heavy-chain variable region sequence set forth in any one of SEQ ID NOs: 64-85, wherein preferably, the sequence difference does not exist in the CDR region; or the nanobody disclosed herein consists of such a heavy-chain variable region sequence, and preferably consists of only one heavy-chain variable region sequence described above.

In some embodiments, the nanobody disclosed herein comprises a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in any one of SEQ ID NOs: 64-85, wherein preferably, the amino acid alterations do not occur in the CDR region; or the nanobody disclosed herein consists of such a heavy-chain variable region sequence, and preferably consists of only one heavy-chain variable region sequence described above.

In another aspect, the present invention provides a heavy-chain antibody that specifically binds to a GITR and efficiently activates the NF-κB signaling pathway downstream of the GITR (i.e., the heavy-chain antibody disclosed herein). HCDR3 of the heavy-chain antibody comprises or consists of the HCDR3 of the antibody or the antigen-binding fragment thereof disclosed herein; preferably, HCDR3 of the heavy-chain antibody comprises or consists of the HCDR3 of the above-mentioned nanobody disclosed herein; and more preferably, HCDR1 and HCDR2 of the heavy-chain antibody respectively comprise or consist of the HCDR1 and the HCDR2 of the above-mentioned nanobody disclosed herein.

In some embodiments, the heavy-chain antibody disclosed herein is a humanized heavy-chain antibody, and preferably a fully humanized heavy-chain antibody (a human antibody).

In some embodiments, the HCDR3 of the heavy-chain antibody disclosed herein comprises HCDR3 contained in a heavy-chain variable region sequence set forth in any one of SEQ ID NOs: 65, 66, 67, 70, 72, 73, 79, and 83, or the HCDR3 of the heavy-chain antibody disclosed herein consists of HCDR3 contained in a heavy-chain variable region sequence set forth in any one of SEQ ID NOs: 65, 66, 67, 70, 72, 73, 79, and 83. In some embodiments, the HCDR3 of the heavy-chain antibody disclosed herein comprises HCDR3 contained in a heavy-chain variable region sequence having at least 90%, 91%, 92%, 93%, 94%, 95%, 96%, 97%, 98%, 99% or more sequence identity with a heavy-chain variable region sequence set forth in any one of SEQ ID NOs: 65, 66, 67, 70, 72, 73, 79, and 83, wherein preferably, the sequence difference does not exist in the CDR region; or the HCDR3 of the heavy-chain antibody disclosed herein consists of HCDR3 contained in such a heavy-chain variable region sequence.

In some embodiments, the HCDR3 of the heavy-chain antibody disclosed herein comprises HCDR3 contained in a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in any one of SEQ ID NOs: 65, 66, 67, 70, 72, 73, 79, and 83, wherein preferably, the amino acid alterations do not occur in the CDR region; or the HCDR3 of the heavy-chain antibody disclosed herein consists of HCDR3 contained in such a heavy-chain variable region sequence.

In some embodiments, the HCDR3 of the heavy-chain antibody disclosed herein comprises HCDR3 set forth in any one of SEQ ID NOs: 46, 47, 48, 51, 53, 57, and 61, or the HCDR3 of the heavy-chain antibody disclosed herein consists of HCDR3 set forth in any one of SEQ ID NOs: 46, 47, 48, 51, 53, 57, and 61.

In some embodiments, the HCDR3 of the heavy-chain antibody disclosed herein comprises HCDR3 having one or more (preferably 1 to 10, more preferably 1 to 5, and most preferably 1 to 3) amino acid alterations (preferably substitution, and more preferably conservative substitution) relative to HCDR3 set forth in any one of SEQ ID NOs: 46, 47, 48, 51, 53, 57, and 61, or the HCDR3 of the heavy-chain antibody disclosed herein consists of such HCDR3.

In some embodiments, the HCDR1 and the HCDR2 of the heavy-chain antibody disclosed herein comprise HCDR1 and HCDR2 contained in a heavy-chain variable region sequence set forth in any one of SEQ ID NOs: 65, 66, 67, 70, 72, 73, 79, and 83, or the HCDR1 and the HCDR2 of the heavy-chain antibody disclosed herein consist of HCDR1 and HCDR2 contained in such a heavy-chain variable region sequence.

In some embodiments, the HCDR1 and the HCDR2 of the heavy-chain antibody disclosed herein comprise HCDR1 and HCDR2 contained in a heavy-chain variable region sequence having at least 90%, 91%, 92%, 93%, 94%, 95%, 96%, 97%, 98%, 99% or more sequence identity with a heavy-chain variable region sequence set forth in any one of SEQ ID NOs: 65, 66, 67, 70, 72, 73, 79, and 83, wherein preferably, the sequence difference does not exist in the CDR region; or the HCDR1 and the HCDR2 of the heavy-chain antibody disclosed herein consist of HCDR1 and HCDR2 contained in such a heavy-chain variable region sequence.

In some embodiments, the HCDR1 and the HCDR2 of the heavy-chain antibody disclosed herein comprise HCDR1 and HCDR2 contained in a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in any one of SEQ ID NOs: 65, 66, 67, 70, 72, 73, 79, and 83, wherein preferably, the amino acid alterations do not occur in the CDR region; or the HCDR1 and the HCDR2 of the heavy-chain antibody disclosed herein consist of HCDR1 and HCDR2 contained in such a heavy-chain variable region sequence.

In some embodiments, the HCDR1 of the heavy-chain antibody disclosed herein comprises HCDR1 set forth in any one of SEQ ID NOs: 2, 3, 4, 7, 9, 10, 16, and 20, or the HCDR1 of the heavy-chain antibody disclosed herein consists of HCDR1 set forth in any one of SEQ ID NOs: 2, 3, 4, 7, 9, 10, 16, and 20.

In some embodiments, the HCDR1 of the heavy-chain antibody disclosed herein comprises HCDR1 having one or more (preferably 1 to 10, more preferably 1 to 5, and most preferably 1 to 3) amino acid alterations (preferably substitution, and more preferably conservative substitution) relative to HCDR1 set forth in any one of SEQ ID NOs: 2, 3, 4, 7, 9, 10, 16, and 20, or the HCDR1 of the heavy-chain antibody disclosed herein consists of such HCDR1.

In some embodiments, the HCDR2 of the heavy-chain antibody disclosed herein comprises HCDR2 set forth in any one of SEQ ID NOs: 24, 25, 26, 29, 31, 32, 38, and 42, or the HCDR2 of the heavy-chain antibody disclosed herein consists of HCDR2 set forth in any one of SEQ ID NOs: 24, 25, 26, 29, 31, 32, 38, and 42.

In some embodiments, the HCDR2 of the heavy-chain antibody disclosed herein comprises HCDR2 having one or more (preferably 1 to 10, more preferably 1 to 5, and most preferably 1 to 3) amino acid alterations (preferably substitution, and more preferably conservative substitution) relative to HCDR2 set forth in any one of SEQ ID NOs: 24, 25, 26, 29, 31, 32, 38, and 42, or the HCDR2 of the heavy-chain antibody disclosed herein consists of such HCDR2.

In some embodiments, the heavy-chain antibody disclosed herein comprises a combination of HCDR1 set forth in SEQ ID NO: 2, HCDR2 set forth in SEQ ID NO: 24, and HCDR3 set forth in SEQ ID NO: 46.

In some embodiments, the heavy-chain antibody disclosed herein comprises a combination of HCDR1 set forth in SEQ ID NO: 3, HCDR2 set forth in SEQ ID NO: 25, and HCDR3 set forth in SEQ ID NO: 47.

In some embodiments, the heavy-chain antibody disclosed herein comprises a combination of HCDR1 set forth in SEQ ID NO: 4, HCDR2 set forth in SEQ ID NO: 26, and HCDR3 set forth in SEQ ID NO: 48.

In some embodiments, the heavy-chain antibody disclosed herein comprises HCDR1 set forth in SEQ ID NO: 7, HCDR2 set forth in SEQ ID NO: 29, and HCDR3 set forth in SEQ ID NO: 51.

In some embodiments, the heavy-chain antibody disclosed herein comprises HCDR1 set forth in SEQ ID NO: 9, HCDR2 set forth in SEQ ID NO: 31, and HCDR3 set forth in SEQ ID NO: 53.

In some embodiments, the heavy-chain antibody disclosed herein comprises HCDR1 set forth in SEQ ID NO: 10, HCDR2 set forth in SEQ ID NO: 32, and HCDR3 set forth in SEQ ID NO: 51.

In some embodiments, the heavy-chain antibody disclosed herein comprises HCDR1 set forth in SEQ ID NO: 16, HCDR2 set forth in SEQ ID NO: 38, and HCDR3 set forth in SEQ ID NO: 57.

In some embodiments, the heavy-chain antibody disclosed herein comprises HCDR1 set forth in SEQ ID NO: 20, HCDR2 set forth in SEQ ID NO: 42, and HCDR3 set forth in SEQ ID NO: 61.

In some embodiments, the heavy-chain variable region sequence of the heavy-chain antibody disclosed herein comprises a heavy-chain variable region sequence set forth in any one of SEQ ID NOs: 65, 66, 67, 70, 72, 73, 79, and 83, or the heavy-chain variable region sequence of the heavy-chain antibody disclosed herein consists of a heavy-chain variable region sequence set forth in any one of SEQ ID NOs: 65, 66, 67, 70, 72, 73, 79, and 83.

In some embodiments, the heavy-chain variable region sequence of the heavy-chain antibody disclosed herein comprises a heavy-chain variable region sequence having at least 90%, 91%, 92%, 93%, 94%, 95%, 96%, 97%, 98%, 99% or more sequence identity with a heavy-chain variable region sequence set forth in any one of SEQ ID NOs: 65, 66, 67, 70, 72, 73, 79, and 83, wherein preferably, the sequence difference does not exist in the CDR region; or the heavy-chain variable region sequence of the heavy-chain antibody disclosed herein consists of such a heavy-chain variable region sequence.

In some embodiments, the heavy-chain variable region sequence of the heavy-chain antibody disclosed herein comprises a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in any one of SEQ ID NOs: 65, 66, 67, 70, 72, 73, 79, and 83, wherein preferably, the amino acid alterations do not occur in the CDR region; or the heavy-chain variable region sequence of the heavy-chain antibody disclosed herein consists of such a heavy-chain variable region sequence.

In some embodiments, the heavy-chain antibody disclosed herein comprises a heavy-chain antibody sequence set forth in any one of SEQ ID NOs: 108-115, or the heavy-chain antibody disclosed herein consists of one, two or more heavy-chain antibody sequences set forth in any one of SEQ ID NOs: 108-115.

In some embodiments, the heavy-chain antibody disclosed herein comprises a heavy-chain antibody sequence having at least 90%, 91%, 92%, 93%, 94%, 95%, 96%, 97%, 98%, 99% or more sequence identity with a heavy-chain antibody sequence set forth in any one of SEQ ID NOs: 108-115, wherein preferably, the sequence difference does not exist in the CDR region; or the heavy-chain antibody disclosed herein consists of one, two or more heavy-chain antibody sequences described above.

In some embodiments, the heavy-chain antibody disclosed herein comprises a heavy-chain antibody sequence having one or more (preferably 1 to 10, more preferably 1 to 5, and most preferably 1 to 3) amino acid alterations (preferably substitution, and more preferably conservative substitution) relative to a heavy-chain antibody sequence set forth in any one of SEQ ID NOs: 108-115, wherein preferably, the amino acid alterations do not occur in the CDR region; or the heavy-chain antibody disclosed herein consists of one, two or more heavy-chain antibody sequences described above.

In another aspect, the present invention provides a humanized heavy-chain antibody that specifically binds to a GITR and efficiently activates the NF-κB signaling pathway downstream of the GITR (i.e., the humanized heavy-chain antibody disclosed herein), and HCDR3 of the humanized heavy-chain antibody comprises or consists of the HCDR3 of the antibody or the antigen-binding fragment thereof disclosed herein.

In some embodiments, the HCDR3 of the humanized heavy-chain antibody disclosed herein comprises or consists of the HCDR3 of the nanobody or the heavy-chain antibody disclosed herein, and preferably, the HCDR1 and the HCDR2 of the humanized heavy-chain antibody disclosed herein respectively comprise or consist of the HCDR1 and the HCDR2 of the nanobody or the heavy-chain antibody disclosed herein.

In some embodiments, the HCDR3 of the humanized heavy-chain antibody disclosed herein comprises HCDR3 contained in a heavy-chain variable region sequence set forth in SEQ ID NO: 124 or 125, or the HCDR3 of the humanized heavy-chain antibody disclosed herein consists of HCDR3 contained in a heavy-chain variable region sequence set forth in SEQ ID NO: 124 or 125.

In some embodiments, the HCDR3 of the humanized heavy-chain antibody disclosed herein comprises HCDR3 contained in a heavy-chain variable region sequence having at least 90%, 91%, 92%, 93%, 94%, 95%, 96%, 97%, 98%, 99% or more sequence identity with a heavy-chain variable region sequence set forth in SEQ ID NO: 124 or 125, wherein preferably, the sequence difference does not exist in the CDR region; or the HCDR3 of the humanized heavy-chain antibody disclosed herein consists of HCDR3 contained in such a heavy-chain variable region sequence.

In some embodiments, the HCDR3 of the humanized heavy-chain antibody disclosed herein comprises HCDR3 contained in a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in SEQ ID NO: 124 or 125, wherein preferably, the amino acid alterations do not occur in the CDR region; or the HCDR3 of the humanized heavy-chain antibody disclosed herein consists of HCDR3 contained in such a heavy-chain variable region sequence.

In some embodiments, the HCDR3 of the humanized heavy-chain antibody disclosed herein comprises HCDR3 selected from SEQ ID NO: 51 and 61, or the HCDR3 of the humanized heavy-chain antibody disclosed herein consists of HCDR3 selected from SEQ ID NO: 51 and 61.

In some embodiments, the HCDR3 of the humanized heavy-chain antibody disclosed herein comprises HCDR3 having one or more (preferably 1 to 10, more preferably 1 to 5, and most preferably 1 to 3) amino acid alterations (preferably substitution, and more preferably conservative substitution) relative to HCDR3 selected from SEQ ID NO: 51 and 61, wherein preferably, the amino acid alterations do not occur in the CDR region; or the HCDR3 of the humanized heavy-chain antibody disclosed herein consists of such HCDR3.

In some embodiments, the HCDR1 and the HCDR2 of the humanized heavy-chain antibody disclosed herein comprises HCDR1 and HCDR2 contained in a heavy-chain variable region sequence selected from SEQ ID NO: 124 and 125, or the HCDR1 and the HCDR2 of the humanized heavy-chain antibody disclosed herein consists of HCDR1 and HCDR2 contained in a heavy-chain variable region sequence selected from SEQ ID NO: 124 and 125.

In some embodiments, the HCDR1 and the HCDR2 of the humanized heavy-chain antibody disclosed herein comprises HCDR1 and HCDR2 contained in a heavy-chain variable region sequence having at least 90%, 91%, 92%, 93%, 94%, 95%, 96%, 97%, 98%, 99% or more sequence identity with a heavy-chain variable region sequence set forth in SEQ ID NO: 124 or 125, wherein preferably, the sequence difference does not exist in the CDR region; or the HCDR1 and the HCDR2 of the humanized heavy-chain antibody disclosed herein consists of HCDR1 and HCDR2 contained in such a heavy-chain variable region sequence.

In some embodiments, the HCDR1 and the HCDR2 of the humanized heavy-chain antibody disclosed herein comprise HCDR1 and HCDR2 contained in a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in SEQ ID NO: 124 or 125, wherein preferably, the amino acid alterations do not occur in the CDR region; or the HCDR1 and the HCDR2 of the humanized heavy-chain antibody disclosed herein consist of HCDR1 and HCDR2 contained in such a heavy-chain variable region sequence.

In some embodiments, the HCDR1 of the humanized heavy-chain antibody disclosed herein comprises HCDR1 set forth in SEQ ID NO: 7 or 20, or the HCDR1 of the humanized heavy-chain antibody disclosed herein consists of HCDR1 set forth in SEQ ID NO: 7 or 20.

In some embodiments, the HCDR1 of the humanized heavy-chain antibody disclosed herein comprises HCDR1 having one or more (preferably 1 to 10, more preferably 1 to 5, and most preferably 1 to 3) amino acid alterations (preferably substitution, and more preferably conservative substitution) relative to HCDR1 set forth in SEQ ID NO: 7 or 20, or the HCDR1 of the humanized heavy-chain antibody disclosed herein consists of such HCDR1.

In some embodiments, the HCDR2 of the humanized heavy-chain antibody disclosed herein comprises HCDR2 set forth in SEQ ID NO: 29 or 42, or the HCDR2 of the humanized heavy-chain antibody disclosed herein consists of HCDR2 set forth in SEQ ID NO: 29 or 42.

In some embodiments, the HCDR2 of the humanized heavy-chain antibody disclosed herein comprises HCDR2 having one or more (preferably 1 to 10, more preferably 1 to 5, and most preferably 1 to 3) amino acid alterations (preferably substitution, and more preferably conservative substitution) relative to HCDR2 set forth in SEQ ID NO: 29 or 42, or the HCDR2 of the humanized heavy-chain antibody disclosed herein consists of such HCDR2.

In some embodiments, the humanized heavy-chain antibody disclosed herein comprises a combination of HCDR1 set forth in SEQ ID NO: 7, HCDR2 set forth in SEQ ID NO: 29, and HCDR3 set forth in SEQ ID NO: 51.

In some embodiments, the humanized heavy-chain antibody disclosed herein comprises a combination of HCDR1 set forth in SEQ ID NO: 20, HCDR2 set forth in SEQ ID NO: 42, and HCDR3 set forth in SEQ ID NO: 61.

In some embodiments, the heavy-chain variable region sequence of the humanized heavy-chain antibody disclosed herein comprises a heavy-chain variable region sequence set forth in SEQ ID NO: 124 or 125, or the heavy-chain variable region sequence of the humanized heavy-chain antibody disclosed herein consists of a heavy-chain variable region sequence set forth in SEQ ID NO: 124 or 125.

In some embodiments, the heavy-chain variable region sequence of the humanized heavy-chain antibody disclosed herein comprises a heavy-chain variable region sequence having at least 90%, 91%, 92%, 93%, 94%, 95%, 96%, 97%, 98%, 99% or more sequence identity with a heavy-chain variable region sequence set forth in SEQ ID NO: 124 or 125, wherein preferably, the sequence difference does not exist in the CDR region; or the heavy-chain variable region sequence of the humanized heavy-chain antibody disclosed herein consists of such a heavy-chain variable region sequence.

In some embodiments, the heavy-chain variable region sequence of the humanized heavy-chain antibody disclosed herein comprises a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in SEQ ID NO: 124 or 125, wherein preferably, the amino acid alterations do not occur in the CDR region; or the heavy-chain variable region sequence of the humanized heavy-chain antibody disclosed herein consists of such a heavy-chain variable region sequence.

In some embodiments, the humanized heavy-chain antibody disclosed herein comprises a humanized heavy-chain antibody sequence set forth in SEQ ID NO: 116 or 117, or the humanized heavy-chain antibody disclosed herein consists of one, two or more humanized heavy-chain antibody sequences set forth in SEQ ID NO: 116 or 117.

In some embodiments, the humanized heavy-chain antibody disclosed herein comprises a humanized heavy-chain antibody sequence having at least 90%, 91%, 92%, 93%, 94%, 95%, 96%, 97%, 98%, 99% or more sequence identity with a humanized heavy-chain antibody sequence set forth in SEQ ID NO: 116 or 117, wherein preferably, the sequence difference does not exist in the CDR region; or the humanized heavy-chain antibody disclosed herein consists of one, two or more humanized heavy-chain antibody sequences described above.

In some embodiments, the humanized heavy-chain antibody disclosed herein comprises a humanized heavy-chain antibody sequence having one or more (preferably 1 to 10, more preferably 1 to 5, and most preferably 1 to 3) amino acid alterations (preferably substitution, and more preferably conservative substitution) relative to a humanized heavy-chain antibody sequence set forth in SEQ ID NO: 116 or 117, wherein preferably, the amino acid alteration does not occur in the CDR region; or the humanized heavy-chain antibody disclosed herein consists of one, two or more humanized heavy-chain antibody sequences described above.

In some embodiments, the heavy-chain antibody or the humanized heavy-chain antibody disclosed herein comprises an Fc fragment and any one of the above-mentioned heavy-chain variable regions, and preferably, the Fc fragment comprises or consists of one of the following sequences (a)-(d):

(a) an Fc fragment of human IgG1;
(b) an Fc fragment set forth in SEQ ID NO: 121;
(c) an Fc fragment having at least 90%, 91%, 92%, 93%, 94%, 95%, 96%, 97%, 98%, 99% or more sequence identity with an Fc fragment set forth in SEQ ID NO: 121; or
(d) an Fc fragment having one or more (preferably 1 to 10, more preferably 1 to 5, and most preferably 1 to 3) amino acid alterations (preferably substitution, and more preferably conservative substitution) relative to an Fc fragment set forth in SEQ ID NO: 121.

In a preferred embodiment, the heavy-chain antibody or the humanized heavy-chain antibody disclosed herein comprises two Fc sequences selected from the above-mentioned sequences (a)-(d).

In a more preferred embodiment, there are inter-chain disulfide bonds between two Fc sequences selected from (a)-(d) in the same heavy-chain antibody or humanized heavy-chain antibody disclosed herein.

In the most preferred embodiment, there are two inter-chain disulfide bonds between two Fc sequences selected from (a)-(d) in the same heavy-chain antibody or humanized heavy-chain antibody disclosed herein. The two inter-chain disulfide bonds are formed between amino acid residues C in a CPCC sequence contained in the heavy-chain antibody or the humanized heavy-chain antibody disclosed herein. The CPPC sequence is a sequence linking a nanobody and Fc in the heavy-chain antibody or humanized heavy-chain antibody disclosed herein.

In another aspect, the present invention provides an antibody in a polymeric form that specifically binds to a GITR and efficiently activates the NF-κB signaling pathway downstream of the GITR (i.e., the antibody in a polymeric form disclosed herein), and HCDR3 of the antibody in a polymeric form comprises or consists of the HCDR3 of the antibody or the antigen-binding fragment thereof disclosed herein.

In some embodiments, the HCDR3 of the antibody in a polymeric form disclosed herein comprises or consists of HCDR3 of the nanobody, the heavy-chain antibody or the humanized heavy-chain antibody disclosed herein, and preferably, the HCDR1 and the HCDR2 of the antibody in a polymeric form disclosed herein respectively comprise or consist of HCDR1 and HCDR2 of the nanobody, the heavy-chain antibody or the humanized heavy-chain antibody disclosed herein.

In a preferred embodiment, the antibody in a polymeric form disclosed herein is a polymeric form of the nanobody, the heavy-chain variable region of the heavy-chain antibody, or the heavy-chain variable region of the humanized heavy-chain antibody disclosed herein, preferably, a tetrameric or hexameric form of the nanobody, the heavy-chain variable region of the heavy-chain antibody, or the heavy-chain variable region of the humanized heavy-chain antibody disclosed herein, and most preferably a tetrameric form of the nanobody, the heavy-chain variable region of the heavy-chain antibody, or the heavy-chain variable region of the humanized heavy-chain antibody disclosed herein.

By producing an antibody in a polymeric form from the nanobody, the heavy-chain variable region of the heavy-chain antibody, or the heavy-chain variable region of the humanized heavy-chain antibody disclosed herein, the NF-κB signaling pathway downstream of the GITR can be more effectively activated, and the half-life of the nanobody, the heavy-chain antibody, or the humanized heavy-chain antibody disclosed herein in vivo can be prolonged appropriately.

In some embodiments, the HCDR3 in the heavy-chain variable region of the antibody in a polymeric form disclosed herein comprises an HCDR3 sequence contained in a heavy-chain variable region sequence set forth in SEQ ID NO: 125, or the HCDR3 in the heavy-chain variable region of the antibody in a polymeric form disclosed herein consists of an HCDR3 sequence contained in a heavy-chain variable region sequence set forth in SEQ ID NO: 125.

In some embodiments, the HCDR3 in the heavy-chain variable region of the antibody in a polymeric form disclosed herein comprises HCDR3 contained in a heavy-chain variable region sequence having at least 90%, 91%, 92%, 93%, 94%, 95%, 96%, 97%, 98%, 99% or more sequence identity with a heavy-chain variable region sequence set forth in SEQ ID NO: 125, wherein preferably, the sequence difference does not exist in the CDR region; or the HCDR3 in the heavy-chain variable region of the antibody in a polymeric form disclosed herein consists of such HCDR3.

In some embodiments, the HCDR3 in the heavy-chain variable region of the antibody in a polymeric form disclosed herein comprises HCDR3 contained in a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in SEQ ID NO: 125, wherein preferably, the amino acid alterations do not occur in the CDR region; or the HCDR3 in the heavy-chain variable region of the antibody in a polymeric form disclosed herein consists of such HCDR3.

In some embodiments, the HCDR3 in the heavy-chain variable region of the antibody in a polymeric form disclosed herein comprises an HCDR3 sequence set forth in SEQ ID NO: 61, or the HCDR3 in the heavy-chain variable region of the antibody in a polymeric form disclosed herein consists of an HCDR3 sequence set forth in SEQ ID NO: 61.

In some embodiments, the HCDR3 in the heavy-chain variable region of the antibody in a polymeric form disclosed herein comprises an HCDR3 sequence having one or more (preferably 1 to 10, more preferably 1 to 5, and most preferably 1 to 3) amino acid alterations (preferably substitution, and more preferably conservative substitution) relative to an HCDR3 sequence set forth in SEQ ID NO: 61, or the HCDR3 in the heavy-chain variable region of the antibody in a polymeric form disclosed herein consists of such HCDR3.

In some embodiments, the HCDR1 and the HCDR2 in the heavy-chain variable region of the antibody in a polymeric form disclosed herein comprise HCDR1 and HCDR2 contained in a heavy-chain variable region sequence set forth in SEQ ID NO: 125, or the HCDR1 and the HCDR2 in a heavy-chain variable region of the antibody in a polymeric form disclosed herein consist of HCDR1 and HCDR2 contained in a heavy-chain variable region sequence set forth in SEQ ID NO: 125.

In some embodiments, the HCDR1 and the HCDR2 in the heavy-chain variable region of the antibody in a polymeric form disclosed herein comprise HCDR1 and HCDR2 contained in a heavy-chain variable region sequence having at least 90%, 91%, 92%, 93%, 94%, 95%, 96%, 97%, 98%, 99% or more sequence identity with a heavy-chain variable region sequence set forth in SEQ ID NO: 125, wherein preferably, the sequence difference does not exist in the CDR region; or the HCDR1 and the HCDR2 in the heavy-chain variable region of the antibody in a polymeric form disclosed herein consist of such HCDR1 and HCDR2.

In some embodiments, the HCDR1 and the HCDR2 in the heavy-chain variable region of the antibody in a polymeric form disclosed herein comprise HCDR1 and HCDR2 contained in a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in SEQ ID NO: 125, wherein preferably, the amino acid alterations do not occur in the CDR region; or the HCDR1 and the HCDR2 in the heavy-chain variable region of the antibody in a polymeric form disclosed herein consist of such HCDR1 and HCDR2.

In some embodiments, the HCDR1 in the heavy-chain variable region of the antibody in a polymeric form disclosed herein comprises an HCDR1 sequence set forth in SEQ ID NO: 20, or the HCDR1 in a heavy-chain variable region of the antibody in a polymeric form disclosed herein consists of an HCDR1 sequence set forth in SEQ ID NO: 20.

In some embodiments, the HCDR1 in the heavy-chain variable region of the antibody in a polymeric form disclosed herein comprises an HCDR1 sequence having one or more (preferably 1 to 10, more preferably 1 to 5, and most preferably 1 to 3) amino acid alterations (preferably substitution, and more preferably conservative substitution) relative to an HCDR1 sequence set forth in SEQ ID NO: 20, or the HCDR1 in the heavy-chain variable region of the antibody in a polymeric form disclosed herein consists of such HCDR1.

In some embodiments, the HCDR2 in the heavy-chain variable region of the antibody in a polymeric form disclosed herein comprises an HCDR2 sequence set forth in SEQ ID NO: 42, or the HCDR2 in the heavy-chain variable region of the antibody in a polymeric form disclosed herein consists of an HCDR2 sequence set forth in SEQ ID NO: 42.

In some embodiments, the HCDR2 in the heavy-chain variable region of the antibody in a polymeric form disclosed herein comprises an HCDR2 sequence having one or more (preferably 1 to 10, more preferably 1 to 5, and most preferably 1 to 3) amino acid alterations (preferably substitution, and more preferably conservative substitution) relative to an HCDR2 sequence set forth in SEQ ID NO: 42, or the HCDR2 in the heavy-chain variable region of the antibody in a polymeric form disclosed herein consists of such HCDR2.

In some embodiments, the heavy-chain variable region of the antibody in a polymeric form disclosed herein comprises a combination of HCDR1 set forth in SEQ ID NO: 20, HCDR2 set forth in SEQ ID NO: 42, and HCDR3 set forth in SEQ ID NO: 61.

In some embodiments, the heavy-chain variable region of the antibody in a polymeric form disclosed herein comprises a heavy-chain variable region sequence set forth in SEQ ID NO: 125, or the heavy-chain variable region of the antibody in a polymeric form disclosed herein consists of a heavy-chain variable region sequence set forth in SEQ ID NO: 125.

In some embodiments, the heavy-chain variable region of the antibody in a polymeric form disclosed herein comprises a heavy-chain variable region sequence having at least 90%, 91%, 92%, 93%, 94%, 95%, 96%, 97%, 98%, 99% or more sequence identity with a heavy-chain variable region sequence set forth in SEQ ID NO: 125, wherein preferably, the sequence difference does not exist in the CDR region; or the heavy-chain variable region of the antibody in a polymeric form disclosed herein consists of such a heavy-chain variable region sequence.

In some embodiments, the heavy-chain variable region of the antibody in a polymeric form disclosed herein comprises a heavy-chain variable region sequence having one or more (preferably 1 to 10, more preferably 1 to 5, and most preferably 1 to 3) amino acid alterations (preferably substitution, and more preferably conservative substitution) relative to a heavy-chain variable region sequence set forth in SEQ ID NO: 125, wherein preferably, the amino acid alterations do not occur in the CDR region; or the heavy-chain variable region of the antibody in a polymeric form disclosed herein consists of such a heavy-chain variable region sequence.

In some embodiments, the antibody in a polymeric form disclosed herein comprises any sequence selected from SEQ ID NOs: 118-120, or the antibody in a polymeric form disclosed herein consists of two, three or more identical sequences selected from SEQ ID NOs: 118-120.

In some embodiments, the antibody in a polymeric form disclosed herein comprises a sequence having at least 90%, 91%, 92%, 93%, 94%, 95%, 96%, 97%, 98%, 99% or more sequence identity with a sequence set forth in any one of SEQ ID NOs: 118-120, wherein preferably, the sequence difference does not exist in the CDR region; or the antibody in a polymeric form disclosed herein consists of two, three or more identical sequences described above.

In some embodiments, the antibody in a polymeric form disclosed herein comprises a sequence having one or more (preferably 1 to 10, more preferably 1 to 5, and most preferably 1 to 3) amino acid alterations (preferably substitution, and more preferably conservative substitution) relative to a sequence set forth in any one of SEQ ID NOs: 118-120, wherein preferably, the amino acid alterations do not occur in the CDR region; or the antibody in a polymeric form disclosed herein consists of two, three or more identical sequences described above.

In some embodiments, a nanobody, a heavy-chain variable region of the heavy-chain antibody, or a heavy-chain variable region of the humanized heavy-chain antibody (referred to as "heavy-chain variable region disclosed herein") in the antibody in a polymeric form disclosed herein is linked to the humanized heavy-chain antibody disclosed herein.

In a preferred embodiment, the nanobody, the heavy-chain variable region of the heavy-chain antibody, or the heavy-chain variable region of the humanized heavy-chain antibody in the antibody in a polymeric form disclosed herein is linked to C-terminus of the humanized heavy-chain antibody disclosed herein; or the nanobody, the heavy-chain variable region of the heavy-chain antibody, or the heavy-chain variable region of the humanized heavy-chain antibody disclosed herein is linked to N-terminus of the humanized heavy-chain antibody disclosed herein.

In a more preferred embodiment, the antibody in a polymeric form disclosed herein contains two identical nanobodies, heavy-chain variable regions of the heavy-chain antibody, or heavy-chain variable regions of the humanized heavy-chain antibody disclosed herein that are respectively linked to C-termini of two identical humanized heavy-chain antibodies disclosed herein or N-termini of two identical humanized heavy-chain antibodies disclosed herein.

In a most preferred embodiment, the antibody in a polymeric form disclosed herein is a tetramer containing four identical nanobodies, heavy-chain variable regions of the heavy-chain antibody, or heavy-chain variable regions of the humanized heavy-chain antibody disclosed herein, and the tetramer comprises two identical chains that each contains one humanized heavy-chain antibody disclosed herein and one nanobody, heavy-chain variable region of the heavy-chain antibody, or heavy-chain variable region of the humanized heavy-chain antibody. That is, the antibody in a polymeric form disclosed herein contains two identical chains (a first chain and a second chain that are exactly the same), and each chain contains only one humanized heavy-chain antibody disclosed herein and one additional nanobody, heavy-chain variable region of the heavy-chain antibody, or heavy-chain variable region of the humanized heavy-chain antibody disclosed herein, wherein, the nanobody, heavy-chain variable region of the heavy-chain antibody, or heavy-chain variable region of the humanized heavy-chain antibody disclosed herein contained in the first chain is the same as the nanobody, heavy-chain variable region of the heavy-chain antibody, or heavy-chain variable region of the humanized heavy-chain antibody disclosed herein contained in the second chain, and the humanized heavy-chain antibody contained in the first chain is the same as the humanized heavy-chain antibody contained in the second chain. There may also be inter-chain disulfide bonds between these two identical chains. The inter-chain disulfide bonds are two inter-chain disulfide bonds formed between amino acid residues C in sequences (e.g., CPPC sequences) linking a heavy-chain variable region and Fc in the humanized heavy-chain antibody of each chain. That is, inter-chain disulfide bonds are formed between amino acid residues C in a sequence that is between a heavy-chain variable region and Fc in the humanized heavy-chain antibody of the first chain and amino acid residues C in a sequence that is between a heavy-chain variable region and Fc in the humanized heavy-chain antibody of the second chain.

In some embodiments, the nanobody, the heavy-chain variable region of the heavy-chain antibody, or the heavy-chain variable region of the humanized heavy-chain antibody disclosed herein in the antibody in a polymeric form disclosed herein is linked to the humanized heavy-chain antibody disclosed herein via a linker peptide. The linker peptide is preferably, a flexible linker peptide, and more preferably, a linker peptide having an amino acid sequence of (G4S)n (n is an integer of 0-7).

The present invention provides nanobodies, heavy-chain antibodies, humanized heavy-chain antibodies, and antibodies in a tetrameric form that specifically bind to a GITR (e.g., human GITR) as isolated and characterized in Examples. The amino acid sequences and nucleotide sequences of the exemplary antibodies disclosed herein are listed in Table B below. Among the amino acid sequences of antibodies, the sequences shown in bold and italic from N-terminus to C-terminus are exemplary CDR sequences (the following exemplary CDR sequences are determined by any one of the various methods known in the art for determining the precise amino acid sequence boundary of CDR or by a combination thereof, for example, they can be determined according to a method described above with reference to other factors, such as conservativeness).

TABLE B

Amino acid sequences and nucleotide sequences of exemplary nanobodies, amino acid sequences of heavy-chain antibodies, amino acid sequences of humanized heavy-chain antibodies, and amino acid sequences of antibodies in a tetramer form, and SEQ ID NOs. thereof

| Nanobody No. | Amino acid sequence | Nucleotide sequence |
|---|---|---|
| NB01 | QVQLQESGGGLVQPGG SLRLSCTAS*GLTFDDYA*MGWFRQAPGKGREGVS LI*TWSGSSTY*YADSVKG RFTVSRDTATNTLVLQM NSLKPEDTAMYYCAA*D PRSGGYYSSPPPPAVYRY LRF*WGQGTQVTVSS | CAGGTGCAGCTGCAGGAGTCTGGAGGAGGCTTGGTGCAGCCGGGGG GGTCTCTGAGACTCTCCTGTACAGCCTCTGGATTGACTTTTGATGATT ATGCCATGGGCTGGTTCCGCCAGGCTCCAGGGAAGGGGCGCGAGGGT GTCTCACTTATTACCTGGAGTGGTAGTAGCACATACTATGCGGACTCC GTGAAGGGCCGATTCACCGTCTCCAGAGACACCGCCACGAATACGCT GGTTCTACAAATGAACAGCCTGAAACCAGAGGATACGGCCATGTATT ACTGTGCGGCAGATCCACGTAGTGGTGGTTACTACTCCAGCCCCCCTC CCCCCGCTGTGTACAGGTATCTCCGATTTTGGGGCCAGGGCACCCAG GTCACCGTCTCCTCA |
| Sequence No. | SEQ ID NO: 64 | SEQ ID NO: 86 |
| NB02 | QVQLQESGGGSVQAGG SLRLSCAAS*RDTYTRY*F MGWFRQTPGKEGEGVA *VLLPGDDYTF*YADSVK GRFTITQDSAKNTVYLQ MNSLKPEDTAMYYCAA *DVTVGSRWSQASNYNY* WGQGTQVTVSS | CAGGTGCAGCTGCAGGAGTCTGGAGGAGGCTCGGTGCAGGCTGGAG GGTCTCTGAGACTCTCCTGTGCAGCCTCTAGAGACACCTACACGCGCT ACTTTATGGGCTGGTTCCGCCAGACTCCAGGGAAGGAGGGCGAGGGG GTCGCAGTCCTTCTACCTGGCGGTGATTATACATTCTATGCCGACTCC GTGAAGGGCCGGTTCACCATCACCCAAGACAGCGCCAAGAACACGGT GTATCTGCAAATGAACAGCCTGAAACCTGAGGACACTGCCATGTACT ACTGTGCGGCAGATGTAACGGTCGGTAGTAGGTGGTCTCAAGCTTCG AATTATAACTACTGGGGCCAGGGGACCCAGGTCACCGTCTCCTCA |
| Sequence No. | SEQ ID NO: 65 | SEQ ID NO: 87 |
| NB03 | QVQLQESGGGSVQAGG SLRLSCAAS*GYTYSGYC* MGWFRQAPGKEHEGVA *SIVSGLGRP*YYADSVKG RFTISQDNAKNTVYLQM NSLKPEDTAMYYCAA*E WATKLCSEIPATEWDY* WGQGTQVTVSS | CAGGTGCAGCTGCAGGAGTCTGGAGGAGGCTCGGTGCAGGCTGGAG GGTCTCTGAGACTCTCCTGTGCAGCCTCTGGATACACCTACAGTGGCT ACTGTATGGGCTGGTTCCGCCAGGCTCCAGGGAAGGAGCACGAGGGG GTCGCAAGTATTGTTTCTGGTCTTGGTAGACCATACTATGCCGATTCC GTGAAGGGCCGATTCACCATCTCCCAAGACAACGCCAAGAACACGGT GTATCTGCAAATGAACAGCCTGAAACCTGAGGACACTGCCATGTACT ACTGTGCGGCAGAATGGGCGACGAAACTCTGTTCTGAGATACCTGCC ACCGAGTGGGACTACTGGGGCCAGGGGACCCAGGTCACCGTCTCCTC A |
| Sequence No. | SEQ ID NO: 66 | SEQ ID NO: 88 |
| NB04 | QVQLQESGGGSVQAGG SLRLSCTAS*GFTVDDSG* MGWYRQAPGNECELV*S TISSDGSTY*YADSVKGR FTISQDNAKNTVYLQMN SLKPEDTAVYYCAA*PRV GVGWVRPCDYEYNY*WG QGTQVTVSS | CAGGTGCAGCTGCAGGAGTCTGGGGGAGGCTCGGTGCAGGCTGGAG GGTCTCTGAGACTCTCCTGTACAGCCTCTGGATTCACTGTTGACGATT CTGGCATGGGCTGGTACCGCCAGGCTCCAGGGAATGAGTGCGAGTTG GTCTCAACTATTAGTAGTGATGGTAGCACATACTATGCAGACTCCGTG AAGGGCCGATTCACCATCTCCCAAGACAACGCCAAGAACACGGTGTA TCTGCAAATGAACAGCCTGAAACCTGAGGACACGGCCGTGTATTACT GTGCGGCACCCCGGGTCGGTGTGGGTTGGGTACGTCCCTGTGATTATG AGTATAACTACTGGGGCCAGGGGACCCAGGTCACCGTCTCCTCA |
| Sequence No. | SEQ ID NO: 67 | SEQ ID NO: 89 |
| NB05 | QVQLQESGGGLVQPGG SLRLSCAAS*GFTFSNKV* MSWVRQAPGKGFEWVS SI*ARGGDWTT*YADSVEG RFTISRDNAKNTLYLQL NSLKTEDTAMYYCAQ*A ENWKTP*PGQGTQVTVSS | CAGGTGCAGCTGCAGGAGTCTGGGGGAGGCTTGGTGCAGCCTGGGGG GTCTCTGAGACTCTCCTGTGCAGCCTCTGGATTCACCTTCAGTAACAA AGTCATGAGCTGGGTCCGCCAGGCTCCAGGGAAGGGATTCGAGTGGG TCTCAAGTATTGCGAGAGGTGGTGACTGGACAACCTATGCAGACTCC GTGGAGGGCCGATTCACCATCTCCAGAGACAACGCCAAGAACACTCT GTATCTGCAATTGAACAGCCTGAAAACTGAGGACACGGCCATGTATT ACTGTGCCCAAGCTGAGAATTGGAAAACCCCGCCGGGCCAGGGGACC CAGGTCACCGTCTCCTCA |
| Sequence No. | SEQ ID NO: 68 | SEQ ID NO: 90 |
| NB06 | QVQLQESGGGSVQAGG SLRLSCAAS*GYAYTRNC* MGWFRQAPGKEREEVA TI*NLGGGSTY*YADSVKG | CAGGTGCAGCTGCAGGAGTCTGGGGGAGGCTCGGTGCAGGCTGGAG GGTCTCTGAGACTCTCCTGTGCAGCCTCTGGATACGCCTACACTCGCA ACTGCATGGGCTGGTTCCGCCAGGCTCCAGGGAAGGAGCGCGAGGAA GTCGCAACTATTAATCTTGGTGGTGGTAGCACATACTATGCCGACTCC |

TABLE B-continued

Amino acid sequences and nucleotide sequences of exemplary nanobodies, amino acid sequences of heavy-chain antibodies, amino acid sequences of humanized heavy-chain antibodies, and amino acid sequences of antibodies in a tetramer form, and SEQ ID NOs. thereof

| | | |
|---|---|---|
| | RFAISQDNAKNTVYLQ<br>MNNLKPEDTAMYYCAA<br>*IAQYGGSLCSNFGWYNL*<br>WGQGTQVTVSS | GTGAAGGGCCGATTCGCCATCTCCCAAGACAACGCCAAGAACACGGT<br>GTATCTGCAAATGAACAACCTGAAACCTGAGGACACTGCCATGTACT<br>ACTGTGCGGCGATCGCTCAGTACGGTGGTAGCTTGTGCAGCAATTTCG<br>GATGGTATAACTTGTGGGGCCAGGGGACCCAGGTCACCGTCTCCTCA |
| Sequence No. | SEQ ID NO: 69 | SEQ ID NO: 91 |
| NB07 | QVQLQESGGGLVQAGG<br>SLKLSCTVS*GFAFGSSH*<br>MSWVRRAPGKGLEWVS<br>TI*HSGGGFGD*YANSVQ<br>GRFTISRDVAKNTLYLQ<br>MNSLKPEDTAIYYCAL*A*<br>*TDWRKP*PGQGTQVTVSS | CAGGTGCAGCTGCAGGAGTCTGGAGGAGGCTTGGTGCAGGCAGGGG<br>GGTCTCTGAAGCTCTCCTGTACAGTCTCTGGATTCGCATTCGGTTCCT<br>CCCACATGAGCTGGGTCCGCCGGGCTCCAGGGAAGGGGCTCGAGTGG<br>GTCTCAACTATTCATAGCGGTGGTGGCTTTGGCGACTATGCGAACTCC<br>GTGCAGGGCCGATTCACCATCTCCAGAGACGTCGCCAAGAACACGCT<br>GTATCTGCAAATGAACAGCCTGAAACCTGAAGACACGGCCATATATT<br>ACTGTGCGCTCGCGACGGATTGGAGAAAGCCCCCCGGCCAGGGGACC<br>CAGGTCACCGTCTCCTCA |
| Sequence No. | SEQ ID NO: 70 | SEQ ID NO: 92 |
| NB08 | QVQLQESGGGSVQAGG<br>SLRLSCAAS*GYTSSRKYI*<br>GWFRQAPGKQREWVA<br>GI*DTGAGGTC*TIASVQG<br>RFTISQDVAKNTLYLQID<br>SLKPEDTAVYYCAA*DW*<br>*VRGGFCSGDADFRY*WG<br>QGTQVTVSS | CAGGTGCAGCTGCAGGAGTCTGGGGGAGGGTCGGTGCAGGCTGGAG<br>GGTCTCTGAGACTCTCCTGTGCAGCCTCTGGATACACCTCCAGTAGGA<br>AATACATAGGATGGTTCCGACAGGCTCCAGGGAAGCAGCGCGAGTGG<br>GTCGCAGGTATTGATACTGGTGCTGGTGGCACATGCACGATCGCCTC<br>AGTGCAGGGCCGGTTCACCATCTCCCAAGACGTCGCCAAGAACACGT<br>TGTATCTCCAAATAGACAGCCTGAAACCTGAAGACACTGCCGTATAC<br>TACTGTGCGGCAGATTGGGTCCGGGTGGTTTTTGCTCAGGCGATGCT<br>GACTTTCGTTATTGGGGCCAGGGGACCCAGGTCACCGTCTCCTCA |
| Sequence No. | SEQ ID NO: 71 | SEQ ID NO: 93 |
| NB09 | QVQLQESGGGLVQPGG<br>SLRLSCGAS*GFTFSST*A<br>MWWFRQAPGKGLEWV<br>SSI*TSDVSGTY*YADSVQG<br>RFTISRDNGKNTVYLQM<br>NSLRSEDTALYYCAT*SC*<br>*GFSGGTWSCKY*RGQGT<br>QVTVSS | CAGGTGCAGCTGCAGGAGTCTGGGGGAGGCTTGGTGCAGCCTGGGGG<br>GTCTCTGAGACTCTCCTGTGGATTCACCTTCAGTAGCAC<br>CGCCATGTGGTGGTTCCGCCAGGCTCCAGGGAAGGGGCTGGAGTGGG<br>TGTCCAGTATTACCAGTGATGTTAGTGGCACGTACATGCAGACTCCG<br>TCCAGGGCCGATTCACCATCTCCAGAGACAACGGCAAGAACACGGTG<br>TATCTGCAAATGAACAGCCTGAGATCTGAGGACACGGCCCTGTATTA<br>TTGTGCCACCTCGTGTGGGTTTAGTGGTGGTACGTGGTCTTGTAAATA<br>CAGGGGCCAGGGGACCCAGGTCACCGTCTCCTCA |
| Sequence No. | SEQ ID NO: 72 | SEQ ID NO: 94 |
| NB10 | QVQLQESGGGLVQPGG<br>SLRLSCAAS*GFAFGSS*H<br>MSWVRRAPGKGLEWVS<br>TIH*SGGGFGD*YANSVQG<br>RFTISRDVAKNTLYLQM<br>NSLKPEDTAIYYCAL*AT*<br>*DWRKP*PGQGTQVTVSS | CAGGTGCAGCTGCAGGAGTCTGGGGGAGGCTTGGTGCAGCCTGGGGG<br>GTCTCTGAGACTCTCCTGTGGATTCGCATTCGGTTCCTC<br>CCACATGAGCTGGGTCCGCCGGGCTCCAGGGAAGGGGCTCGAGTGG<br>TCTCAACTATTCATAGCGGTGGTGGCTTTGGCGACTATGCGAACTCC<br>TGCAGGGCCGATTCACCATCTCCAGAGACGTCGCCAAGAACACGCTG<br>TATCTGCAAATGAACAGCCTGAAACCTGAAGACACGGCCATATATTA<br>CTGTGCGCTCGCGACGGATTGGAGAAAGCCCCCCGGCCAGGGGACCC<br>AGGTCACCGTCTCCTCA |
| Sequence No. | SEQ ID NO: 73 | SEQ ID NO: 95 |
| NB 11 | QVQLQESGGGSVQTGG<br>SLRLSCTAS*GFTFDAA*D<br>MGWYRQAPGNECELVS<br>II*SSDGSTY*YADSVKGRF<br>TISQDNAKNTVYLQMNS<br>LKPEDTAVYYCAA*PRV*<br>*GVGWVRPCDYEYNY*WG<br>QGTQVTVSS | CAGGTGCAGCTGCAGGAGTCTGGAGGAGGCTCGGTGCAGACTGGAG<br>GGTCTCTGAGACTCTCCTGTACAGCCTCTGGATTCACTTTTGATGCGG<br>CTGACATGGGCTGGTACCGCCAGGCTCCAGGGAATGAGTGCGAGTTG<br>GTCTCAATTATTAGTAGTGATGGTAGTACATACTATGCCGACTCCGTG<br>AAGGGCCGATTCACCATCTCCAAGACAACGCCAAGAACACGGTGTA<br>TCTGCAAATGAACAGCCTGAAACCTGAGGACACGGCCGTGTATTACT<br>GTGCGGCACCCCGGGTCGGTGTGGGTTGGGTACGTCCCTGTGACTAT<br>GAGTATAACTACTGGGGCCAGGGGACCCAGGTCACCGTCTCCTCA |
| Sequence No. | SEQ ID NO: 74 | SEQ ID NO: 96 |
| NB12 | QVQLQESGGGSVQAGG<br>SLRLSCAAS*RDTYTRYF*<br>MGWFRQTPGKEPEGVA<br>VL*LPGGAYTF*YADSVK<br>GRFTITQDSAKNTVYLQ<br>MNSLKPEDTAMYYCAA<br>*DVTVGSRWSQASNYNY*<br>WGQGTQVTVSS | CAGGTGCAGCTGCAGGAGTCTGGGGGAGGCTCGGTGCAGGCTGGAG<br>GGTCTCTGAGACTCTCCTGTGCAGCCTCTAGAGACACCTACACGCGCT<br>ACTTTATGGGCTGGTTCCGCCAGACTCCAGGGAAGGAGCCCGAGGTG<br>GTCGCAGTCCTTCTACCTGGCGGTGCTTACACATTCTATGCCGACTCC<br>GTGAAGGGCCGGTTCACCATCACCCAAGACAGCGCCAAGAACACGGT<br>GTATCTGCAAATGAACAGCCTGAAACCTGAGGACACTGCCATGTACT<br>ACTGTGCGGCAGATGTCACGGTCGGTAGTAGGTGGTCTCAAGCTTCG<br>AACTATAACTACTGGGGCCAGGGGACCCAGGTCACCGTCTCCTCA |
| Sequence No. | SEQ ID NO: 75 | SEQ ID NO: 97 |
| NB13 | QVQLQESGGGSVQAGG<br>SLRLSCTASS*NTGR*MGW<br>FRQAPGKEREGVTAVD<br>*NFGRTN*YAKYVKGRFTI | CAGGTGCAGCTGCAGGAGTCTGGGGGAGGCTCGGTGCAGGCTGGAG<br>GGTCTCTGAGACTCTCCTGTACAGCCTCTAGCAACACCGGCAGGATG<br>GGCTGGTTCCGCCAGGCTCCAGGGAAAGAGCGCGAGGGGTCACAG<br>CGGTTGATAATTTGGTAGGACAAACTACGCGAAGTACGTGAAGGGC |

TABLE B-continued

Amino acid sequences and nucleotide sequences of exemplary nanobodies, amino acid sequences of heavy-chain antibodies, amino acid sequences of humanized heavy-chain antibodies, and amino acid sequences of antibodies in a tetramer form, and SEQ ID NOs. thereof

|  |  |  |
|---|---|---|
|  | SKDNAKNTLYLQMNSL KPEDTAMYYCAA*DPWG RGAALTPNEYIY*WGQGT QVTVSS | CGATTCACCATCTCCAAAGACAACGCCAAGAACACTCTGTATCTGCA AATGAACAGCCTGAAACCTGAGGACACTGCCATGTACTACTGTGCGG CGGATCCCTGGGGACGTGGTGCGGCCCTCACCCCAAATGAGTATATC TACTGGGGCCAGGGGACCCAGGTCACCGTCTCCTCA |
| Sequence No. | SEQ ID NO: 76 | SEQ ID NO: 98 |
| NB14 | QVQLQEFGGGSVQAGG SLRLSCVASG*FTFSNYC*MGWFRQDPGKEREAVA*RIFVDGSTR*YADAVKGR FTISKDNAKNTLYVQINS LKPEDTAMYYCTT*PFP WTLCVDGPGAYKY*WGQ GTQVTVSS | CAGGTGCAGCTGCAGGAGTTTGGAGGAGGCTCGGTGCAGGCTGGAGG GTCTTTGAGACTCTCCTGTGTAGCCTCTGGATTCACCTTCAGTAACTA CTGCATGGGCTGGTTCCGCCAGGATCCAGGGAAGGAGCGCGAGGCGG TCGCACGTATTTTTGTTGATGGCAGCACAAGGTACGCAGACGCCGTG AAGGGCCGATTCACCATCTCCAAGGACAACGCCAAGAACACTCTGTA TGTGCAAATCAACAGCCTGAAACCTGAGGACACTGCCATGTACTACT GTACGACACCGTTTCCCTGGACATTGTGTGTTGATGGCCCCGGCGCGT ATAAATACTGGGGCCAGGGGACCCAGGTCACCGTCTCCTCA |
| Sequence No. | SEQ ID NO: 77 | SEQ ID NO: 99 |
| NB15 | QVQLQESGGGSVQAGG SLRLSCVVFG*NIFRNYC*MAWFRQAPGKEREGVV*VIYTGGGSTY*YADSVKG RFTISQDNAKNTVYLQM NSLKHEDTAMYYCAA*D QTTRYSSDYVNVGPCDM DS*WGKGTQVTVSS | CAGGTGCAGCTGCAGGAGTCTGGGGGAGGCTCAGTGCAGGCTGGAG GGTCTCTGAGACTCTCCTGTGTAGTTTTTGGAAACATTTTCAGGAACT ACTGCATGGCCTGGTTCCGCCAGGCTCCAGGAAAGAGCGCGAGGGG GTGGTAGTTATTTATACTGGTGGTGGTAGCACATACTATGCCGACTCC GTGAAGGGCCGATTCACCATCTCCAAGACAACGTCAAGAACACGGT GTATTTGCAAATGAACAGCCTGAAACATGAGGACACTGCCATGTACT ACTGTGCCGGCAGACCAAACCACCAGATACTCGAGCGACTATGTAAAT GTCGGCCCGTGCGACATGGACAGCTGGGGCAAAGGAACCCAGGTCAC CGTCTCCTCA |
| Sequence No. | SEQ ID NO: 78 | SEQ ID NO: 100 |
| NB16 | QVQLQESGGGSVQAGG SLRLSCAAS*GYTYNKYS*WGWFRQAPGKEREGVA*GIDSDGSTS*YADSVKGR FTISKDNTKNTLYLQMN SLKPEDTAMYYCAA*SD WVSAIQAIGVLAVRPYE Y*WGQGTQVTVSS | CAGGTGCAGCTGCAGGAGTCTGGAGGAGGCTCGGTGCAGGCTGGAGG GTCTCTGAGACTCTCCTGTGCAGCCTCTGGATACACCTACAATAAAT ACTCTGGGGCTGGTTCCGCCAGGCTCCAGGGAAGGAGCGCGAGGGG GTCGCAGGAATTGACAGTGATGGTAGCACAAGCTACGCAGACTCCGT GAAGGGCCGATTCACCATCTCCAAAGACAACACCAAGAACACTCTGT ATCTGCAAATGAACAGCCTGAAACCTGAGGACACTGCCATGTACTAC TGTGCGGCATCTGATTGGGTGTCTGCTATTCAGGCTCTTGGTGTTCTG GCGGTGAGGCCGTATGAGTACTGGGGCCAGGGGACCCAGGTCACCGT CTCCTCA |
| Sequence No. | SEQ ID NO: 79 | SEQ ID NO: 101 |
| NB17 | QVQLQESGGGSAQAGG SLRLSCAAS*RYTSSSNA*MGWFRQAPGKQREWV AGS*DTGAGITC*NAASVK GRFTISQDVAKNTVYLQ MNSLKPEDTAVYYCAA *DWFRGAFCSGDADFRY*WGQGTQVTVSS | CAGGTGCAGCTGCAGGAGTCTGGAGGAGGTTCGGCGCAGGCTGGAG GGTCTCTGAGACTCTCCTGTGCAGCCTCTAGATACACCTCCAGTAGCA ACGCGATGGGATGGTTCCGACAGGCTCCAGGGAAGCAGCGCGAGTG GGTCGCAGGTAGTGATACTGGTGCTGGTATCACATGCAATGCCGCCT CAGTGAAGGGCCGGTTCACCATCTCCCAAGACGTCGCCAAGAACACG GTGTATCTCCAAATGAACAGCCTGAAACCTGAGGACACTGCCGTATA CTACTGTGCGGCAGATTGGTTCCGGGGTGCTTTTTGCTCAGGCGATGC TGACTTTCGTTATTGGGGCCAGGGGACCCAGGTCACCGTCTCCTCA |
| Sequence No. | SEQ ID NO: 80 | SEQ ID NO: 102 |
| NB18 | QVQLQESGGGSVQTGG SLRLSCAAS*GLTSTTKY*MGWFRQAPGKEREGVA GI*YISSGAT*YYDDSVKG RFTISQDNAKNTVYLHI NSLEPDDTAMYYCAA*S VLSVFRPLSSNQYHY*WG QGTQVTVSS | CAGGTGCAGCTGCAGGAGTCTGGGGGAGGCTCGGTGCAGACTGGAG GTCTCTGAGACTCTCTTGTGCAGCTTCTGGATTGACCAGTACTACTA AGTACATGGGCTGGTTCCGCCAGGCTCCAGGGAAGGAGCGCGAGGG GGTCGCAGGTATCTATATTAGTAGTGGTGCCACATACTATGACGACTC TGTGAAGGGCCGATTCACCATCTCCAAGACAACGCCAAGAACACGG TATATTTGCACATCAACAGCCTGGAACCTGATGACACCGCGATGTACT ACTGTGCGGCTTCAGTATTAAGTGTTTTCCGGCCCTATCTAGCAACC AATATCACTACTGGGGTCAGGGGACCCAGGTCACCGTCTCCTCA |
| Sequence No. | SEQ ID NO: 81 | SEQ ID NO: 103 |
| NB19 | QVQLQESGGGSVQAGG SLRLSCAAS*GFTYSYNC*MAWFRQAPGKEREGVA AI*DSDGSTS*YADSVKGR FTISQDNAKNTLYLQMN SLKPEDTAMYYCAA*GN KKPYQLCNTDSRRYYH*WGQGTQVTVSS | CAGGTGCAGCTGCAGGAGTCTGGGGGAGGCTCGGTGCAGGCTGGAG GGTCTCTGAGACTCTCCTGTGCAGCCTCTGGATTTACCTACAGTAACT ACTGCATGGCCTGGTTCCGCCAGGCTCCAGGGAAGGAGCGCGAGGGG GTCGCAGCTATTGATAGTGATGGTAGCACAAGCTACGCAGACTCCGT GAAGGGCCGATTCACCATCTCCAAGACAACGCCAAGAACACTCTGT ATCTGCAAATGAACAGCCTGAAACCTGAGGACACTGCCATGTACTAC TGTGCGGCAGGGAACAAAAAGCCGTACCAACTGTGTAATACTGACTC CGCCGATATTACCACTGGGGCCAGGGGACCCAGGTCACCGTCTCCT CA |
| Sequence No. | SEQ ID NO: 82 | SEQ ID NO: 104 |
| NB20 | QVQLQESGGGSVQAGG SLRLSCASS*GYSRTSRW*MAWFRQAPGKEREGVA AI*YTGGSSTL*YANSMAD RVTISQDNAKNTVYLR | CAGGTGCAGCTGCAGGAGTCTGGAGGAGGCTCGGTGCAGGCTGGAG GGTCTCTGAGACTCTCCTGTGCGTCCTCTGGATACAGCCGAACTAGTC GCTGGATGGCCTGGTTCCGCCAGGCTCCAGGGAAGGAGCGCGAGGGG GTCGCAGCTATTTATACTGGTGGTAGTAGTACATTGTATGCCAACTCC ATGGCGGACCGAGTCACCATCTCCCAAGACAACGCCAAGAACACGGT |

TABLE B-continued

Amino acid sequences and nucleotide sequences of exemplary nanobodies, amino acid sequences of heavy-chain antibodies, amino acid sequences of humanized heavy-chain antibodies, and amino acid sequences of antibodies in a tetramer form, and SEQ ID NOs. thereof

|  | MNNLKPEDTAMYYCAA*DKLAGDFWLVDRWRA*WGQGTQVTVSS | GTATCTGCGAATGAACAACCTGAAACCCGAGGACACTGCCATGTACT ACTGTGCGGCAGATAAATTGGCCGGTGATTTTTGGTTGGTAGATCGG TGGCGTGCCTGGGGCCAGGGGACCCAGGTCACCGTCTCCTCA |
|---|---|---|
| Sequence No. | SEQ ID NO: 83 | SEQ ID NO: 105 |
| NB21 | QVQLQESGGGSVQAGG SLRLSCRTS*GYTNNLKS*MAWFRQAPGKEREAVA SI*HNNGGPT*YDYYAESV KGRFAISQDNAKNTLYL QMSSAKPEDTAVYYCA A*DNRFLGSGSWRLPSLY NY*WGQGTQVTVSS | CAGGTGCAGCTGCAGGAGTCTGGGGGAGGCTCGGTGCAGGCTGGAG GGTCTCTGAGACTCTCCTGTAGAACCTCTGGATACACCAACAATCTGA AGTCCATGGCCTGGTTCCGCCAGGCTCCAGGGAAGGAGCGCGAGGCC GTCGCAAGTATCCATAATAACGGAGGACCCACATACGATTACTATGC CGAATCCGTGAAGGGCCGATTCGCCATCTCCCAAGACAACGCCAAGA ACACGCTGTATCTGCAAATGAGCAGCGCGAAACCTGAGGACACTGCC GTGTATTACTGTGCGGCAGATAACCGGTTTCTGGGGTCGGGTTCGTGG CGGTTACCCAGCCTCTATAATTACTGGGGCCAGGGGACCCAGGTCAC CGTCTCCTCA |
| Sequence No. | SEQ ID NO: 84 | SEQ ID NO: 106 |
| NB22 | QVQLQESGGGSVQAGG SLRLSCAAS*GYTFTTAY*MGWFRQAPGKEREGVA AI*DSDGRTE*YADAVKG RFTISKDNAKNTLYLQM NSLKPEDTAMYYCAA*D KDDWLLLHGRSLFPSAF AY*WGQGTQVTVSS | CAGGTGCAGCTGCAGGAGTCTGGGGGAGGCTCGGTGCAGGCTGGAG GGTCTCTGAGACTCTCCTGTGCAGCCTCTGGATACACCTTCACAACTG CCTACATGGGCTGGTTCCGCCAGGCTCCAGGGAAGGAGCGCGAGGGG GTCGCAGCAATTGACAGTGACGGCCTGAACGGAATACGCAGACGCCGT GAAGGGCCGATTCACCATCTCTAAAGACAACGCCAAGAATACTCTGT ATCTGCAAATGAACAGCCTGAAACCTGAGGACACTGCCATGTACTAC TGTGCGGCAGACAAGGATGACTGGTTACTGCTACACGGCAGATCTTT ATTCCCTTCGGCCTTTGCTTACTGGGGCCAGGGGACCCAGGTCACCGT CTCCTCA |
| Sequence No. | SEQ ID NO: 85 | SEQ ID NO: 107 |

| Heavy-chain antibody | Amino acid sequence |
|---|---|
| hcIgG-02 | QVQLQESGGGSVQAGGSLRLSCAASRDTYTRYFMGWFRQTPGKEGEGVAVLLPGGDYTFYADSVKG RFTITQDSAKNTVYLQMNSLKPEDTAMYYCAADVTVGSRWSQASNYNYWGQGTQVTVSSDKTHTCP PCPAPELLGGPSVFLFPPKPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPREPQVYTLPPSRDELTKNQV SLTCLVKGFYPSDIAVEWESNGQPENNYKTTPPVLDSDGSFFLYSKLTVDKSRWQQGNVFSCSVMHEA LHNHYTQKSLSLSPGK |
| Sequence No. | SEQ ID NO: 108 |
| hcIgG-03 | QVQLQESGGGSVQAGGSLRLSCAASGYTYSGYCMGWFRQAPGKEHEGVASIVSGLGRPYYADSVKGR FTISQDNAKNTVYLQMNSLKPEDTAMYYCAAEWATKLCSEIPATEWDYWGQGTQVTVSSDKTHTCPP CPAPELLGGPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRDELTKNQVS LTCLVKGFYPSDIAVEWESNGQPENNYKTTPPVLDSDGSFFLYSKLTVDKSRWQQGNVFSCSVMHEAL HNHYTQKSLSLSPGK |
| Sequence No. | SEQ ID NO: 109 |
| hcIgG-04 | QVQLQESGGGSVQAGGSLRLSCTASGFTVDDSGMGWYRQAPGNECELVSTISSDGSTYYADSVKGRFT ISQDNAKNTVYLQMNSLKPEDTAVYYCAAPRVGVGWVRPCDYEYNYWGQGTQVTVSSDKTHTCPPC PAPELLGGPSVFLEPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDELTKNQVSLT CLVKGFYPSDIAVEWESNGQPENNYKTTPPVLDSDGSFFLYSKLTVDKSRWQQGNVFSCSVMHEALHN HYTQKSLSLSPGK |
| Sequence No. | SEQ ID NO: 110 |
| hcIgG-07 | QVQLQESGGGLVQAGGSLKLSCTVSGFAFGSSHMSWVRRAPGKGLEWVSTIHSGGGFGDYANSVQGR FTISRDVAKNTLYLQMNSLKPEDTAIYYCALATDWRKPPGQGTQVTVSSDKTHTCPPCPAPELLGGPSV FLFPPKPKDTLMISRTPEVTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCSVMHEALHNHYTQKSLSLSP GK |
| Sequence No. | SEQ ID NO: 111 |
| hcIgG-09 | QVQLQESGGGLVQPGGSLRLSCGASGFTFSSTAMWWFRQAPGKGLEWVSSITSDVSGTYYADSVQGR FTISRDNGKNTVYLQMNSLRSEDTALYYCATSCGFSGGTWSCKYRGQGTQVTVSSDKTHTCPPCPAPE LLGGPSVFLFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSRDELTKNQVSLTCLV KGFYPSDIAVEWESNGQPENNYKTTPPVLDSDGSFFLYSKLTVDKSRWQQGNVFSCSVMHEALHNHYT QKSLSLSPGK |
| Sequence No. | SEQ ID NO: 112 |
| hcIgG-10 | QVQLQESGGGLVQPGGSLRLSCAASGFAFGSSHMSWVRRAPGKGLEWVSTIHSGGGFGDYANSVQGR FTISRDVAKNTLYLQMNSLKPEDTAIYYCALATDWRKPPGQGTQVTVSSDKTHTCPPCPAPELLGGPSV FLFPPKPKDTLMISRTPEVTCVVVDVSHEDPEVKFNWYVDGVEVHNAKTKPREEQYNSTYRVVSVLTV |

TABLE B-continued

Amino acid sequences and nucleotide sequences of exemplary nanobodies, amino acid sequences of heavy-chain antibodies, amino acid sequences of humanized heavy-chain antibodies, and amino acid sequences of antibodies in a tetramer form, and SEQ ID NOs. thereof

| | |
|---|---|
| | LHQDWLNGKEYKCKVSNKALPAPIEKTISKAKGQPREPQVYTLPPSRDELTKNQVSLTCLVKGFYPSDI<br>AVEWESNGQPENNYKTTPPVLDSDGSFFLYSKLTVDKSRWQQGNVFSCSVMHEALHNHYTQKSLSLSP<br>GK |
| Sequence No. | SEQ ID NO: 113 |
| hcIgG-16 | QVQLQESGGGSVQAGGSLRLSCAASGYTYNKYSWGWFRQAPGKEREGVAGIDSDGSTSVADSVKGRF<br>TISKDNTKNTLYLQMNSLKPEDTAMYYCAASDWVSAIQALGVLAVRPYEYWGQGTQVTVSSDKTHTC<br>PPCPAPELLGGPSVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLPPSRDELTKNQV<br>SLTCLVKGFYPSDIAVEWESNGQPENNYKTTPPVLDSDGSFFLYSKLTVDKSRWQQGNVFSCSVMHEA<br>LHNHYTQKSLSLSPGK |
| Sequence No. | SEQ ID NO: 114 |
| hcIgG-20 | QVQLQESGGGSVQAGGSLRLSCASSGYSRTSRWMAWFRQAPGKEREGVAAIVTGGSSTLYANSMADR<br>VTISQDNAKNTVYLRMNNLKPEDTAMYYCAADKLAGDFWLVDRWRAWGQGTQVTVSSDKTHTCPP<br>CPAPELLGGPSVFLFPPKPKDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREPQVYTLPPSRDELTKNQVS<br>LTCLVKGFYPSDIAVEWESNGQPENNYKTTPPVLDSDGSFFLYSKLTVDKSRWQQGNVFSCSVMHEAL<br>HNHYTQKSLSLSPGK |
| Sequence No. | SEQ ID NO: 115 |
| Humanized heavy-<br>chain antibody | Amino acid sequence |
| HzhcIgG-07 | QVQLQESGGGLVQPGGSLRLSCAASGFAFGSSHMSWFRRAPGKGLEWVSTIHSGGGFGDYADSV<br>KGRFTISRDNSKNTLYLQMNSLRPEDTAVYYCALATDWRKPWGQGTLVTVSSDKTHTCPPCPAP<br>ELLGGPSVFLFPPKPKDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKSRWQQGNVFSCS<br>VMHEALHNHYTQKSLSLSPGK |
| Sequence No. | SEQ ID NO: 116 |
| HzhcIgG-20 | QVQLQESGGGLVQPGGSLRLSCAASGYSRTSRWMAWFRQAPGKGLEGVAAIYTGGSSTLYADS<br>VKGRFTISRDNAKNSVYLQMNSLRAEDTAVYYCAADKLAGDFWLVDRWRAWGQGTLVTVSSD<br>KTHTCPPCPAPELLGGPSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTVDKSR<br>WQQGNVFSCSVMHEALHNHYTQKSLSLSPGK |
| Sequence No. | SEQ ID NO: 117 |
| Tetramer antibody | Amino acid sequence |
| 4xNb-IgG-I | QVQLQESGGGLVQPGGSLRLSCAASGYSRTSRWMAWFRQAPGKGLEGVAAIYTGGSSTLYADS<br>VKGRFTISRDNAKNSVYLQMNSLRAEDTAVYYCAADKLAGDFWLVDRWRAWGQGTLVTVSSD<br>KTHTCPPCPAPELLGGPSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTVDKSR<br>WQQGNVFSCSVMHEALHNHYTQKSLSLSPGKGGGGSQVQLQESGGGLVQPGGSLRLSCAASGY<br>SRTSRWMAWFRQAPGKGLEGVAAIYTGGSSTLYADSVKGRFTISRDNAKNSVYLQMNSLRAEDT<br>AVYYCAADKLAGDFWLVDRWRAWGQGTLVTVSS |
| Sequence No. | SEQ ID NO: 118 |
| 4xNb-IgG-II | QVQLQESGGGLVQPGGSLRLSCAASGYSRTSRWMAWFRQAPGKGLEGVAAIYTGGSSTLYADS<br>VKGRFTISRDNAKNSVYLQMNSLRAEDTAVYYCAADKLAGDFWLVDRWRAWGQGTLVTVSSG<br>GGGSQVQLQESGGGLVQPGGSLRLSCAASGYSRTSRWMAWFRQAPGKGLEGVAAIYTGGSSTL<br>YADSVKGRFTISRDNAKNSVYLQMNSLRAEDTAVYYCAADKLAGDFWLVDRWRAWGQGTLVT<br>VSSDKTHTCPPCPAPELLGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPVLDSDGSFFLYSKLTVD<br>KSRWQQGNVFSCSVMHEALHNHYTQKSLSLSPGK |
| Sequence No. | SEQ ID NO: 119 |
| 4xNb-IgG-III | QVQLQESGGGLVQPGGSLRLSCAASGYSRTSRWMAWFRQAPGKGLEGVAAIYTGGSSTLYADS<br>VKGRFTISRDNAKNSVYLQMNSLRAEDTAVYYCAADKLAGDFWLVDRWRAWGQGTLVTVSSQ<br>VQLQESGGGLVQPGGSLRLSCAASGYSRTSRWMAWFRQAPGKGLEGVAAIYTGGSSTLYADSV<br>KGRFTISRDNAKNSVYLQMNSLRAEDTAVYYCAADKLAGDFWLVDRWRAWGQGTLVTVSSDK<br>THTCPPCPAPELLGGPSVFLFPPKPKDTLMISRTPEVTCVVVDVSHEDPEVKFNWYVDGVEVHNA |

TABLE B-continued

Amino acid sequences and nucleotide sequences of exemplary nanobodies, amino acid sequences of heavy-chain antibodies, amino acid sequences of humanized heavy-chain antibodies, and amino acid sequences of antibodies in a tetramer form, and SEQ ID NOs. thereof

|  |  |
|---|---|
|  | KTKPREEQYNSTYRVVSVLTVLHQDWLNGKEYKCKVSNKALPAPIEKTISKAKGQPREPQVYTLP PSRDELTKNQVSLTCLVKGFYPSDIAVEWESNGPENNYKTTPPVLDSDGSFFLYSKLTVDKSRW QQGNVFSCSVMHEALHNHYTQKSLSLSPGK |
| Sequence No. | SEQ ID NO: 120 |
| Amino acid sequence of Fc | DKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLDSDGSFFLYSKLTVDKS RWQQGNVFSCSVMHEALHNHYTQKSLSLSPGK |
| Sequence No. | SEQ ID NO: 121 |
| Amino acid sequence of linker | GGGGS |
| Sequence No. | SEQ ID NO: 122 |
| Amino acid sequence of human GITR | QRPTGGPGCGPGRLLLGTGTDARCCRVHTTRCCRDYPGEECCSEWDCMCVQPEFHCGDPCCTTC RHHPCPPGQGVQSQGKFSFGFQCIDCASGTFSGGHEGHCKPWTDCTQFGFLTVFPGNKTHNAVC VPGSPPAE |
| Sequence No. | SEQ ID NO: 123 |
| VH in HzhcIgG-07 | QVQLQESGGGLVQPGGSLRLSCAASGFAFGSSHMSWFRRAPGKGLEWVSTIHSGGGFGDYADSV KGRFTISRDNSKNTLYLQMNSLRPEDTAVYYCALATDWRKPWGQGTLVTVSS |
| Sequence No. | SEQ ID NO: 124 |
| VH in HzhcIgG-20 | QVQLQESGGGLVQPGGSLRLSCAASGYSRTSRWMAWFRQAPGKGLEGVAAIYTGGSSTLYADS VKGRFTISRDNAKNSVYLQMNSLRAEDTAVYYCAADKLAGDFWLVDRWRAWGQGTLVTVSS |
| Sequence No. | SEQ ID NO: 125 |
| Amino acid sequence of human GITR-His | QRPTGGPGCGPGRLLLGTGTDARCCRVHTTRCCRDYPGEECCSEWDCMCVQPEFHCGDPCCTTC RHHPCPPGQGVQSQGKFSFGFQCIDCASGTFSGGHEGHCKPWTDCTQFGFLTVFPGNKTHNAVC VPGSPPAEHHHHHH |
| Sequence No. | SEQ ID NO: 127 |

The SEQ ID NOs. corresponding to the sequences of examples disclosed herein are listed in Table C below.

TABLE C

SEQ ID NOs. of the sequences of examples disclosed herein

| Antibody No. | Amino acid sequence | | | | Nucleotide sequence |
|---|---|---|---|---|---|
|  | Full length | HCDR1 | HCDR2 | HCDR3 | Full length |
| Nb-01 | 64 | 1 | 23 | 45 | 86 |
| Nb-02 | 65 | 2 | 24 | 46 | 87 |
| Nb-03 | 66 | 3 | 25 | 47 | 88 |
| Nb-04 | 67 | 4 | 26 | 48 | 89 |
| Nb-05 | 68 | 5 | 27 | 49 | 90 |
| Nb-06 | 69 | 6 | 28 | 50 | 91 |
| Nb-07 | 70 | 7 | 29 | 51 | 92 |
| Nb-08 | 71 | 8 | 30 | 52 | 93 |
| Nb-09 | 72 | 9 | 31 | 53 | 94 |
| Nb-10 | 73 | 10 | 32 | 51 | 95 |
| Nb-11 | 74 | 11 | 33 | 48 | 96 |
| Nb-12 | 75 | 12 | 34 | 46 | 97 |
| Nb-13 | 76 | 13 | 35 | 54 | 98 |
| Nb-14 | 77 | 14 | 36 | 55 | 99 |
| Nb-15 | 78 | 15 | 37 | 56 | 100 |
| Nb-16 | 79 | 16 | 38 | 57 | 101 |
| Nb-17 | 80 | 17 | 39 | 58 | 102 |
| Nb-18 | 81 | 18 | 40 | 59 | 103 |
| Nb-19 | 82 | 19 | 41 | 60 | 104 |
| Nb-20 | 83 | 20 | 42 | 61 | 105 |
| Nb-21 | 84 | 21 | 43 | 62 | 106 |
| Nb-22 | 85 | 22 | 44 | 63 | 107 |

TABLE C-continued

SEQ ID NOs. of the sequences of examples disclosed herein

| Antibody No. | Amino acid sequence | | | | Nucleotide sequence |
|---|---|---|---|---|---|
|  | Full length | HCDR1 | HCDR2 | HCDR3 | Full length |
| hcIgG-02 | 108 | 2 | 24 | 46 |  |
| hcIgG-03 | 109 | 3 | 25 | 47 |  |
| hcIgG-04 | 110 | 4 | 26 | 48 |  |
| hcIgG-07 | 111 | 7 | 29 | 51 |  |
| hcIgG-09 | 112 | 9 | 31 | 53 |  |
| hcIgG-10 | 113 | 10 | 32 | 51 |  |
| hcIgG-16 | 114 | 16 | 38 | 57 |  |
| hcIgG-20 | 115 | 20 | 42 | 61 |  |

| | Full length | HCDR1 | HCDR2 | HCDR3 | VH |
|---|---|---|---|---|---|
| HzhcIgG-07 | 116 | 7 | 29 | 51 | 124 |
| HzhcIgG-20 | 117 | 20 | 42 | 61 | 125 |
| 4xNb-IgG-I | 118 | 20 | 42 | 61 | 125 |
| 4xNb-IgG-II | 119 | 20 | 42 | 61 | 125 |
| 4xNb-IgG-III | 120 | 20 | 42 | 61 | 125 |

In another aspect, the present invention provides a fusion protein or immunoconjugate (referred to as the fusion protein or immunoconjugate disclosed herein), wherein the antibody disclosed herein is fused or conjugated to one or more heterologous molecules (second molecules), including, but not limited to, proteins/polypeptides, markers, drugs, or cytotoxic agents.

Methods for fusion or conjugation of a protein, polypeptide or peptide to an antibody are known in the art. See, for example, U.S. Pat. Nos. 5,336,603, 5,622,929 and EP 367,166.

In some embodiments, the drug in the fusion protein or immunoconjugate disclosed herein is an anti-tumor drug.

In another aspect, the present invention provides a composition or kit (referred to as the composition or kit disclosed herein) comprising the antibody disclosed herein.

In some embodiments, the composition or kit disclosed herein comprises a carrier and/or an instruction.

In some embodiments, the antibody in the composition or kit disclosed herein is conjugated to a diagnostic or detectable reagent.

In another aspect, the present invention provides an isolated nucleic acid (referred to as the isolated nucleic acid disclosed herein or the nucleic acid (molecule) disclosed herein) encoding the antibody or the fragment thereof (including an antigen-binding fragment) disclosed herein, the fusion protein disclosed herein, or the immunoconjugate disclosed herein.

In some embodiments, the nucleic acid molecule disclosed herein is substantially a purified nucleic acid molecule.

In some embodiments, the nucleic acid molecule disclosed herein comprises a nucleotide sequence encoding a heavy chain variable region of any one of the antibodies shown in Table B, or a variant thereof. In one specific embodiment, the nucleic acid molecule is a nucleotide sequence of a nanobody listed in Table B. The nucleic acid molecule disclosed herein comprises a nucleotide sequence encoding at least one CDR region and typically all three CDR regions from a heavy chain of any one of the antibodies listed in Table B, or a variant thereof.

Some other nucleic acid molecules disclosed herein are substantially identical (e.g., at least 65%, 80%, 95%, or 99% identical) to a nucleotide sequence encoding a nucleic acid molecule of an amino acid sequence shown in Table B. The polypeptides encoded by the polynucleotides may demonstrate GITR antigen-binding ability when expressed in a suitable expression vector.

It will be appreciated by those skilled in the art that the amino acid sequence of each antibody or polypeptide may be encoded by a variety of nucleic acid sequences due to codon degeneracy.

In some embodiments, the nucleic acid sequence disclosed herein encodes any of the above nanobodies disclosed herein. In some embodiments, the nucleic acid sequence encoding nanobody disclosed herein comprises a nucleotide sequence of SEQ ID NOs: 86-107 or a sequence substantially identical thereto. In some embodiments, the nucleic acid sequence encoding nanobody disclosed herein consists of a nucleotide sequence of SEQ ID NOs: 86-107 or a sequence substantially identical thereto.

A "substantially identical" nucleotide sequence refers to a sequence that has at least 80%, 85%, 90%, 91%, 92%, 93%, 94%, 95%, 96%, 97%, 98%, 99% or higher identity to a reference nucleotide sequence. The identity of nucleotide sequences can be determined using various sequence alignment methods well known in the art. For example, using BLAST sequence alignment search tools available from the website of National Center for Biotechnology Information (NCBI), Bethesda, Md. Generally, percent identity is determined using default parameters of NCBI Blast.

The polynucleotide sequences of a GITR antibody or binding fragments thereof may be produced by solid phase de novo DNA synthesis or by PCR mutagenesis of existing sequences (e.g., the sequences shown in Table B and Table 2) encoding the GITR antibody or the binding fragments thereof. Direct chemical synthesis of nucleic acids can be implemented by methods known in the art, such as the phosphotriester method in Narang et al., 1979, *Meth. Enzymol.* 68:90; the phosphodiester method in Brown et al., *Meth. Enzymol.* 68:109, 1979; the diethylphosphoramidite method of Beaucage et al., *Tetra. Lett.*, 22:1859, 1981; and the solid phase support method in U.S. Pat. No. 4,458,066. Introduction of mutations into polynucleotide sequences by PCR can be implemented as described, for example, in *PCR Technology: Principles and Applications for DNA Amplification*, H. A. Erlich (eds.), Freeman Press, NY, N.Y., 1992; *PCR Protocols: A Guide to Methods and Applications*, Innis et al. (eds.), Academic Press, San Diego, Calif., 1990; Mattila et al., *Nucleic Acids Res.* 19:967, 1991; and Eckert et al., *PCR Methods and Applications* 1:17, 1991.

In another aspect, the present invention provides a vector comprising the nucleic acid disclosed herein (referred to as the vector disclosed herein).

In some embodiments, the vector disclosed herein is an expression vector, i.e., used to express polynucleotides encoding antibody chains (e.g., chains of any of the antibodies disclosed herein) or polypeptides (e.g., any of the fusions and conjugates disclosed herein) that bind to GITRs.

Both virus-based expression vectors and non-viral expression vectors may be used to produce antibodies in mammalian host cells. Non-viral vectors and systems include plasmids, episomal vectors, and artificial chromosomes, and typically contain expression cassettes for expressing proteins or RNAs (see, e.g., Harrington et al., *Nat. Genet.*, 15:345, 1997). Available viral vectors include vectors based on retroviruses, adenoviruses, adeno-associated viruses and herpes viruses, and vectors based on SV40, papillomaviruses, HBP EB viruses, vaccinia viruses, and Semliki Forest viruses (SFV). See, Smith, *Annu. Rev. Microbiol.*, 49:807, 1995; and Rosenfeld et al., *Cell*, 68:143, 1992.

In another aspect, the present invention provides a host cell comprising the vector disclosed herein (referred to as the host cell disclosed herein).

In some embodiments, the host cell disclosed herein is any of host cells appropriate for cloning or expressing the vector, including prokaryotic and eukaryotic cells.

In some embodiments, the host cell disclosed herein is a bacterium, a yeast cell, a mammal cell or an immune effector cell (such as T cell).

For example, antibodies may be produced in bacteria, when glycosylation and Fc effector functions are not required. Expressions of antibody fragments and polypeptides in bacteria are described in, e.g., U.S. Pat. Nos. 5,648,237, 5,789,199, and 5,840,523. In addition to prokaryotes, eukaryotic microorganisms such as filamentous fungi or yeasts are appropriate cloning or expression hosts for antibody-encoding vectors, including fungal and yeast strains in which the glycosylation pathway is "humanized". This may result in the production of antibodies with partially or fully human glycosylation patterns. See Gerngross, *Nat. Biotech*, 22 (2004) 1409-1414; and Li, H. et al., *Nat. Biotech*, (2006) 24:210-215. Host cells appropriate for expression of glycosylated antibodies may also be derived from multicellular organisms (invertebrates and vertebrates). Examples of invertebrate cells include plant and insect cells. Numerous baculovirus strains have been identified, which may be used in conjunction with insect cells, particularly for the transfection of *Spodoptera frugiperda* cells. Plant cell cultures may also be used as hosts. See, e.g., U.S. Pat. Nos. 5,959,177, 6,040,498, 6,420,548, 7,125,978 and 6,417,429 (describing the PLANTIBODIES™ technology for the production of antibodies in transgenic plants). Vertebrate cells that may be used as hosts include, e.g., available suspension growth adapted mammalian cell lines. Other examples of available mammalian host cell lines include SV40 transformed monkey kidney CV1 lines (COS-7); human embryonic kidney lines (HEK293 cells as described, e.g., in Graham, F. L. et al., *J. Gen Virol.* 36 (1997) 59); baby hamster kidney (BHK) cells; mouse Sertoli cells (e.g., TM4 cells as described in Mather, J. P., *Biol. Reprod.* 23 (1980) 243-251); monkey kidney cells (CV1); African green monkey kidney cells (VERO-76); human cervical cancer cells (HELA); canine kidney cells (MDCK); buffalo rat hepatocytes (BRL 3A); human lung cells (W138); human hepatocytes (Hep G2); mouse mammary tumor (MMT 060562); TRI cells, such as those described in Mather, J. P. et al., *Annals N.Y. Acad. Sci.* 383 (1982) 44-68; MRC 5 cells; and FS4 cells. Other available mammalian host cell lines include Chinese Hamster Ovary (CHO) cells such as DHFR-CHO cells (Urlaub, G. et al., *Proc. Natl. Acad. Sci.* USA 77 (1980) 4216-4220), and myeloma cells such as Y0, NS0 and Sp2/0. A review of mammalian host cell lines suitable for producing an antibody is described in, e.g., Yazaki, P. and Wu, A. M., *Methods in Molecular Biology*, Vol. 248, Lo. B. K. C. (eds.), Humana Press, Totowa, N.J. (2004) pp. 255-268.

In some preferred embodiments, *E. coli* cells (TG1 cells), human embryonic kidney lines (293 cells) or human cervical cancer cells (HELA) may be used to express and produce the GITR-binding antibody polypeptides disclosed herein.

In another aspect, the present invention provides a method for preparing the antibody or the antigen-binding fragment, the fusion protein, and the immunoconjugate disclosed herein (referred to as the preparation method disclosed herein or the method disclosed herein), comprising: incubating the host cell disclosed herein under a condition suitable for expressing the antibody or the antigen-binding fragment thereof, the fusion protein, or the immunoconjugate disclosed herein.

In some embodiments, the method disclosed herein further comprises any expression measures that facilitate the expression and purification of the antibody or the antigen-binding fragment thereof, the fusion protein or the immunoconjugate disclosed herein, e.g., adopting any of expression elements and regulatory elements known to those skilled in the art, such as secretion signal sequences, expression enhancers, efficient promoters, and the like.

In another aspect, the present invention provides a pharmaceutical composition (referred to as the pharmaceutical composition disclosed herein), comprising the antibody or the antigen-binding fragment thereof, the fusion protein, or the immunoconjugate disclosed herein, and optionally a pharmaceutically acceptable carrier.

In some embodiments, the pharmaceutical composition disclosed herein further comprises other components, such as an immunotherapeutic agent, an anti-angiogenic agent and a chemotherapeutic agent.

In some embodiments, the immunotherapeutic agent in the pharmaceutical composition disclosed herein may induce or enhance an immune response, including, for example: 1) a dendritic cell activator; 2) a vaccine adjuvant; 3) a T cell stimulator; 4) an immune checkpoint inhibitor; and 5) an inhibitory cell or cytokine and/or an enzyme inhibitor.

In some embodiments, the pharmaceutical composition disclosed herein may comprise other compounds, drugs and/or agents for treating cancer, including but not limited to chemotherapy drugs, small molecule drugs or antibodies that stimulate an immune response against a given cancer. In some instances, the therapeutic composition may comprise: an anti-CTLA-4 antibody, an anti-PD-1 antibody, an anti-PDL-1 antibody, an anti-OX40 (also known as CD134, TNFRSF4, ACT35, and/or TXGP1L) antibody, an anti-CD137 antibody or an anti-LAG-3 antibody.

In another aspect, the present invention provides use of the GITR binding molecule (antibody) disclosed herein in diagnosis and/or detection (referred to as the use of the present invention, or the use of the present invention in diagnosis and/or detection) and a composition used therein. Any of the anti-GITR antibodies disclosed herein may be used for detecting (quantitatively or qualitatively) the presence of GITR in a biological sample. The presence of GITRs in a biological sample may be detected by, e.g., immunohistochemistry, immunocytochemistry, flow cytometry (e.g., FACS), magnetic beads complexed with antibody molecules, ELISA, and PCR techniques (e.g., RT-PCR), and the like. In some embodiments, the biological sample includes body fluids, cells or tissues. In certain embodiments, the biological sample is blood, serum, or other liquid samples of a biological source.

In one embodiment, a method for diagnosis or detection using the anti-GITR antibody is provided. In a further aspect, a method for detecting the presence of GITRs in a biological sample is provided. In some embodiments, the method comprises contacting the biological sample with the anti-GITR antibody described herein under a condition that allows the anti-GITR antibody to bind to a GITR, and detecting whether a complex is formed between the anti-GITR antibody and GITR. The method may be in vitro or in vivo.

In one embodiment, the anti-GITR antibody is used to select a subject suitable for treatment with the anti-GITR antibody, e.g., when a GITR is a biomarker for patient selection. Exemplary disorders that may be diagnosed using the antibodies disclosed herein include immune disorders and aplastic disorders. In some embodiments, a method for stratifying subjects with immune disorders or aplastic disorders by using the antibodies disclosed herein is provided. In some embodiments, the anti-GITR antibody may be any of the aforementioned immunoconjugates disclosed herein conjugated with a diagnostic or detectable agent. In some embodiments, the present invention provides a kit for diagnosis or detection comprising the GITR binding molecule disclosed herein, such as any of the anti-GITR antibodies disclosed herein.

In one embodiment, the present invention provides a method for detecting the presence of GITRs in a sample, comprising:

(a) contacting the sample with the isolated antibody or the antigen-binding fragment thereof, the fusion protein or the immunoconjugate disclosed herein; and (b) detecting formation of a complex of the antibody or the antigen-binding fragment thereof, or the fusion protein or immunoconjugate with GITR proteins.

In another aspect, the present invention provides a method for screening, identification and characterization of the antibodies disclosed herein. The anti-GITR antibodies disclosed herein may be screened, identified, or characterized for their physical/chemical properties and/or biological activities by various assays known in the art.

Phages/phagemids that bind with high affinity to a target antigen may be selected from a phage/phagemid display nanobody library. Various methods for presenting or displaying antibodies or fragments thereof on a phage/phagemid surface and screening the library are described.

For the identification of antibodies, the antibodies disclosed herein may be identified or characterized with respect to the antigen binding activity thereof, e.g., by known methods such as ELISA, aLISA, western blots, antibody or reverse phase microarrays or the like, as well as the methods described in the examples.

For example, the antibodies may be detected using a ForteBio assay. A ForteBio affinity assay of prior art may be implemented (Estep, P., et al., *High throughput solution based measurement of antibody-antigen affinity and epitope binning. MAbs,* 2013.5(2):270-8). For example, an AHQ sensor may be equilibrated for 30 min off-line in an assay buffer, followed by detecting online for 60 s to establish a baseline. Then, the AHQ sensor, loaded on-line with purified antibodies, is exposed to 100 nM antigens for 5 min, and then transferred to the assay buffer for 5-min off-line measurement. Kinetic analysis is performed using a 1:1 binding model.

In another aspect, the present invention provides a method for treating a cancerous condition, inducing or enhancing immune response in an individual, and/or stimulating antigen-specific T cell response, characterized by comprising administering to the individual an effective amount of the isolated antibodies or the antigen-binding fragments thereof, the fusion proteins or the immunoconjugates disclosed herein.

In some embodiments, an immune response is provoked against a tumor antigen or an infectious factor.

In some embodiments, methods described above of the present invention may be used for treating or preventing "immune conditions", including, e.g., pathological inflammations, inflammatory conditions, and autoimmune conditions or diseases, as well as infections, persistent infections, and proliferative conditions such as cancers, tumors and angiogenesis, including infections, tumors, and cancers that resist to eradications by the immune system.

In some embodiments, methods described above of the present invention may be used for treating or preventing "immune disorders", wherein the immune disorders refer to diseases in mammals that are caused, mediated, or otherwise promoted by mammal immune system components; or diseases that stimulate or intervene immune responses having an improving effect on disease progressions. The "immune disorders" include autoimmune diseases, immune-mediated inflammatory diseases, non-immune-mediated inflammatory diseases, infectious diseases, and immunodeficiency.

Examples of such immune-related diseases and inflammatory diseases (some of which are immune-mediated or T-cell-mediated) that may be treated with the antibodies disclosed herein include: systemic lupus erythematosus, rheumatoid arthritis, juvenile chronic arthritis, spondyloarthropathy, systemic sclerosis (scleroderma), idiopathic inflammatory myopathy (dermatomyositis and polymyositis), sicca syndrome, systemic vasculitis, sarcoidosis, autoimmune haemolytic anemia (autoimmune pancytopenia and paroxysmal nocturnal hemoglobinuria), autoimmune thrombocytopenia (idiopathic thrombocytopenic purpura and immune-mediated thrombocytopenia), thyroiditis (Graves' disease, Hashimoto's thyroiditis, juvenile lymphocytic thyroiditis, and atrophic thyroiditis), diabetes, immune-mediated renal diseases (glomerulonephritis and tubulointerstitial nephritis), central and peripheral demyelinating disease such as the multiple sclerosis, idiopathic demyelinating polyneuropathy or Guillain-Barre syndrome, and chronic inflammatory demyelination polyneuropathy, hepatobiliary diseases such as infectious hepatitis (type A, type B, type C, type D, type E and other non-hepatitis virus hepatitis), autoimmune chronic active hepatitis, primary biliary cirrhosis, granulomatous hepatitis, and sclerosing cholangitis, inflammatory and fibrotic lung diseases such as inflammatory bowel diseases (ulcerative colitis: Crohn's disease), gluten sensitive enteropathy, and Whipple's disease, autoimmunity or immune-mediated skin diseases including bullous dermatosis, erythema multiforme and contact dermatitis, psoriatic, allergic diseases such as asthma, allergic rhinitis, atopic dermatitis, food hypersensitivity and urticaria, immunological diseases of lung such as eosinophilic pneumonia, idiopathic pulmonary fibrosis and hypersensitivity pneumonitis, graft-related diseases including graft rejection and graft versus host disease. Transmissible diseases include AIDS (HIV infection), hepatitis A, B, C, D, and E, bacterial infections, fungal infections, protozoal infections and parasitic infections.

In some embodiments, the method described above of the present invention may be used for treating or preventing "cancerous disorders", including, e.g., cancers, cancer cells, tumors, angiogenesis, and pre-cancerous disorders, such as dysplasia.

In some embodiments, the cancer is a metastatic cancer, a metastatic cancer or a refractory cancer, more preferably a solid cancer or a hematological cancer, most preferably melanoma, lung cancer, head and neck cancer, colorectal cancer, non-small cell lung cancer, squamous cell carcinoma of the head and neck, bladder cancer, breast cancer, uterine/cervical cancer, ovarian cancer, prostate cancer, testicular cancer, esophageal cancer, gastrointestinal cancer, pancreatic cancer, colon cancer, kidney cancer, gastric cancer, germ cell cancer, osteocarcinoma, liver cancer, thyroid cancer, skin cancer, neoplasm of the central nervous system, lymphoma, leukemia, myeloma, sarcoma or a virus-related cancer.

In some embodiments, the effective amount of the antibodies disclosed herein is an amount achieving one or more of the following effects in an individual: a) inhibiting regulatory T cells that suppress effector T cell activities; b) reducing the level of circulating regulatory T cells; c) activating effector T cells; d) inducing or enhancing effector T cell proliferations; e) inhibiting tumor growth; f) inducing tumor regression; and g) increasing the production of IL-2 and/or IFN-γ in GITR-expressing T cells and increasing T cell proliferations.

In some embodiments, the method described above further comprises: a) administering chemotherapy; b) administering radiation therapy; and/or c) administering one or more of additional therapeutic agents, preferably immunostimulants.

In some embodiments, the immunostimulant in the method described above is selected from T-VEC, PD1 antagonists, PDL1 antagonists, CTLA-4 antagonists, and BiTE.

In some embodiments, the chemotherapy, the radiation therapy, or the therapeutic agent in the method described above is administered before, simultaneously with, or after the antibody or the antigen-binding fragment thereof.

The following examples are described to assist in understanding the present invention. The examples are not intended and should not be interpreted in any way as limiting the protection scope of the present invention.

EXAMPLES

Example 1. Screening of Anti-GITR Nanobodies

1. Camel Immunity 1 mg of antigen GITR-His (Acro biosystems) was mixed with an equal volume of Freund's adjuvant (Sigma) and aliquoted in two tubes to immunize two wild Bactrian camels. The camels were immunized as such once a week for a total of 7 doses so as to stimulate B lymphocytes to express antigen-specific nanobodies. After the seven doses, the serum titer of GITR-His nanobodies produced in wild Bactrian camels reached greater than 1:1000, thereby confirming that the desired nanobodies were produced in the camels.

2. Construction of Phage Display Nanobody Library (1) After 7 immunizations, 100 mL of camel blood was collected, and peripheral blood lymphocytes were isolated to give total RNAs;

(2) the total RNAs obtained in step (1) were reversely transcribed into cDNAs by RT-PCR, and then VHHs were obtained by nested PCR (two PCRs) amplification, the principle of which is shown in FIG. 1;

(3) according to the manufacturer's package insert, 20 μg of phage display vectors and 10 μg of VHH fragments were cleaved using restriction enzymes PstI (NEB) and NotI (NEB), and then two fragments obtained from the two cleavages were ligated by T4 ligase (NEB);

(4) competent *E. coli* cells TG1 were electrotransformed using the ligated products to establish a nanobody library.

3. Screening of Anti-GITR Nanobodies (1) The antigen protein GITR-His (Acro biosystems) in 100 mM NaHCO$_3$ (pH8.2) was immobilized on a plate (Nunc), and was placed at 4° C. overnight;

(2) 100 μL of blocking buffer (5% BSA, Jackson) was added to the mixture on the next day for a 2-h blocking at room temperature;

(3) after 2 h, 100 μL of phage (5×10$^{11}$ PFU (plaque forming unit) of phage display nanobody library constructed above was added to the mixture) was added and the mixture was incubated at room temperature for 1 h;

(4) the mixture was washed 5 times with PBST (PBS+ 0.05% Tween-20 (Bio Basic Inc., BBI)) to remove unbound phages;

(5) phages specifically bound to the antigen protein GITR-His were dissociated with 100 mM TEA (Sigma) eluent, and then used to infect *E. coli* TG1 cells in logarithmic phase. The cells were incubated at 37° C. for 1 h, and the phages were expanded for the next round of screening;

(6) steps (1) to (5) were repeated 3 times to give enriched phages specifically bound to the antigen protein GITR-His.

4. Positive Clones Identified by PE-ELISA (1) From the cell culture dishes containing the phages obtained after the above three rounds of screening, 1,000 individual colonies were randomly selected and inoculated in TB medium (2% tryptone, 2.4% yeast extracts, 72 mM K$_2$HPO$_4$, 17 mM KH$_2$PO$_4$, and 0.4% glycerol) containing Amresco. After the colonies grew to the logarithmic phase, IPTG (Sigma) was added until to a final concentration of 1 mM, and then cultured at 28° C. overnight;

(2) crude antibodies were obtained by a conventional osmotic shock method, and the crude antibodies were transferred to an enzyme-labeled plate (Nunc) coated with the antigen GITR-His overnight, and incubated at room temperature for 1 h;

(3) unbound antibodies were washed off with PBST, then mouse anti-HA tag antibody (SinoBiological) was added, and placed at room temperature for 1 h;

(4) unbound antibodies were washed off with PBST, then goat anti-mouse alkaline phosphatase labeled antibody (Millipore) was added, and placed at room temperature for 1 h;

(5) unbound antibodies were washed off with PBST, then alkaline phosphatase color developing solution (Sincella M30100) was added, and the absorption values at 405 nm wavelength showed on an ELISA instrument (Thermo (MULTISCAN FC)) were read; sample wells with OD values greater than 3 times of the control wells (Ratio: +/−) were determined as positive clone wells;

(6) PE-ELISA (Post-Enrichment Enzyme-linked Immunosorbent Assay, after enrichment) results showed that there were a total of 486 positive clones, and the ratio (Ratio: +/−) was between 3-30; then, all positive clones were transferred to LB medium for cultivation overnight, and plasmids were extracted for sequencing.

5. Analysis of Sequencing Results

According to the sequence alignment software Vector NTI, the gene sequences of each clone were analyzed. The strains with the same CDR1, CDR2, and CDR3 sequences were determined as the same clone strain, and the strains with different sequences were determined as different clone strains. Finally, 22 strains of nanobodies with different sequences were obtained, and their ELISA results are shown in Table 1.

TABLE 1

ELISA results of nanobodies Nb-01 to Nb-22

| Antibody No. | Amino acid SEQ ID NO | Sample OD (+) | Reference OD (−) | Ratio (+/−) |
|---|---|---|---|---|
| Nb-01 | 64 | 0.467 | 0.075 | 6.227 |
| Nb-02 | 65 | 1.425 | 0.069 | 20.652 |
| Nb-03 | 66 | 0.786 | 0.067 | 11.728 |
| Nb-04 | 67 | 1.628 | 0.074 | 22.000 |
| Nb-05 | 68 | 1.412 | 0.066 | 21.518 |
| Nb-06 | 69 | 0.314 | 0.095 | 3.305 |
| Nb-07 | 70 | 2.346 | 0.072 | 32.583 |
| Nb-08 | 71 | 1.705 | 0.074 | 23.041 |
| Nb-09 | 72 | 1.449 | 0.063 | 23.107 |
| Nb-10 | 73 | 2.269 | 0.076 | 29.855 |
| Nb-11 | 74 | 0.552 | 0.071 | 7.775 |
| Nb-12 | 75 | 0.444 | 0.098 | 4.531 |
| Nb-13 | 76 | 0.263 | 0.080 | 3.288 |
| Nb-14 | 77 | 0.460 | 0.115 | 4.000 |
| Nb-15 | 78 | 1.254 | 0.249 | 5.036 |
| Nb-16 | 79 | 1.674 | 0.081 | 20.667 |
| Nb-17 | 80 | 1.037 | 0.069 | 15.112 |
| Nb-18 | 81 | 1.010 | 0.103 | 9.800 |
| Nb-19 | 82 | 1.324 | 0.072 | 18.469 |
| Nb-20 | 83 | 1.414 | 0.116 | 12.212 |
| Nb-21 | 84 | 0.522 | 0.069 | 7.548 |
| Nb-22 | 85 | 0.606 | 0.060 | 10.031 |

Example 2. Construction, Expression and Purification of Heavy Chain Antibodies 1. Construction of Heavy Chain Antibody (hcIgG):
(1) the cDNA of nanobodies Nb-02, Nb-03, Nb-04, Nb-07, Nb-09, Nb-10, Nb-16, and Nb-20 was amplified by PCR;
(2) each PCR fragment was obtained by gel recycling, and constructed into HEK293 expression vector pTT5 (Biotechnology Research Institute; Montreal, Canada) by a homologous recombination method (Vazyme, C112-01/02), which contains the IgG1 Fc fragment having the following DNA sequence:

(SEQ ID NO: 126)
GACAAAACCCACACCTGTCCCCCTTGTCCTGCTCCCGAGCTCCTGGGAGG

ACCTTCCGTGTTCCTCTTCCCTCCCAAACCCAAGGACACCCTGATGATTA

GCAGGACACCCGAGGTGACCTGTGTGGTGGTGGATGTGAGCCATGAGGAC

CCCGAGGTGAAGTTTAACTGGTACGTGGACGGCGTCGAGGTGCACAACGC

TAAGACCAAACCCAGGGAGGAGCAGTACAACTCCACATACCGGGTCGTGA

GCGTGCTGACCGTCCTGCACCAGGATTGGCTGAATGGCAAGGAGTACAAG

TGCAAGGTGAGCAACAAGGCCCTGCCCGCCCCCATCGAGAAGACCATCAG

CAAGGCCAAAGGACAGCCTCGGGAGCCCCAGGTTTATACTCTCCCCCCA

GCCGGGACGAACTGACCAAGAATCAGGTGTCCCTCACCTGCCTCGTGAAG

GGCTTTTACCCCAGCGACATTGCCGTGGAGTGGGAGAGCAATGGACAGCC

CGAAAACAACTACAAGACCACACCCCCCGTCCTGGACTCCGATGGCAGCT

TCTTCCTGTACAGCAAGCTGACCGTGGACAAGAGCAGGTGGCAGCAGGGC

AACGTGTTTAGCTGCAGCGTCATGCACGAGGCTCTCCACAACCACTACAC

CCAGAAGTCCCTGAGCCTGAGCCCCGGAAAGTGA;

(3) the correctness of the construction of the vectors was verified by sequencing (Genewiz).

2. Expression of hcIgG Protein
(1) HEK293 cells (Invitrogen) were subcultured according to the desired transfection volume and the cell density was adjusted to 1×10$^6$ cells/mL the day before transfection. The cell density on the day of transfection was approximately 2×10$^6$ cells/mL;
(2) F17 (Gibco, A13835-01) medium with 1/10 of the final volume was used as transfection buffer, 10 μg of constructed HEK293 expression vector pTT5 was added to each milliliter of transfection buffer, and mixed;
(3) 30 μg of PEI (polyethyleneimine, Polysciences, 23966) was added to the plasmids in each milliliter of transfection buffer, mixed well and incubated at room temperature for 10 min. The mixture was poured gently to the HEK293 cell suspension, and then the cells were cultured at 36.5° C. and 8% $CO_2$;
(4) after an overnight incubation, 1/50 the volume of transfection of 200 g/L FEED (Sigma, H6784-100G) and 200 g/L glucose mother solution were supplemented to the mixture, and VPA (valproic acid Gibco, 11140-050) was added until to a final concentration of 2 mM/L after 20 h;
(5) after the cells were continuously cultivated for 7 days, the cell supernatant was collected by centrifugation for purification.

3. Purification of hcIgG Protein
The target hcIgG protein was purified with 5 mL of HiTrap™ MabSelect SuRe™ (GE Healthcare). The specific procedure is as follows:

(1) endotoxin was removed from the AKTA protein purification system with 0.1 M NaOH (overnight); on the day of sample collection, the above cell supernatant was centrifuged at 7,500 rpm for 30 min and filtered by SARTOPORE (Sartorius, 5441307H4); the system was washed and the column was equilibrated with 5 times column volume of binding buffer (Tris 20 mM, NaCl 150 mM, pH 7.2) before purification; the centrifuged cell supernatant was loaded on the column; the column was re-equilibrated with 5-10 times column volume of binding buffer to the baseline equilibrium; the antibody was eluted with an elution buffer (citric acid+sodium citrate 100 mM, pH 3.5), and samples were collected based on the UV absorption value; and each 1 mL of the collected solution was neutralized with 80 μL of neutralization buffer (Tris-HCl 2M) for further use.

Figure 2:
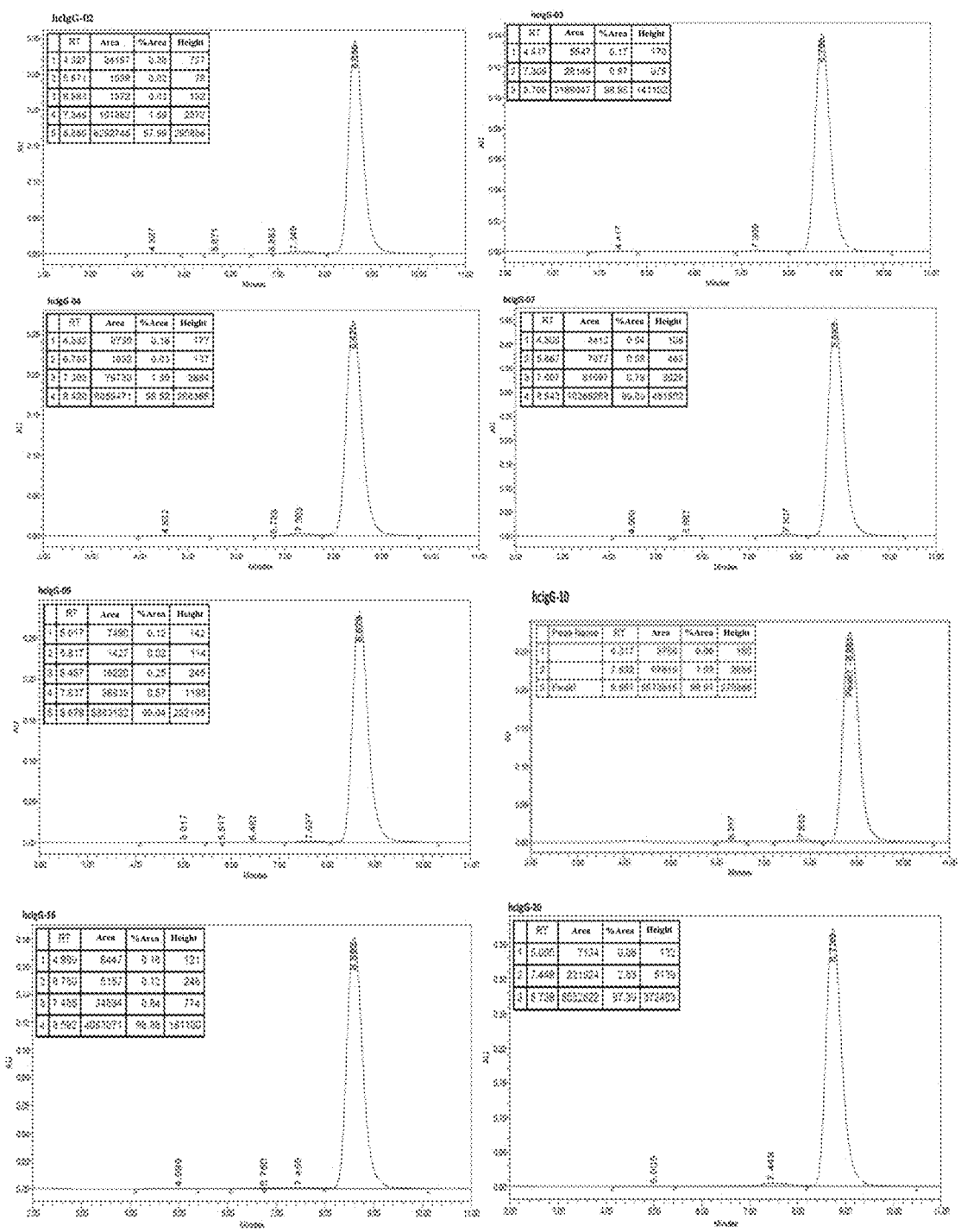
FIG. 2 shows purity results of hcIgG after detection and purification by SEC.

(2) The purified proteins were tested for purity using SEC-HPLC (size exclusion-high-performance liquid chromatography), and the results are shown in FIG. 2. The purities of all hcIgG were higher than 97% after one-step affinity purification.

The heavy-chain antibodies hcIgG-02, hcIgG-03, hcIgG-04, hcIgG-07, hcIgG-09, hcIgG-10, hcIgG-16 and hcIgG-20 were obtained, with specific sequences shown in Table B.

Example 3. Property Identification for Heavy-Chain Antibodies

1. ForteBio KD Test
In this experiment, kinetics and affinity for the antigen-antibody binding were determined by Fortebio method (Estep, P et al., High throughput solution Based measurement of antibody-antigen affinity and epitope binning. *MAbs*, 2013.5 (2): 270-278), and the anti-GITR antibody of GITR Inc. was adopted as a positive control (referred to as TRX518 in this application, it is obtained by cloning according to the sequence provided in U.S. 20130183321A1, with a light chain and a heavy chain having sequences of SEQ ID NO: 44 and SEQ ID NO: 54 in U.S. 20130183321A1 respectively, and the expression was achieved by transiently transfecting HEK293 cells). The specific determination method is as follows:

(1) Preparation of the sensor: The AHQ sensor (Pall, 1506091) was immersed in SD buffer (PBS 1x, BSA 0.1%, Tween-20 0.05%) half an hour before the experiment.

(2) Experimental procedure: 100 μl of SD buffer and antibodies (hcIgG-02, hcIgG-03, hcIgG-04, hcIgG-07, hcIgG-09, hcIgG-10, hcIgG-16 and hcIgG-20, control antibody), GITR-His (Acro biosystems) were added to a 96-well half-volume black polystyrene microplate. The plate was arranged according to the positions of the samples, the position of the sensor was selected, and the operation procedures were set as: Baseline, Loading ~1 nm, Baseline, Association and Dissociation, each running for a time depending on the binding and dissociation rates of the sample, at a rotation speed of 400 rpm and a temperature of 30° C.

(3) A 1:1 binding model was adopted for kinetic analysis. It was found that the antibodies disclosed herein (hcIgG-02, hcIgG-03, hcIgG-04, hcIgG-07, hcIgG-09, hcIgG-10, hcIgG-16, and hcIgG-20) all had a higher affinity than the control antibody TRX518, and the results are shown in Table 2.

TABLE 2 hcIgG affinity determination results

| | Amino acid SEQ ID NO: | Antibodies are on an AHQ tip, and the human GITR-His is in solution (100 nM) (the univalent affinity (M)) | Binding constant (1/Ms) | Dissociation constant (1/s) |
|---|---|---|---|---|
| hcIgG-02 | 108 | 6.33E−09 | 3.38E+05 | 2.14E−03 |
| hcIgG-03 | 109 | 5.30E−09 | 3.24E+05 | 1.72E−03 |
| hcIgG-04 | 110 | 7.92E−09 | 2.56E+05 | 2.02E−03 |
| hcIgG-07 | 111 | 4.08E−09 | 2.43E+05 | 9.90E−04 |
| hcIgG-09 | 112 | 1.89E−09 | 2.57E+05 | 4.87E−04 |
| hcIgG-10 | 113 | 3.22E−09 | 2.31E+05 | 7.42E−04 |
| hcIgG-16 | 114 | 9.81E−09 | 1.17E+05 | 1.14E−03 |
| hcIgG-20 | 115 | 1.85E−09 | 3.49E+05 | 6.46E−04 |
| TRX518 | | 2.62E−08 | 1.85E+05 | 4.84E−03 |

2. Detection of the Binding of hcIgG to an Antigen on the Cell Surface (1) Cell preparation: The pCHO1.0 vector (Invitrogen) carrying human GITR cDNA cloned to a multiple cloning site (MCS) was transfected into Chinese hamster ovary cancer cells (CHO) (Invitrogen) to produce human GITR-overexpressing CHO cells (CHO-GITR), the CHO cells (CHO-GITR) overexpressing human GITR on the surface thereof were counted, and diluted to 1×10$^6$ cells/mL, and added to a U-bottom 96-well plate with 100 µL/well.

(1) Detection: The cell suspension was centrifuged at 400 g for 5 min to remove the cell medium. Serial dilutions of the sample were added to a U-shaped plate, and then the cells were resuspended and added to the plate with 100 µL/well. The plate was put onto the ice to stand for 30 min The cell suspension was centrifuged at 400 g for 5 min, and the supernatant was discarded. The cells were washed once with PBS, and then centrifuged at 400 g for 5 min to remove PBS. 100 µL of the solution of PE-conjugated anti-human Fc antibody (Jackson Immuno Research) diluted at a ratio of 1:200 was added to each well, and the cells were incubated in dark on the ice for 30 min. The cell suspension was centrifuged at 400 g for 5 min, and the supernatant was discarded. The cells were washed once with PBS. The cells were resuspended with 100 µL of PBS.

Figure 3:
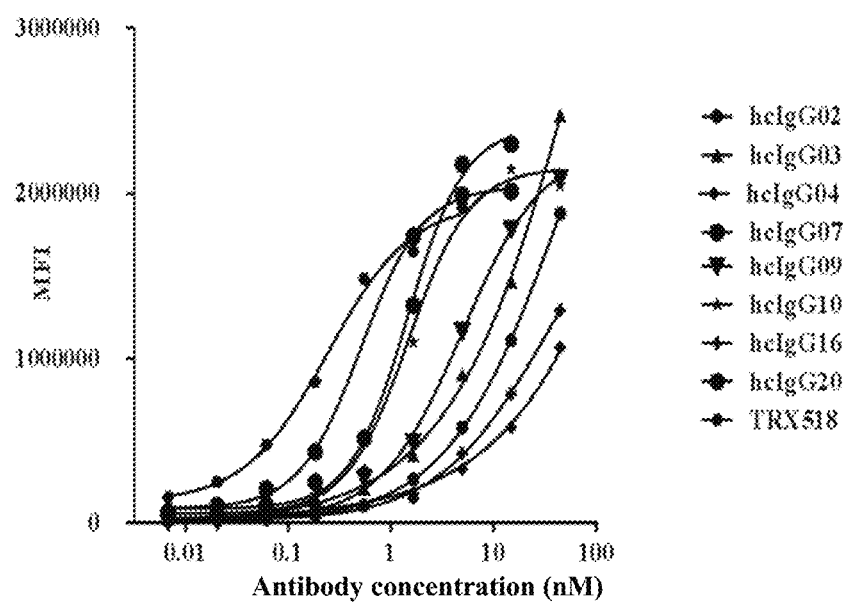
FIG. 3 shows detection results of binding of hcIgG to a cell surface GITR protein.

(3) FACS assay The detection results are shown in FIG. 3. The detected hcIgG (hcIgG-02, hcIgG-03, hcIgG-04, hcIgG-07, hcIgG-09, hcIgG-10, hcIgG-16, and hcIgG-20) all can bind to the antigen expressed on the cell surface.

3. Detection of $T_m$ for an Antibody by Differential Scanning Fluorimetry

With differential scanning fluorimetry (DSF), information about structure stability can be provided according to the process of fluorescence change in an atlas, and the configuration change of a protein can be detected. The temperature corresponding to the maximum absolute value of the fluorescence curve is the $T_m$ of the protein. In this study, the $T_m$ value of anti-GITR hcIgG was determined using the DSF method. Antibodies (hcIgG-02, hcIgG-03, hcIgG-04, hcIgG-07, hcIgG-09, hcIgG-10, hcIgG-16, and hcIgG-20) were diluted to 1 mg/mL with PBS. The SYPRO Orange protein gel stain (GIBCO) solution was 50-fold diluted with PBS, that is, 4 µL of the SYPRO Orange protein gel stain stock solution was added with 196 µL of PBS. Samples were added to a 96-well PCR plate, 50 µL diluted antibody sample+10 µL SYPRO Orange protein gel stain dilution+40 µL water. The plate was placed in a 7,500 real time PCR system for testing, and the results are shown in Table 3.

TABLE 3

Detection results of hcIgG $T_m$ values

| Antibody name | $T_m$ (° C.) | | | Average (° C.) |
|---|---|---|---|---|
| hcIgG-02 | 52.05 | 51.87 | 51.87 | 51.93 |
| | 63.02 | 63.02 | 62.83 | 62.96 |
| hcIgG-03 | 55.16 | 54.79 | 54.79 | 54.91 |
| | 61.92 | 61.74 | 61.74 | 61.80 |
| hcIgG-04 | 65.03 | 65.03 | 65.03 | 65.03 |
| hcIgG-07 | 51.50 | 51.50 | 51.32 | 51.44 |
| | 63.93 | 64.11 | 63.75 | 63.93 |
| hcIgG-09 | 63.38 | 63.20 | 63.20 | 63.26 |
| hcIgG-10 | 52.05 | 52.05 | 51.87 | 51.99 |
| | 61.74 | 61.37 | 61.37 | 61.49 |
| hcIgG-16 | 64.30 | 64.11 | 64.30 | 64.24 |
| hcIgG-20 | 62.28 | 62.28 | 62.28 | 62.28 |

Detection of ADCC Effect Mediated by hcIgG

In this experiment, antibody-dependent (cell-mediated) cytotoxicity (ADCC) mediated by hcIgG was detected with ADCC Report Bioassay kit of Promega. The effector cells used were Jurkat cells stably transfected with the NFAT-Luciferase reporter gene, and the target cells were GITR-overexpressing CHO cells (CHO-GITR). The specific experimental procedure is as follows:

The target cells were diluted to 2.5×10$^5$ cells/mL with ADCC Assay Buffer and added to each well with 50 µL/well.

25 µL of a gradient dilution of antibodies hcIgG-02, hcIgG-03, hcIgG-04, hcIgG-07, hcIgG-09, hcIgG-10, hcIgG-16, and hcIgG-20 was added (with final concentrations for each antibody of 3.33 µg/mL, 1.11 µg/mL, 0.37 µg/mL, 0.12 µg/mL, 0.041 µg/mL, 0.013 µg/mL, 0.0046 µg/mL, and 0.0015 µg/mL).

The effector cells were diluted to 1.5×10$^6$ cells/mL with ADCC Assay Buffer and added to each well with 25 µL/well.

After the mixture reacted at 37° C. for 6 h, then an equal volume of room temperature Bio-Glo Luciferase Reagent (Promega) was added to each well, and the mixture was incubated at room temperature for 10 min.

Figure 4:
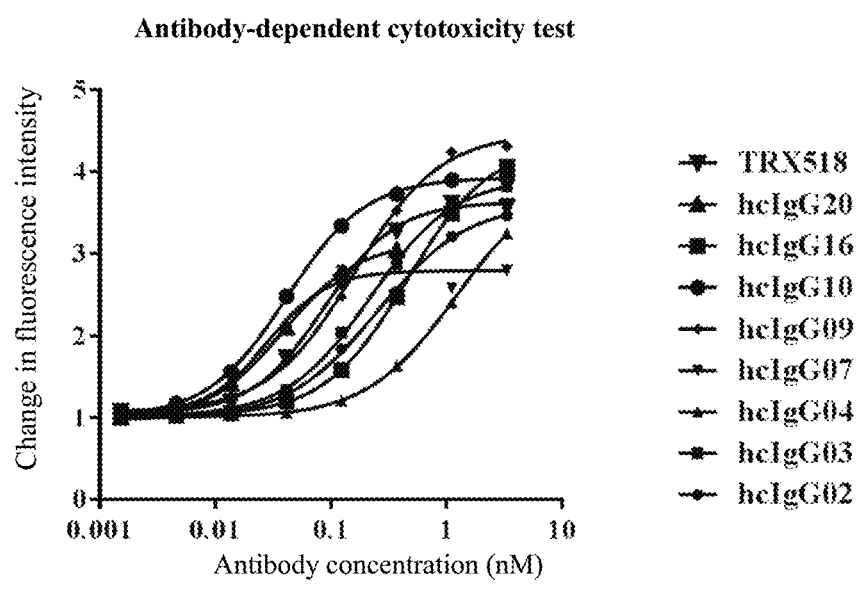
FIG. 4 shows ADCC action caused by hcIgG.

The resulting mixture was detected using GloMax Multi+ Plate Reader. The results are shown in FIG. 4. It can be seen from the curve trend in the figure that the hcIgG (hcIgG-02, hcIgG-03, hcIgG-04, hcIgG-07, hcIgG-09, hcIgG-10, hcIgG-16, and hcIgG-20) of the present invention can cause the ADCC effect.

Example 4. Humanization of Anti-GITR Heavy-Chain Antibodies

1. Humanization of hcIgG hcIgG-07 and hcIgG-20 were humanized in accordance with an existing method (Ce´cile Vincke et al., General Strategy to Humanize a Camelid Single-domain Antibody and Identification of a Universal Humanized Nanobody Scaffold. JOURNAL OF BIOLOGICAL CHEMISTRY, 2009.5 (284): 3273-3284) to obtain humanized antibodies HzhcIgG-07 and HzhcIgG-20 (see Table B for specific sequences).

2. ForteBio KD Test

In this experiment, binding kinetics and affinity for the antibody hcIgG-20 before humanization and the antibody HzhcIgG-20 after humanization were determined using the ForteBio method in the same way as in Example 3. ForteBio results are listed in Table 4. hcIgG-20 and HzhcIgG-20 retain the binding ability to GITRs, and the affinity is higher than the control antibody TRX518.

TABLE 4

Results of affinity determination of hcIgG-20 and HzhcIgG

| Antibody | Antibodies are on an AHQ tip, and the human GITR-His is in solution (100 nM) (the univalent affinity (M)) | Binding constant (1/Ms) | Dissociation constant (1/s) |
| --- | --- | --- | --- |
| TRX518 | 8.53E−09 | 3.42E+05 | 2.92E−03 |
| HzhcIgG-20 | 4.00E−09 | 3.21E+05 | 1.28E−03 |
| hcIgG-20 | 4.35E−09 | 2.11E+05 | 9.17E−04 |

3. Detection of the Binding of hcIgG to an Antigen on the Cell Surface

Figure 5:
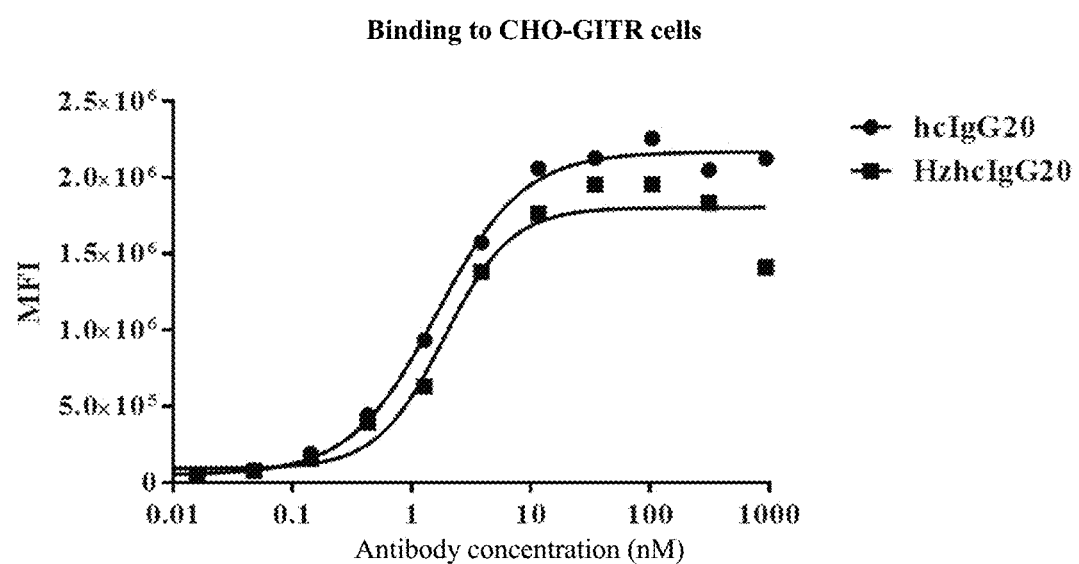
FIG. 5 shows detection results of binding of HzhcIgG to a cell surface GITR protein.

The detection method is the same as in Example 4. The detection results for cell binding by flow cytometry are shown in FIG. 5. Both hcIgG-20 and HzhcIgG-20 retain cell binding activity (EC50: 1.631 nM to 1.873 nM).

4. Detection of the Activation of hcIgG on GITR-Mediated Signaling Pathway

The wild-type Hela cells were engineered to overexpress the GITR protein on the surface. At the same time, the plasmid expressing the NF-κB binding site and the luciferase expression gene was transferred into Hela-GITR cells to obtain a stable cell line expressing both GITR and NF-κB luciferase gene (Hela-GITR-NF-κB-Luc-Rep) for detection. The activation of hcIgG-20 and HzhcIgG-20 on the NF-κB signaling pathway downstream of a GITR was detected using the cell line in this experiment. The specific experimental procedure is as follows:

Hela-GITR-NF-κB-Luc-Rep-overexpressing cells were adjusted to a cell density of $1\times10^6$ cells/mL. 150 μL of cell suspension was added to the first well, and 100 μL to other wells. Antibody was added to the first well to obtain a final concentration of 500 nM, 50 μL, of cell suspension was transferred from the first well to the next well, and the resulting solution in the next well was well mixed, and so on (with final concentrations for the antibody dilutions of 500 nM, 166.67 nM, 55.56 nM, 18.52 nM, 6.17 nM, 2.06 nM, 0.69 nM, 0.23 nM, 0.08 nM, and 0.025 nM). The plate was placed in a $CO_2$ incubator for overnight incubation.

After the plate stood at room temperature for 10 min, 80 μL of room temperature Bio-Glo Luciferase Reagent (Promega) was added to each well, and the mixture was incubated at room temperature for 5 min.

Figure 6:
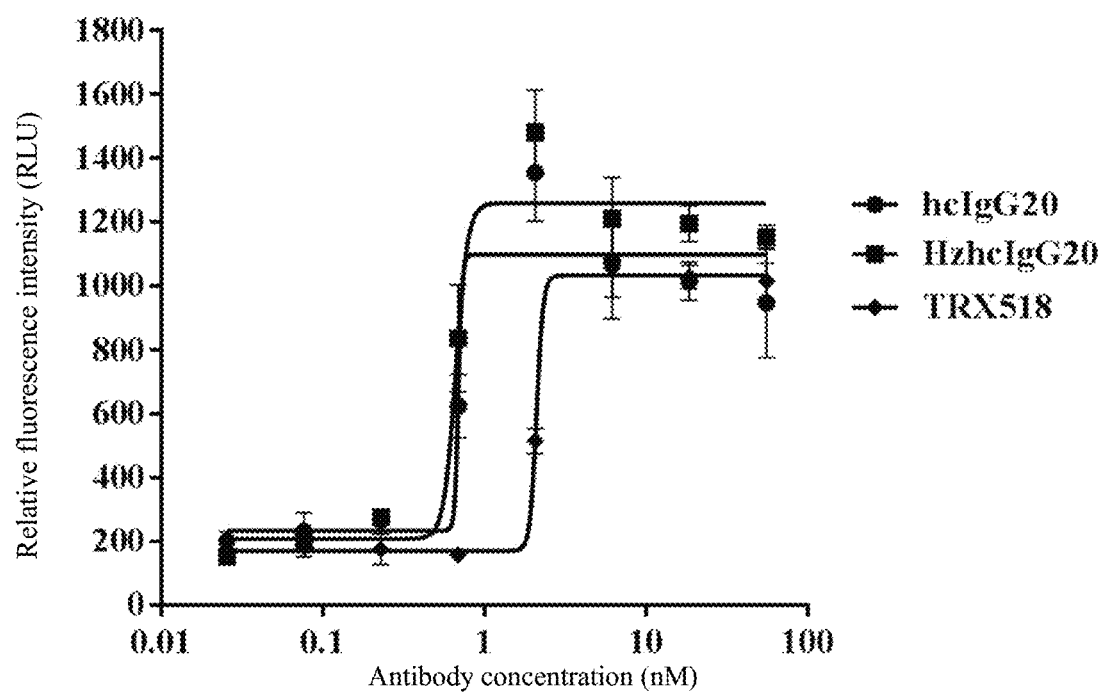
FIG. 6 shows activation of the NF-κB signaling pathway downstream of a GITR by humanized HcIgG.

The resulting mixture was detected using GloMax Multi+ Plate Reader. The detection results for cell binding by flow cytometry are shown in FIG. 6. HzhcIgG-20 has an activating effect on the NF-κB signaling pathway. The $EC_{50}$ for the activation of hcIgG-20, HzhcIgG-20 and the control antibody TRX518 are 0.6894 nM, 0.6632 nM and 2.097 nM, respectively. Both hcIgG-20 and HzhcIgG-20 are superior to the control antibody in terms of the NF-κB pathway activation ability.

Example 5. Construction and Activity Detection of Anti-GITR 4×Nb-IgG

1. Construction of 4×Nb-IgG Molecule

Figure 7:
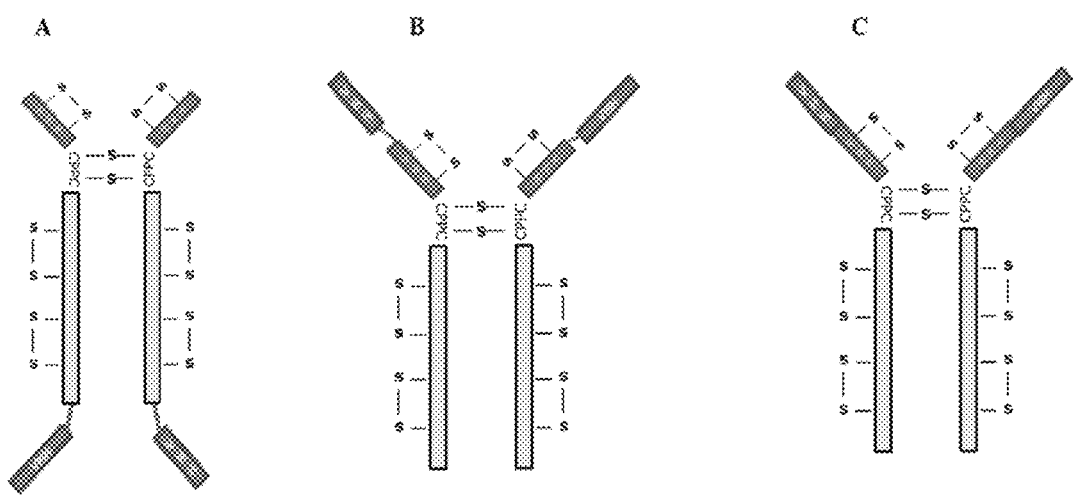
FIG. 7 is a structure diagram of 4×Nb-IgG.

Natural monoclonal antibodies can exist as polymeric structures, such as IgM, having an increased affinity for fixing a target antigen to the surface. As the agonism of TNFR requires receptor aggregation, tetravalent or hexavalent monoclonal antibodies can provide increased receptor aggregation and agonism. The antibody in a polymeric form disclosed herein contains four identical nanobody regions, and the specific construction method thereof is as follows:

4×Nb-IgG-I (VHH of HzhcIgG-20, namely, the heavy-chain variable region VH in HzhcIgG-20) was linked to C-terminus of HzhcIgG-20 via a flexible linker peptide of GGGGS (see FIG. 7A);

4×Nb-IgG-II (VHH of HzhcIgG-20) was linked to N-terminus of HzhcIgG-20 via a flexible linker peptide of GGGGS (see FIG. 7B); and 4×Nb-IgG-III (VHH of HzhcIgG-20) was directly linked to N-terminus of HzhcIgG-20 (see FIG. 7C).

The specific sequences of 4×Nb-IgG-I, 4×Nb-IgG-II and 4×Nb-IgG-III are shown in Table B.

The construct was cloned into the XhoI/NotI multiple cloning site of the expression vector pTT5.1 for HEK293 cells by a conventional method. The constructed plasmid was transfected into HEK293 cells, the 4×Nb-IgG molecules expressed and secreted by the cells were screened, and the correct molecules were isolated for further experiments.

2. Expression and Purification of 4×Nb-IgG Protein

Figure 8:
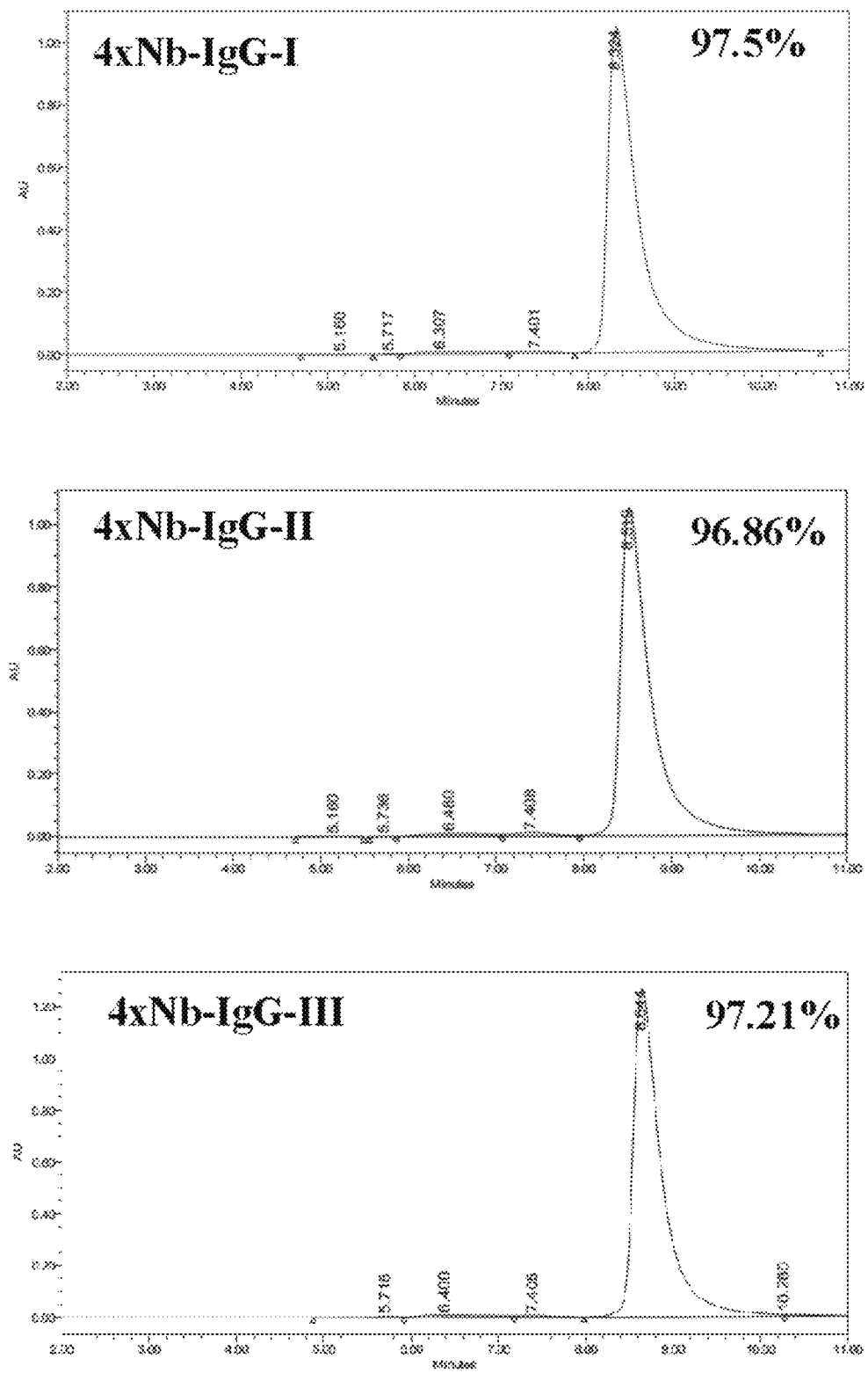
FIG. 8 shows purity results of 4×Nb-IgG after detection and purification by SEC.

The expression and purification method for 4×Nb-IgG are the same as in Example 2. The purified protein was tested for purity by SEC, and the results are shown in FIG. 8. The purities of 4×Nb-IgG-I, 4×Nb-IgG-II and 4×Nb-IgG-III after one-step affinity purification are 97.5%, 96.86%, and 97.21%, respectively.

3. ForteBio KD Test

In this experiment, kinetics and affinity for the antigen-antibody binding were determined using the ForteBio method in the same way as in Example 4. ForteBio results are shown in Table 5.

TABLE 5

| Antibody | Antibodies are on an AHQ tip, and the human GITR-His is in solution (100 nM) (the univalent affinity (M)) | Binding constant (1/Ms) | Dissociation constant (1/s) |
|---|---|---|---|
| TRX518 | 9.62E−09 | 2.14E+05 | 2.06E−03 |
| 4xNb-IgG-I | 4.60E−09 | 1.38E+05 | 6.36E−04 |
| 4xNb-IgG-II | 8.65E−09 | 7.62E+04 | 6.59E−04 |
| 4xNb-IgG-III | 6.85E−09 | 9.56E+04 | 6.55E−04 |

4. Detection of the Activation of 4xNb-IgG on GITR-Mediated Signaling Pathway

The detection method is substantially similar to that in Example 4, but optimized to reduce the antibody concentration and increase the detection sensitivity.

The experimental procedure is as follows:

Hela-GITR-NF-κB-Luc-Rep-overexpressing cells were adjusted to a cell density of $5×10^5$ cells/mL. 200 μL of cell suspension was added to the first well, and 100 μL to other wells. Antibody was added to the first well to obtain a final concentration of 10 nM, 100 μL of cell suspension was transferred from the first well to the next well, and so on (with final concentrations for the antibody dilutions of 10 nM, 5.00 nM, 2.50 nM, 1.25 nM, 0.63 nM, 0.31 nM, 0.16 nM, 0.08 nM, 0.04 nM, 0.02 nM, and 0.01 nM). The plate was placed in a $CO_2$ incubator for 7 h of incubation.

After the plate stood at room temperature for 10 min, 80 μL of room temperature Bio-Glo Luciferase Reagent (Promega) was added to each well, and the mixture was incubated at room temperature for 5 min.

Figure 9:
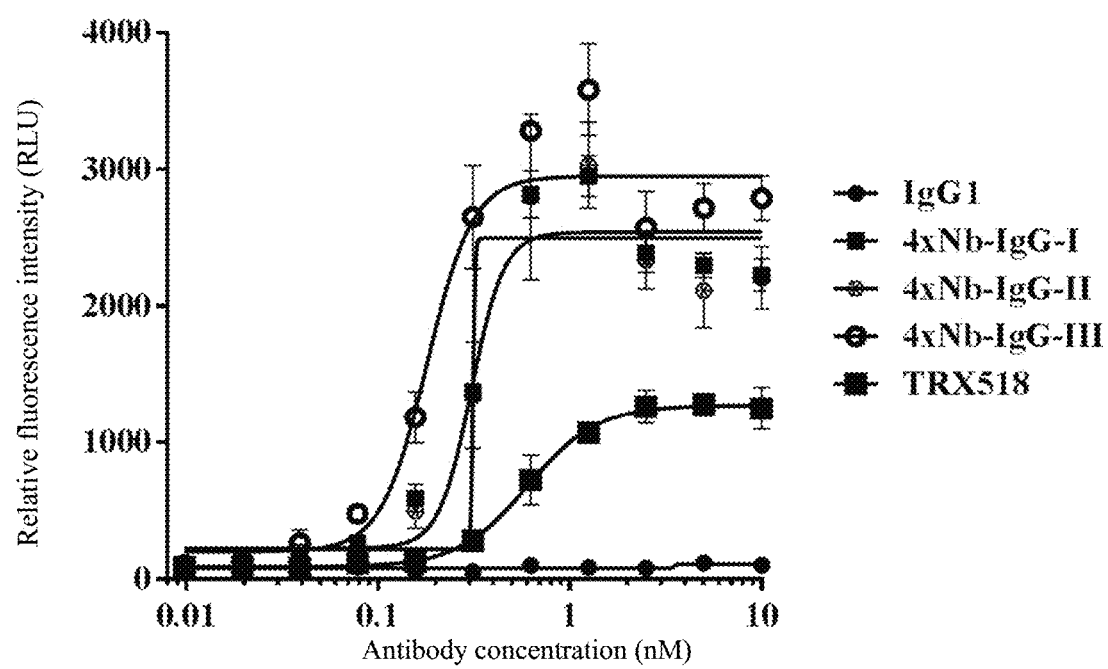
FIG. 9 shows activation of the NF-κB signaling pathway downstream of a GITR by 4×Nb-IgG.
Figure 10:
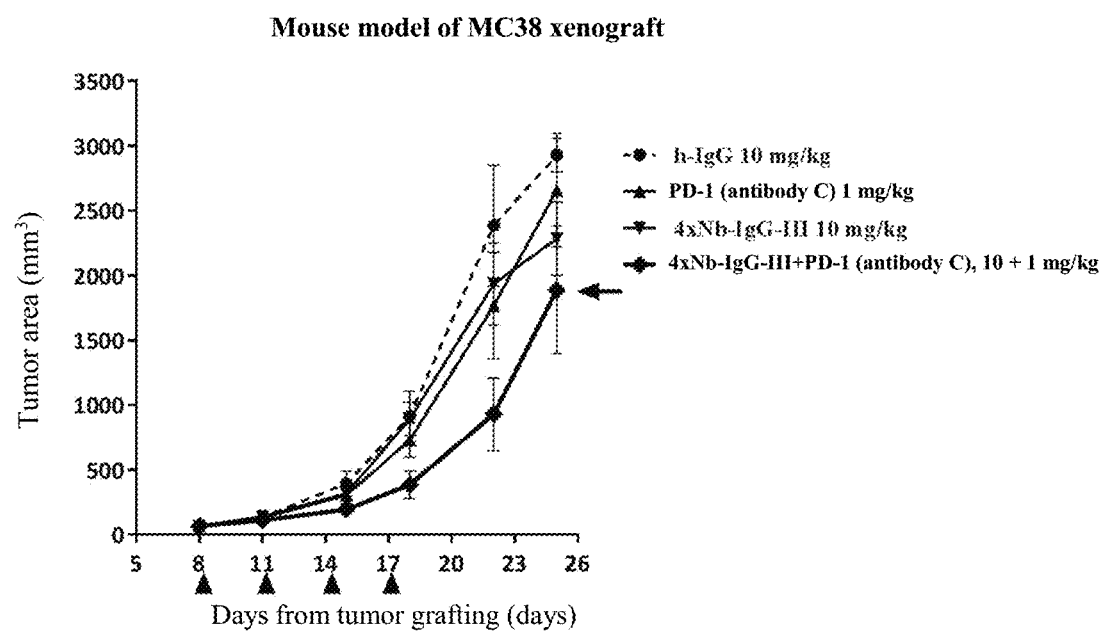
FIG. 10 shows inhibition of tumor in an MC38 transplanted tumor model by an anti-GITR antibody (4×Nb-IgG) alone or in combination with an anti-PD-1 antibody.

The resulting mixture was detected using GloMax Multi+ Plate Reader. The results are shown in FIG. 9, 4xNb-IgG-I, 4xNb-IgG-II and 4xNb-IgG-III all exhibit a stronger activation activity than the positive control.

5. Anti-Tumor Activity of Anti-GITR Antibodies Disclosed Herein

The anti-tumor activity of the anti-human GITR antibody 4xNb-IgG-III alone or in combination with the anti-mouse PD-1 antibody "Antibody C" (WO2017/133540) was studied using a mouse model of MC38 transplantation tumor.

Mice: male human GITR transgenic mice (approximately 8 weeks old), purchased from Biocytogen. Before the study, the mice were adapted for 7 days after arrival.

Cells: mouse colon cancer cells MC38 (ATCC), purchased from ATCC. The cells were subcultured strictly according to the requirement provided by ATCC for further in-vivo assays. The cells were collected by centrifugation and resuspended in sterile PBS, with the cell density adjusted to $5×10^6$ cells/mL. On day 0, 0.2 mL of the cell suspension was subcutaneously inoculated into the right abdominal region of the human GITR transgenic mice to establish tumor-bearing mouse models.

Administration: Mice were divided into four groups (8 mice per group) and each group was injected subcutaneously with the following doses of antibodies:
(1) mouse IgG control (equitech-Bio), 10 mg/kg;
(2) PD-1 (Antibody C), 1 mg/kg;
(3) 4xNb-IgG-III, 10 mg/kg; and
(4) 4xNb-IgG-III, 10 mg/kg PBS+PD-1 (Antibody C), 1 mg/kg.

Injection: On day 8 after inoculation, the mice meeting the experimental requirements were randomly grouped, 6 mice per group. The mice in each group were administrated with the four regimens on Days 8, 11, 14 and 17 at the above doses respectively.

Analysis: The tumor volume and body weight were measured twice a week throughout the study, and the mice were euthanized when the tumors reached the endpoint or when the mice had more than 20% of weight loss. The maximum length of major axis (L) and the maximum length of minor axis (W) of tumors were measured with a vernier caliper, and tumor volume was calculated using the following formula: $V=L×W^2/2$. The tumor volume over time of the mice in various groups was plotted. Statistical significance was determined using analysis of variance (ANOVA). A P value below 0.05 was considered statistically significant in all analyses.

Results are shown in Table 10.

As shown, compared with the IgG control (equitech-Bio), the anti-GITR antibody 4xNb-IgG-III disclosed herein can significantly inhibit the tumor growth; and the anti-GITR antibody 4xNb-IgG-III disclosed herein used in combination with the anti-PD-1 monoclonal antibody "Antibody C" can significantly inhibit the tumor growth, compared with IgG and these two antibodies separately used alone.

The invention claimed is:

1. A heavy chain antibody or a variable domain thereof specifically binding to a glucocorticoid-induced tumor necrosis factor receptor (GITR), characterized in that it comprises HCDR1, HCDR2 and HCDR3, wherein the HCDR1, HCDR2 and HCDR3 are the HCDR1, HCDR2 and HCDR3 as comprised in heavy chain variable region consisting of the sequence selected from the group consisting of SEQ ID NO: 65, 66, 67, 70, 72, 73, 79, 83, 124 and 125.

2. A fusion protein, comprising the heavy chain antibody or a variable domain thereof of claim 1 and a second molecule.

3. An immunoconjugate, a composition or a kit, comprising the heavy chain antibody or a variable domain thereof of claim 1.

4. An isolated nucleic acid, encoding the heavy chain antibody or a variable domain thereof of claim 1.

5. An expression vector comprising the nucleic acid of claim 4.

6. A host cell comprising the expression vector of claim 5.

7. A method for preparing the heavy chain antibody or a variable domain thereof of claim 1, comprising cultivating a host cell comprising a nucleic acid encoding the heavy chain antibody or a variable domain thereof of claim 1 under a condition suitable for expressing the heavy chain antibody or a variable domain thereof.

8. A pharmaceutical composition, comprising the heavy chain antibody or a variable domain thereof of claim 1, and a pharmaceutical carrier.

9. A method for detecting the presence of GITRs in a sample, comprising:
    (a) contacting a sample with the isolated heavy chain antibody or a variable domain thereof of claim 1; and
    (b) detecting formation of a complex of the heavy chain antibody or a variable domain thereof with GITR proteins.

10. A method for treating cancer, inducing or enhancing an immune response in an individual with cancer, and/or stimulating an antigen-specific T cell response in an individual with cancer, comprising administering to the individual with cancer an effective amount of the heavy chain antibody or a variable domain thereof of claim 1.

11. The heavy chain antibody or a variable domain thereof of claim 1, wherein the HCDR3 comprises or consists of the sequence selected from the group consisting of SEQ ID NOs: 46, 47, 48, 51, 53, 57 and 61.

12. The heavy chain antibody or a variable domain thereof of claim 1, wherein the sequences of HCDR1, HCDR2 and HCDR3 are:
    (1) SEQ ID NO: 2, SEQ ID NO: 24 and SEQ ID NO: 46;
    (2) SEQ ID NO: 3, SEQ ID NO: 25 and SEQ ID NO: 47;
    (3) SEQ ID NO: 4, SEQ ID NO: 26 and SEQ ID NO: 48;
    (4) SEQ ID NO: 7, SEQ ID NO: 29 and SEQ ID NO: 51;
    (5) SEQ ID NO: 9, SEQ ID NO: 31 and SEQ ID NO: 53;
    (6) SEQ ID NO: 10, SEQ ID NO: 32 and SEQ ID NO: 51;
    (7) SEQ ID NO: 16, SEQ ID NO: 38 and SEQ ID NO: 57; or
    (8) SEQ ID NO: 20, SEQ ID NO: 42 and SEQ ID NO: 61.

13. The heavy chain antibody or a variable domain thereof of claim 1, which comprises a heavy chain variable region, which comprises or consists of
    (1) the sequence shown in any one of SEQ ID NOs: 65, 66, 67, 70, 72, 73, 79, 83, 124, and 125;
    (2) the sequence which has at least 90% or more sequence identity with the sequence shown in any one of SEQ ID NOs: 65, 66, 67, 70, 72, 73, 79, 83, 124 and 125; or
    (3) the sequence having 1 to 10 amino acid alterations selected from the group consisting of substitution, deletion or insertion, relative to the sequence set forth in any one of SEQ ID NOs: 65, 66, 67, 70, 72, 73, 79, 83, 124 and 125, wherein the amino acid alterations are not present in the CDR regions.

14. The heavy chain antibody or a variable domain thereof of claim 1, wherein the heavy chain antibody or a variable domain thereof is humanized.

15. The heavy chain antibody of claim 1, comprising a heavy chain variable region and an Fc fragment, wherein the Fc fragment comprises or consists of one of the following sequences (a)-(d):
    (a) an Fc fragment of human IgG1;
    (b) an Fc fragment set forth in SEQ ID NO: 121;
    (c) an Fc fragment having at least 90% or more sequence identity with an Fc fragment set forth in SEQ ID NO: 121; or
    (d) an Fc fragment having 1 to 10 amino acid substitutions, deletions or insertions relative to an Fc fragment set forth in SEQ ID NO: 121.

16. A polymeric form of the heavy chain antibody or a variable domain thereof of claim 1.

17. The polymeric form of the heavy chain antibody of claim 16, wherein the heavy chain antibody is a humanized heavy chain antibody.

18. The polymeric form of the heavy chain antibody or a variable domain thereof of claim 16, which is a tetrameric or hexameric form of the heavy chain antibody or a variable domain thereof.

19. The polymeric form of the heavy chain antibody or a variable domain thereof of claim 16, which comprises:
    (1) the sequence as shown in anyone of SEQ ID NOs: 118-120; or
    (2) the sequence having at least 90% or more identity with the sequence as shown in any one of SEQ ID NOs: 118-120.

20. The polymeric form of the heavy chain antibody or a variable domain thereof of claim 16, which consists of:
    (1) two, three or more identical sequences as shown in any one of SEQ ID NOs: 118-120: or
    (2) two, three or more identical sequences having at least 90% or more identity with the sequence as shown in any one of SEQ ID NOs: 118-120.

21. The fusion protein of claim 2, wherein the second molecule is selected from a protein, a polypeptide, a marker, a drug, or a cytotoxic agent.

22. An immunoconjugate, a composition or a kit, comprising the heavy chain antibody or a variable domain thereof of claim 12.

23. A pharmaceutical composition, comprising the heavy chain antibody or a variable domain thereof of claim 12.

24. A method for treating cancer, inducing or enhancing an immune response in an individual with cancer, and/or stimulating an antigen-specific T cell response in an individual with cancer, comprising administering to the individual with cancer an effective amount of the heavy chain antibody or a variable domain thereof of claim 12.

25. A bispecific or multi-specific antibody comprising the heavy chain antibody of or a variable domain thereof of claim 1.

* * * * *

SEQUENCE LISTING

<160> NUMBER OF SEQ ID NOS: 127

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Leu Thr Phe Asp Asp Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Asp Thr Tyr Thr Arg Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Thr Tyr Ser Gly Tyr Cys
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Val Asp Asp Ser Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Thr Phe Ser Asn Lys Val
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Ala Tyr Thr Arg Asn Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Gly Phe Ala Phe Gly Ser Ser His
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Tyr Thr Ser Ser Arg Lys Tyr Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Phe Thr Phe Ser Ser Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Ala Phe Gly Ser Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Thr Phe Asp Ala Ala
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Asp Thr Tyr Thr Arg Tyr Phe
1               5

<210> SEQ ID NO 13
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Asn Thr Gly Arg
1

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Thr Phe Ser Asn Tyr Cys
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Ile Phe Arg Asn Tyr Cys
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Tyr Thr Tyr Asn Lys Tyr Ser
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Tyr Thr Ser Ser Ser Asn Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Leu Thr Ser Thr Thr Lys Tyr
1               5
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Tyr Ser Asn Tyr Cys
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Ser Arg Thr Ser Arg Trp
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Thr Asn Asn Leu Lys Ser
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Tyr Thr Phe Thr Thr Ala Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Trp Ser Gly Ser Ser Thr Tyr
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 24

Val Leu Leu Pro Gly Gly Asp Tyr Thr Phe
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Ile Val Ser Gly Leu Gly Arg Pro
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Thr Ile Ser Ser Asp Gly Ser Thr Tyr
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Gly Gly Asp Trp Thr Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Leu Gly Gly Gly Ser Thr Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

His Ser Gly Gly Gly Phe Gly Asp
1               5

<210> SEQ ID NO 30
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Thr Gly Ala Gly Gly Thr Cys
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Ser Asp Val Ser Gly Thr Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Gly Gly Gly Phe Gly Asp
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Ser Asp Gly Ser Thr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Pro Gly Gly Ala Tyr Thr Phe
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asn Phe Gly Arg Thr Asn
```

```
<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ile Phe Val Asp Gly Ser Thr Arg
1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Ile Tyr Thr Gly Gly Gly Ser Thr Tyr
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ile Asp Ser Asp Gly Ser Thr Ser
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Thr Gly Ala Gly Ile Thr Cys
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Tyr Ile Ser Ser Gly Ala Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 41

Asp Ser Asp Gly Ser Thr Ser
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Thr Gly Gly Ser Ser Thr Leu
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Asn Asn Gly Gly Pro Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ser Asp Gly Arg Thr Glu
1               5

<210> SEQ ID NO 45
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Pro Arg Ser Gly Gly Tyr Tyr Ser Pro Pro Pro Pro Ala Val
1               5                   10                  15

Tyr Arg Tyr Leu Arg Phe
            20

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Val Thr Val Gly Ser Arg Trp Ser Gln Ala Ser Asn Tyr Asn Tyr
1               5                   10                  15

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Trp Ala Thr Lys Leu Cys Ser Glu Ile Pro Ala Thr Glu Trp Asp
1               5                   10                  15

Tyr

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Arg Val Gly Val Gly Trp Val Arg Pro Cys Asp Tyr Glu Tyr Asn
1               5                   10                  15

Tyr

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Glu Asn Trp Lys Thr Pro
1               5

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Ala Gln Tyr Gly Gly Ser Leu Cys Ser Asn Phe Gly Trp Tyr Asn
1               5                   10                  15

Leu

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Thr Asp Trp Arg Lys Pro
1               5

<210> SEQ ID NO 52

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Trp Val Arg Gly Gly Phe Cys Ser Gly Asp Ala Asp Phe Arg Tyr
1               5                   10                  15

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Cys Gly Phe Ser Gly Gly Thr Trp Ser Cys Lys Tyr
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Pro Trp Gly Arg Gly Ala Ala Leu Thr Pro Asn Glu Tyr Ile Tyr
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Phe Pro Trp Thr Leu Cys Val Asp Gly Pro Gly Ala Tyr Lys Tyr
1               5                   10                  15

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Gln Thr Thr Arg Tyr Ser Ser Asp Tyr Val Asn Val Gly Pro Cys
1               5                   10                  15

Asp Met Asp Ser
            20

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 57

Ser Asp Trp Val Ser Ala Ile Gln Ala Leu Gly Val Leu Ala Val Arg
1               5                   10                  15

Pro Tyr Glu Tyr
            20

<210> SEQ ID NO 58
<211> LENGTH: 16
<212> TYPE: PRT
<213> ORGANIZM: Artificial Sequence
<220> FEATURE:
<223> OTHER INFORMATION: Description of Artificial Sequence: Synthetic
      peptide

<400> SEQUENCE: 58

Asp Trp Phe Arg Gly Ala Phe Cys Ser Gly Asp Ala Asp Phe Arg Tyr
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Val Leu Ser Val Phe Arg Pro Leu Ser Ser Asn Gln Tyr His Tyr
1               5                   10                  15

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Asn Lys Lys Pro Tyr Gln Leu Cys Asn Thr Asp Ser Arg Arg Tyr
1               5                   10                  15

Tyr His

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Lys Leu Ala Gly Asp Phe Trp Leu Val Asp Arg Trp Arg Ala
1               5                   10                  15

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Asn Arg Phe Leu Gly Ser Gly Ser Trp Arg Leu Pro Ser Leu Tyr

Asn Tyr

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Lys Asp Asp Trp Leu Leu Leu His Gly Arg Ser Leu Phe Pro Ser
1               5                   10                  15

Ala Phe Ala Tyr
            20

<210> SEQ ID NO 64
<211> LENGTH: 131
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Val Gln Leu Gln Glu Ser Gly Gly Gly Leu Val Gln Pro Gly Gly
1               5                   10                  15

Ser Leu Arg Leu Ser Cys Thr Ala Ser Gly Leu Thr Phe Asp Asp Tyr
            20                  25                  30

Ala Met Gly Trp Phe Arg Gln Ala Pro Gly Lys Gly Arg Glu Gly Val
        35                  40                  45

Ser Leu Ile Thr Trp Ser Gly Ser Thr Tyr Tyr Ala Asp Ser Val
    50                  55                  60

Lys Gly Arg Phe Thr Val Ser Arg Asp Thr Ala Thr Asn Thr Leu Val
65                  70                  75                  80

Leu Gln Met Asn Ser Leu Lys Pro Glu Asp Thr Ala Met Tyr Tyr Cys
                85                  90                  95

Ala Ala Asp Pro Arg Ser Gly Gly Tyr Tyr Ser Ser Pro Pro Pro Pro
            100                 105                 110

Ala Val Tyr Arg Tyr Leu Arg Phe Trp Gly Gln Gly Thr Gln Val Thr
        115                 120                 125

Val Ser Ser
    130

<210> SEQ ID NO 65
<211> LENGTH: 125
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Val Gln Leu Gln Glu Ser Gly Gly Gly Ser Val Gln Ala Gly Gly
1               5                   10                  15

Ser Leu Arg Leu Ser Cys Ala Ala Ser Arg Asp Thr Tyr Thr Arg Tyr
            20                  25                  30

Phe Met Gly Trp Phe Arg Gln Thr Pro Gly Lys Glu Gly Glu Gly Val
        35                  40                  45

Ala Val Leu Leu Pro Gly Gly Asp Tyr Thr Phe Tyr Ala Asp Ser Val
    50                  55                  60

Lys Gly Arg Phe Thr Ile Thr Gln Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Asp Val Thr Val Gly Ser Arg Trp Ser Gln Ala Ser Asn Tyr
            100                 105                 110

Asn Tyr Trp Gly Gln Gly Thr Gln Val Thr Val Ser Ser
        115                 120                 125

<210> SEQ ID NO 66
<211> LENGTH: 126
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Gly Tyr
            20                  25                  30

Cys Met Gly Trp Phe Arg Gln Ala Pro Gly Lys Glu His Glu Gly Val
        35                  40                  45

Ala Ser Ile Val Ser Gly Leu Gly Arg Pro Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Glu Trp Ala Thr Lys Leu Cys Ser Glu Ile Pro Ala Thr Glu
            100                 105                 110

Trp Asp Tyr Trp Gly Gln Gly Thr Gln Val Thr Val Ser Ser
        115                 120                 125

<210> SEQ ID NO 67
<211> LENGTH: 125
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Val Asp Asp Ser
            20                  25                  30

Gly Met Gly Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Pro Arg Val Gly Val Gly Trp Val Arg Pro Cys Asp Tyr Glu Tyr
            100                 105                 110

Asn Tyr Trp Gly Gln Gly Thr Gln Val Thr Val Ser Ser
        115                 120                 125

<210> SEQ ID NO 68
<211> LENGTH: 116
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Lys
            20                  25                  30

Val Met Ser Trp Val Arg Gln Ala Pro Gly Lys Gly Phe Glu Trp Val
        35                  40                  45

Ser Ser Ile Ala Arg Gly Gly Asp Trp Thr Thr Tyr Ala Asp Ser Val
    50                  55                  60

Glu Gly Arg Phe Thr Ile Ser Arg Asp Asn Ala Lys Asn Thr Leu Tyr
65                  70                  75                  80

Leu Gln Leu Asn Ser Leu Lys Thr Glu Asp Thr Ala Met Tyr Tyr Cys
                85                  90                  95

Ala Gln Ala Glu Asn Trp Lys Thr Pro Pro Gly Gln Gly Thr Gln Val
            100                 105                 110

Thr Val Ser Ser
        115

<210> SEQ ID NO 69
<211> LENGTH: 126
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ala Tyr Thr Arg Asn
            20                  25                  30

Cys Met Gly Trp Phe Arg Gln Ala Pro Gly Lys Glu Arg Glu Val
        35                  40                  45

Ala Thr Ile Asn Leu Gly Gly Ser Thr Tyr Tyr Ala Asp Ser Val
    50                  55                  60

Lys Gly Arg Phe Ala Ile Ser Gln Asp Asn Ala Lys Asn Thr Val Tyr
65                  70                  75                  80

Leu Gln Met Asn Asn Leu Lys Pro Glu Asp Thr Ala Met Tyr Tyr Cys
                85                  90                  95

Ala Ala Ile Ala Gln Tyr Gly Gly Ser Leu Cys Ser Asn Phe Gly Trp
            100                 105                 110

Tyr Asn Leu Trp Gly Gln Gly Thr Gln Val Thr Val Ser Ser
        115                 120                 125

<210> SEQ ID NO 70
<211> LENGTH: 116

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Val Gln Leu Gln Glu Ser Gly Gly Gly Leu Val Gln Ala Gly Gly
1               5                   10                  15

Ser Leu Lys Leu Ser Cys Thr Val Ser Gly Phe Ala Phe Gly Ser Ser
            20                  25                  30

His Met Ser Trp Val Arg Arg Ala Pro Gly Lys Gly Leu Glu Trp Val
        35                  40                  45

Ser Thr Ile His Ser Gly Gly Phe Gly Asp Tyr Ala Asn Ser Val
    50                  55                  60

Gln Gly Arg Phe Thr Ile Ser Arg Asp Val Ala Lys Asn Thr Leu Tyr
65                  70                  75                  80

Leu Gln Met Asn Ser Leu Lys Pro Glu Asp Thr Ala Ile Tyr Tyr Cys
                85                  90                  95

Ala Leu Ala Thr Asp Trp Arg Lys Pro Pro Gly Gln Gly Thr Gln Val
            100                 105                 110

Thr Val Ser Ser
            115

<210> SEQ ID NO 71
<211> LENGTH: 125
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Ser Ser Arg Lys
            20                  25                  30

Tyr Ile Gly Trp Phe Arg Gln Ala Pro Gly Lys Gln Arg Glu Trp Val
        35                  40                  45

Ala Gly Ile Asp Thr Gly Ala Gly Gly Thr Cys Thr Ile Ala Ser Val
    50                  55                  60

Gln Gly Arg Phe Thr Ile Ser Gln Asp Val Ala Lys Asn Thr Leu Tyr
65                  70                  75                  80

Leu Gln Ile Asp Ser Leu Lys Pro Glu Asp Thr Ala Val Tyr Tyr Cys
                85                  90                  95

Ala Ala Asp Trp Val Arg Gly Gly Phe Cys Ser Gly Asp Ala Asp Phe
            100                 105                 110

Arg Tyr Trp Gly Gln Gly Thr Gln Val Thr Val Ser Ser
    115                 120                 125

<210> SEQ ID NO 72
<211> LENGTH: 122
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Val Gln Leu Gln Glu Ser Gly Gly Gly Leu Val Gln Pro Gly Gly
```

```
                 1               5                  10                 15
Ser Leu Arg Leu Ser Cys Gly Ala Ser Gly Phe Thr Phe Ser Ser Thr
                20                 25                 30
Ala Met Trp Trp Phe Arg Gln Ala Pro Gly Lys Gly Leu Glu Trp Val
                35                 40                 45
Ser Ser Ile Thr Ser Asp Val Ser Gly Thr Tyr Tyr Ala Asp Ser Val
 50                 55                 60
Gln Gly Arg Phe Thr Ile Ser Arg Asp Asn Gly Lys Asn Thr Val Tyr
65                  70                 75                  80
Leu Gln Met Asn Ser Leu Arg Ser Glu Asp Thr Ala Leu Tyr Tyr Cys
                85                 90                 95
Ala Thr Ser Cys Gly Phe Ser Gly Gly Thr Trp Ser Cys Lys Tyr Arg
                100                105                110
Gly Gln Gly Thr Gln Val Thr Val Ser Ser
                115                120
```

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

```
Gln Val Gln Leu Gln Glu Ser Gly Gly Gly Leu Val Gln Pro Gly Gly
1               5                  10                 15
Ser Leu Arg Leu Ser Cys Ala Ala Ser Gly Phe Ala Phe Gly Ser Ser
                20                 25                 30
His Met Ser Trp Val Arg Arg Ala Pro Gly Lys Gly Leu Glu Trp Val
                35                 40                 45
Ser Thr Ile His Ser Gly Gly Phe Gly Asp Tyr Ala Asn Ser Val
 50                 55                 60
Gln Gly Arg Phe Thr Ile Ser Arg Asp Val Ala Lys Asn Thr Leu Tyr
65                  70                 75                  80
Leu Gln Met Asn Ser Leu Lys Pro Glu Asp Thr Ala Ile Tyr Tyr Cys
                85                 90                 95
Ala Leu Ala Thr Asp Trp Arg Lys Pro Pro Gly Gln Gly Thr Gln Val
                100                105                110
Thr Val Ser Ser
        115
```

<210> SEQ ID NO 74
<211> LENGTH: 125
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

```
Gln Val Gln Leu Gln Glu Ser Gly Gly Gly Ser Val Gln Thr Gly Gly
1               5                  10                 15
Ser Leu Arg Leu Ser Cys Thr Ala Ser Gly Phe Thr Phe Asp Ala Ala
                20                 25                 30
Asp Met Gly Trp Tyr Arg Gln Ala Pro Gly Asn Glu Cys Glu Leu Val
                35                 40                 45
Ser Ile Ile Ser Ser Asp Gly Ser Thr Tyr Tyr Ala Asp Ser Val Lys
```

```
                    50                  55                  60
Gly Arg Phe Thr Ile Ser Gln Asp Asn Ala Lys Asn Thr Val Tyr Leu
 65                  70                  75                  80

Gln Met Asn Ser Leu Lys Pro Glu Asp Thr Ala Val Tyr Tyr Cys Ala
                 85                  90                  95

Ala Pro Arg Val Gly Val Gly Trp Val Arg Pro Cys Asp Tyr Glu Tyr
            100                 105                 110

Asn Tyr Trp Gly Gln Gly Thr Gln Val Thr Val Ser Ser
        115                 120                 125

<210> SEQ ID NO 75
<211> LENGTH: 125
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Val Gln Leu Gln Glu Ser Gly Gly Gly Ser Val Gln Ala Gly Gly
  1               5                  10                  15

Ser Leu Arg Leu Ser Cys Ala Ala Ser Arg Asp Thr Tyr Thr Arg Tyr
             20                  25                  30

Phe Met Gly Trp Phe Arg Gln Thr Pro Gly Lys Glu Pro Glu Gly Val
         35                  40                  45

Ala Val Leu Leu Pro Gly Gly Ala Tyr Thr Phe Tyr Ala Asp Ser Val
     50                  55                  60

Lys Gly Arg Phe Thr Ile Thr Gln Asp Ser Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Asp Val Thr Val Gly Ser Arg Trp Ser Gln Ala Ser Asn Tyr
            100                 105                 110

Asn Tyr Trp Gly Gln Gly Thr Gln Val Thr Val Ser Ser
        115                 120                 125

<210> SEQ ID NO 76
<211> LENGTH: 121
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Val Gln Leu Gln Glu Ser Gly Gly Gly Ser Val Gln Ala Gly Gly
  1               5                  10                  15

Ser Leu Arg Leu Ser Cys Thr Ala Ser Ser Asn Thr Gly Arg Met Gly
             20                  25                  30

Trp Phe Arg Gln Ala Pro Gly Lys Glu Arg Glu Gly Val Thr Ala Val
         35                  40                  45

Asp Asn Phe Gly Arg Thr Asn Tyr Ala Lys Tyr Val Lys Gly Arg Phe
     50                  55                  60

Thr Ile Ser Lys Asp Asn Ala Lys Asn Thr Leu Tyr Leu Gln Met Asn
 65                  70                  75                  80

Ser Leu Lys Pro Glu Asp Thr Ala Met Tyr Tyr Cys Ala Ala Asp Pro
                 85                  90                  95

Trp Gly Arg Gly Ala Ala Leu Thr Pro Asn Glu Tyr Ile Tyr Trp Gly
```

```
                100                 105                 110
Gln Gly Thr Gln Val Thr Val Ser Ser
        115                 120

<210> SEQ ID NO 77
<211> LENGTH: 124
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Val Gln Leu Gln Glu Phe Gly Gly Gly Ser Val Gln Ala Gly Gly
1               5                   10                  15

Ser Leu Arg Leu Ser Cys Val Ala Ser Gly Phe Thr Phe Ser Asn Tyr
            20                  25                  30

Cys Met Gly Trp Phe Arg Gln Asp Pro Gly Lys Glu Arg Glu Ala Val
        35                  40                  45

Ala Arg Ile Phe Val Asp Gly Ser Thr Arg Tyr Ala Asp Ala Val Lys
    50                  55                  60

Gly Arg Phe Thr Ile Ser Lys Asp Asn Ala Lys Asn Thr Leu Tyr Val
65                  70                  75                  80

Gln Ile Asn Ser Leu Lys Pro Glu Asp Thr Ala Met Tyr Tyr Cys Thr
                85                  90                  95

Thr Pro Phe Pro Trp Thr Leu Cys Val Asp Gly Pro Gly Ala Tyr Lys
            100                 105                 110

Tyr Trp Gly Gln Gly Thr Gln Val Thr Val Ser Ser
        115                 120

<210> SEQ ID NO 78
<211> LENGTH: 129
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Val Gln Leu Gln Glu Ser Gly Gly Gly Ser Val Gln Ala Gly Gly
1               5                   10                  15

Ser Leu Arg Leu Ser Cys Val Val Phe Gly Asn Ile Phe Arg Asn Tyr
            20                  25                  30

Cys Met Ala Trp Phe Arg Gln Ala Pro Gly Lys Glu Arg Glu Gly Val
        35                  40                  45

Val Val Ile Tyr Thr Gly Gly Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys His Glu Asp Thr Ala Met Tyr Tyr Cys
                85                  90                  95

Ala Ala Asp Gln Thr Thr Arg Tyr Ser Ser Tyr Val Asn Val Gly
            100                 105                 110

Pro Cys Asp Met Asp Ser Trp Gly Lys Gly Thr Gln Val Thr Val Ser
        115                 120                 125

Ser

<210> SEQ ID NO 79
```

<211> LENGTH: 128
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Asn Lys Tyr
                20                  25                  30

Ser Trp Gly Trp Phe Arg Gln Ala Pro Gly Lys Glu Arg Glu Gly Val
            35                  40                  45

Ala Gly Ile Asp Ser Asp Gly Ser Thr Ser Tyr Ala Asp Ser Val Lys
        50                  55                  60

Gly Arg Phe Thr Ile Ser Lys Asp Asn Thr Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Ser Asp Trp Val Ser Ala Ile Gln Ala Leu Gly Val Leu Ala Val
            100                 105                 110

Arg Pro Tyr Glu Tyr Trp Gly Gln Gly Thr Gln Val Thr Val Ser Ser
        115                 120                 125

<210> SEQ ID NO 80
<211> LENGTH: 125
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Val Gln Leu Gln Glu Ser Gly Gly Gly Ser Ala Gln Ala Gly Gly
1               5                   10                  15

Ser Leu Arg Leu Ser Cys Ala Ala Ser Arg Tyr Thr Ser Ser Ser Asn
                20                  25                  30

Ala Met Gly Trp Phe Arg Gln Ala Pro Gly Lys Gln Arg Glu Trp Val
            35                  40                  45

Ala Gly Ser Asp Thr Gly Ala Gly Ile Thr Cys Asn Ala Ala Ser Val
        50                  55                  60

Lys Gly Arg Phe Thr Ile Ser Gln Asp Val Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Trp Phe Arg Gly Ala Phe Cys Ser Gly Asp Ala Asp Phe
            100                 105                 110

Arg Tyr Trp Gly Gln Gly Thr Gln Val Thr Val Ser Ser
        115                 120                 125

<210> SEQ ID NO 81
<211> LENGTH: 125
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

```
Gln Val Gln Leu Gln Glu Ser Gly Gly Gly Ser Val Gln Thr Gly
1               5                   10                  15

Ser Leu Arg Leu Ser Cys Ala Ala Ser Gly Leu Thr Thr Thr Lys
            20                  25                  30

Tyr Met Gly Trp Phe Arg Gln Ala Pro Gly Lys Glu Arg Glu Gly Val
            35                  40                  45

Ala Gly Ile Tyr Ile Ser Ser Gly Ala Thr Tyr Tyr Asp Asp Ser Val
        50                  55                  60

Lys Gly Arg Phe Thr Ile Ser Gln Asp Asn Ala Lys Asn Thr Val Tyr
65                  70                  75                  80

Leu His Ile Asn Ser Leu Glu Pro Asp Asp Thr Ala Met Tyr Tyr Cys
                85                  90                  95

Ala Ala Ser Val Leu Ser Val Phe Arg Pro Leu Ser Ser Asn Gln Tyr
                100                 105                 110

His Tyr Trp Gly Gln Gly Thr Gln Val Thr Val Ser Ser
            115                 120                 125
```

<210> SEQ ID NO 82
<211> LENGTH: 126
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Tyr Ser Asn Tyr
            20                  25                  30

Cys Met Ala Trp Phe Arg Gln Ala Pro Gly Lys Glu Arg Glu Gly Val
            35                  40                  45

Ala Ala Ile Asp Ser Asp Gly Ser Thr Ser Tyr Ala Asp Ser Val Lys
        50                  55                  60

Gly Arg Phe Thr Ile Ser Gln Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Gly Asn Lys Lys Pro Tyr Gln Leu Cys Asn Thr Asp Ser Arg Arg
                100                 105                 110

Tyr Tyr His Trp Gly Gln Gly Thr Gln Val Thr Val Ser Ser
            115                 120                 125
```

<210> SEQ ID NO 83
<211> LENGTH: 124
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

```
Gln Val Gln Leu Gln Glu Ser Gly Gly Gly Ser Val Gln Ala Gly Gly
1               5                   10                  15

Ser Leu Arg Leu Ser Cys Ala Ser Ser Gly Tyr Ser Arg Thr Ser Arg
            20                  25                  30

Trp Met Ala Trp Phe Arg Gln Ala Pro Gly Lys Glu Arg Glu Gly Val
            35                  40                  45
```

Ala Ala Ile Tyr Thr Gly Gly Ser Ser Thr Leu Tyr Ala Asn Ser Met
            50                  55                  60

Ala Asp Arg Val Thr Ile Ser Gln Asp Asn Ala Lys Asn Thr Val Tyr
65                  70                  75                  80

Leu Arg Met Asn Asn Leu Lys Pro Glu Asp Thr Ala Met Tyr Tyr Cys
                85                  90                  95

Ala Ala Asp Lys Leu Ala Gly Asp Phe Trp Leu Val Asp Arg Trp Arg
                100                 105                 110

Ala Trp Gly Gln Gly Thr Gln Val Thr Val Ser Ser
            115                 120

<210> SEQ ID NO 84
<211> LENGTH: 129
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Val Gln Leu Gln Glu Ser Gly Gly Gly Ser Val Gln Ala Gly Gly
1               5                   10                  15

Ser Leu Arg Leu Ser Cys Arg Thr Ser Gly Tyr Thr Asn Asn Leu Lys
            20                  25                  30

Ser Met Ala Trp Phe Arg Gln Ala Pro Gly Lys Glu Arg Glu Ala Val
        35                  40                  45

Ala Ser Ile His Asn Asn Gly Gly Pro Thr Tyr Asp Tyr Tyr Ala Glu
    50                  55                  60

Ser Val Lys Gly Arg Phe Ala Ile Ser Gln Asp Asn Ala Lys Asn Thr
65                  70                  75                  80

Leu Tyr Leu Gln Met Ser Ser Ala Lys Pro Glu Asp Thr Ala Val Tyr
                85                  90                  95

Tyr Cys Ala Ala Asp Asn Arg Phe Leu Gly Ser Gly Ser Trp Arg Leu
                100                 105                 110

Pro Ser Leu Tyr Asn Tyr Trp Gly Gln Gly Thr Gln Val Thr Val Ser
            115                 120                 125

Ser

<210> SEQ ID NO 85
<211> LENGTH: 128
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Phe Thr Thr Ala
            20                  25                  30

Tyr Met Gly Trp Phe Arg Gln Ala Pro Gly Lys Glu Arg Glu Gly Val
        35                  40                  45

Ala Ala Ile Asp Ser Asp Gly Arg Thr Glu Tyr Ala Asp Ala Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala 85                  90                  95
Ala Asp Lys Asp Asp Trp Leu Leu Leu His Gly Arg Ser Leu Phe Pro
            100                 105                 110

Ser Ala Phe Ala Tyr Trp Gly Gln Gly Thr Gln Val Thr Val Ser Ser
            115                 120                 125

<210> SEQ ID NO 86
<211> LENGTH: 393
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 86
caggtgcagc tgcaggagtc tggaggaggc ttggtgcagc cggggggtc tctgagactc      60 tcctgtacag cctctggatt gacttttgat gattatgcca tgggctggtt ccgccaggct    120
ccagggaagg ggcgcgaggg tgtctcactt attacctgga gtggtagtag cacatactat    180
gcggactccg tgaagggccg attcaccgtc tccagagaca ccgccacgaa tacgctggtt    240
ctacaaatga acagcctgaa accagaggat acggccatgt attactgtgc ggcagatcca    300
cgtagtggtg gttactactc cagccccccct ccccccgctg tgtacaggta tctccgattt    360
tggggccagg gcacccaggt caccgtctcc tca                                  393

<210> SEQ ID NO 87
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 87
caggtgcagc tgcaggagtc tggaggaggc tcggtgcagg ctggagggtc tctgagactc      60
tcctgtgcag cctctagaga cacctacacg cgctacttta tgggctggtt ccgccagact    120
ccagggaagg agggcgaggg ggtcgcagtc cttctacctg gcgttgatta tacattctat    180
gccgactccg tgaagggccg gttcaccatc acccaagaca cgccaagaa cacggtgtat    240 ctgcaaatga acagcctgaa acctgaggac actgccatgt actactgtgc ggcagatgta    300
acggtcggta gtaggtggtc tcaagcttcg aattataact actggggcca ggggacccag    360
gtcaccgtct cctca                                                     375

<210> SEQ ID NO 88
<211> LENGTH: 378
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 88
caggtgcagc tgcaggagtc tggaggaggc tcggtgcagg ctggagggtc tctgagactc      60
tcctgtgcag cctctggata cacctacagt ggctactgta tgggctggtt ccgccaggct    120
ccagggaagg agcacgaggg ggtcgcaagt attgtttctg gtcttggtag accatactat    180
gccgattccg tgaagggccg attcaccatc tcccaagaca cgccaagaa cacggtgtat    240 ctgcaaatga acagcctgaa acctgaggac actgccatgt actactgtgc ggcagaatgg    300

```
gcgacgaaac tctgttctga gatacctgcc accgagtggg actactgggg ccaggggacc    360
caggtcaccg tctcctca                                                   378

<210> SEQ ID NO 89
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 89
caggtgcagc tgcaggagtc tgggggaggc tcggtgcagg ctggagggtc tctgagactc    60
tcctgtacag cctctggatt cactgttgac gattctggca tgggctggta ccgccaggct   120
ccagggaatg agtgcgagtt ggtctcaact attagtagtg atggtagcac atactatgca   180
gactccgtga agggccgatt caccatctcc aagacaacg ccaagaacac ggtgtatctg    240
caaatgaaca gcctgaaacc tgaggacacg gccgtgtatt actgtgcggc accccgggtc   300
ggtgtgggtt gggtacgtcc ctgtgattat gagtataact actggggcca ggggacccag   360
gtcaccgtct cctca                                                     375

<210> SEQ ID NO 90
<211> LENGTH: 348
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 90
caggtgcagc tgcaggagtc tgggggaggc ttggtgcagc ctgggggtc tctgagactc     60 tcctgtgcag cctctggatt caccttcagt aacaaagtca tgagctgggt ccgccaggct   120
ccagggaagg gattcgagtg gtctcaagt attgcgagag gtggtgactg gacaacctat    180
gcagactccg tgagggccg attcaccatc tccagagaca acgccaagaa cactctgtat    240
ctgcaattga acagcctgaa aactgaggac acggccatgt attactgtgc ccaagctgag   300
aattggaaaa ccccgccggg ccaggggacc caggtcaccg tctcctca                348

<210> SEQ ID NO 91
<211> LENGTH: 378
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 91
caggtgcagc tgcaggagtc tgggggaggc tcggtgcagg ctggagggtc tctgagactc    60
tcctgtgcag cctctggata cgcctacact cgcaactgca tgggctggtt ccgccaggct   120
ccagggaagg agcgcgagga agtcgcaact attaatcttg gtggtggtag cacatactat   180
gccgactccg tgaagggccg attcgccatc tcccaagaca acgccaagaa cacggtgtat   240
ctgcaaatga caacctgaa acctgaggac actgccatgt actactgtgc ggcgatcgct    300
cagtacggtg gtagcttgtg cagcaatttc ggatggtata acttgtgggg ccaggggacc   360
caggtcaccg tctcctca                                                  378

<210> SEQ ID NO 92
```

```
<211> LENGTH: 348
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 92
caggtgcagc tgcaggagtc tggaggaggc ttggtgcagg caggggggtc tctgaagctc      60
tcctgtacag tctctggatt cgcattcggt tcctcccaca tgagctgggt ccgccgggct     120
ccagggaagg ggctcgagtg ggtctcaact attcatagcg gtggtggctt tggcgactat     180
gcgaactccg tgcagggccg attcaccatc tccagagacg tcgccaagaa cacgctgtat     240
ctgcaaatga acagcctgaa acctgaagac acggccatat attactgtgc gctcgcgacg     300
gattggagaa agccccccgg ccaggggacc caggtcaccg tctcctca                  348

<210> SEQ ID NO 93
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 93
caggtgcagc tgcaggagtc tgggggaggg tcggtgcagg ctggagggtc tctgagactc      60
tcctgtgcag cctctggata cacctccagt aggaaataca taggatggtt ccgacaggct     120
ccagggaagc agcgcgagtg ggtcgcaggt attgatactg gtgctggtgg cacatgcacg     180
atcgcctcag tgcagggccg gttcaccatc tcccaagacg tcgccaagaa cacgttgtat     240
ctccaaatag acagcctgaa acctgaagac actgccgtat actactgtgc ggcagattgg     300
gtccggggtg gtttttgctc aggcgatgct gactttcgtt attggggcca ggggacccag     360
gtcaccgtct cctca                                                      375

<210> SEQ ID NO 94
<211> LENGTH: 366
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 94
caggtgcagc tgcaggagtc tgggggaggc ttggtgcagc ctgggggggtc tctgagactc     60 tcctgtggag cctctggatt caccttcagt agcaccgcca tgtggtggtt ccgccaggct     120
ccagggaagg ggctggagtg ggtgtccagt attaccagtg atgttagtgg cacgtactat     180
gcagactccg tccagggccg attcaccatc tccagagaca acgcaagaa cacggtgtat      240 ctgcaaatga acagcctgag atctgaggac acggccctgt attattgtgc cacctcgtgt     300
gggtttagtg gtggtacgtg gtcttgtaaa tacaggggcc aggggaccca ggtcaccgtc     360
tcctca                                                                366

<210> SEQ ID NO 95
<211> LENGTH: 348
<212> TYPE: DNA
<213> ORGANISM: Artificial Sequence
<220> FEATURE:
<223> OTHER INFORMATION: Description of Artificial Sequence: Synthetic
      nucleic acid
```

<400> SEQUENCE: 95

```
caggtgcagc tgcaggagtc tgggggaggc ttggtgcagc ctggggggtc tctgagactc    60
tcctgtgcag cctctggatt cgcattcggt tcctcccaca tgagctgggt ccgccgggct   120
ccagggaagg ggctcgagtg ggtctcaact attcatagcg gtggtggctt tggcgactat   180
gcgaactccg tgcagggccg attcaccatc tccagagacg tcgccaagaa cacgctgtat   240
ctgcaaatga acagcctgaa acctgaagac acggccatat attactgtgc gctcgcgacg   300
gattggagaa agccccccgg ccaggggacc caggtcaccg tctcctca               348
```

<210> SEQ ID NO 96
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 96

```
caggtgcagc tgcaggagtc tggaggaggc tcggtgcaga ctggagggtc tctgagactc    60
tcctgtacag cctctggatt cacttttgat gcggctgaca tgggctggta ccgccaggct   120
ccagggaatg agtgcgagtt ggtctcaatt attagtagtg atggtagtac atactatgcc   180
gactccgtga agggccgatt caccatctcc aagacaacgc caagaacac ggtgtatctg   240
caaatgaaca gcctgaaacc tgaggacacg gccgtgtatt actgtgcggc accccgggtc   300
ggtgtgggtt gggtacgtcc ctgtgactat gagtataact actggggcca ggggacccag   360
gtcaccgtct cctca                                                   375
```

<210> SEQ ID NO 97
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 97

```
caggtgcagc tgcaggagtc tgggggaggc tcggtgcagg ctggagggtc tctgagactc    60
tcctgtgcag cctctagaga cacctacacg cgctacttta tgggctggtt ccgccagact   120
ccagggaagg agcccgaggg ggtcgcagtc cttctacctg gcggtgctta cacattctat   180
gccgactccg tgaagggccg gttcaccatc acccaagaca cgccaagaa cacggtgtat   240
ctgcaaatga acagcctgaa acctgaggac actgccatgt actactgtgc ggcagatgtc   300
acggtcggta gtaggtggtc tcaagcttcg aactataact actggggcca ggggacccag   360
gtcaccgtct cctca                                                   375
```

<210> SEQ ID NO 98
<211> LENGTH: 363
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 98

```
caggtgcagc tgcaggagtc tgggggaggc tcggtgcagg ctggagggtc tctgagactc    60
tcctgtacag cctctagcaa caccggcagg atgggctggt tccgccaggc tccagggaaa   120
```

```
gagcgcgagg gggtcacagc ggttgataat tttggtagga caaactacgc gaagtacgtg    180
aagggccgat tcaccatctc caaagacaac gccaagaaca ctctgtatct gcaaatgaac    240
agcctgaaac ctgaggacac tgccatgtac tactgtgcgg cggatccctg gggacgtggt    300
gcggccctca ccccaaatga gtatatctac tggggccagg ggacccaggt caccgtctcc    360
tca                                                                  363
```

<210> SEQ ID NO 99
<211> LENGTH: 372
<212> TYPE: DNA
<213> ORGANISM: Artificial Sequence
<220> FEATURE:
<223> OTHER INFORMATION: Description of Artificial Sequence: Synthetic
    nucleic acid

<400> SEQUENCE: 99

```
caggtgcagc tgcaggagtt tggaggaggc tcggtgcagg ctggagggtc tttgagactc     60
tcctgtgtag cctctggatt caccttcagt aactactgca tgggctggtt ccgccaggat    120
ccagggaagg agcgcgaggc ggtcgcacgt atttttgttg atggcagcac aaggtacgca    180
gacgccgtga agggccgatt caccatctcc aaggacaacg ccaagaacac tctgtatgtg    240
caaatcaaca gcctgaaacc tgaggacact gccatgtact actgtacgac accgtttccc    300
tggacattgt gtgttgatgg ccccggcgcg tataaatact ggggccaggg gacccaggtc    360
accgtctcct ca                                                        372
```

<210> SEQ ID NO 100
<211> LENGTH: 387
<212> TYPE: DNA
<213> ORGANISM: Artificial Sequence
<220> FEATURE:
<223> OTHER INFORMATION: Description of Artificial Sequence: Synthetic
    nucleic acid

<400> SEQUENCE: 100

```
caggtgcagc tgcaggagtc tggggggaggc tcagtgcagg ctggagggtc tctgagactc     60
tcctgtgtag tttttggaaa cattttcagg aactactgca tggcctggtt ccgccaggct    120
ccaggaaaag agcgcgaggg ggtggtagtt atttatactg gtggtggtag cacatactat    180
gccgactccg tgaagggccg attccaccatc tcccaagaca cgccaagaa cacggtgtat    240 ttgcaaatga cagcctgaa acatgaggac actgccatgt actactgtgc ggcagaccaa    300
accaccagat actcgagcga ctatgtaaat gtcggcccgt gcgacatgga cagctggggc    360
aaaggaaccc aggtcaccgt ctcctca                                        387
```

<210> SEQ ID NO 101
<211> LENGTH: 384
<212> TYPE: DNA
<213> ORGANISM: Artificial Sequence
<220> FEATURE:
<223> OTHER INFORMATION: Description of Artificial Sequence: Synthetic
    nucleic acid

<400> SEQUENCE: 101

```
caggtgcagc tgcaggagtc tggaggaggc tcggtgcagg ctggagggtc tctgagactc     60
tcctgtgcag cctctggata cacctacaat aaatactcct ggggctggtt ccgccaggct    120
ccagggaagg agcgcgaggg ggtcgcagga attgacagtg atggtagcac aagctacgca    180
gactccgtga agggccgatt caccatctcc aaagacaaca ccaagaacac tctgtatctg    240
```

```
caaatgaaca gcctgaaacc tgaggacact gccatgtact actgtgcggc atctgattgg      300
gtgtctgcta ttcaggctct tggtgttctg gcggtgaggc cgtatgagta ctggggccag      360
gggacccagg tcaccgtctc ctca                                             384
```

<210> SEQ ID NO 102
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 102

```
caggtgcagc tgcaggagtc tggaggaggt tcggcgcagg ctggagggtc tctgagactc       60
tcctgtgcag cctctagata cacctccagt agcaacgcga tgggatggtt ccgacaggct      120
ccagggaagc agcgcgagtg ggtcgcaggt agtgatactg gtgctggtat cacatgcaat      180
gccgcctcag tgaagggccg gttcaccatc tcccaagacg tcgccaagaa cacggtgtat      240
ctccaaatga acagcctgaa acctgaggac actgccgtat actactgtgc ggcagattgg      300
ttccggggtg cttttttgctc aggcgatgct gactttcgtt attggggcca ggggacccag      360
gtcaccgtct cctca                                                       375
```

<210> SEQ ID NO 103
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 103

```
caggtgcagc tgcaggagtc tgggggaggc tcggtgcaga ctggagggtc tctgagactc       60
tcttgtgcag cttctggatt gaccagtact actaagtaca tgggctggtt ccgccaggct      120
ccagggaagg agcgcgaggg ggtcgcaggt atctatatta gtagtggtgc acatactat      180 gacgactctg tgaagggccg attcaccatc tcccaagaca cgccaagaa cacggtatat      240 ttgcacatca acagcctgga acctgatgac accgcgatgt actactgtgc ggcttcagta      300
ttaagtgttt tccggcccct atctagcaac caatatcact actggggtca ggggacccag      360
gtcaccgtct cctca                                                       375
```

<210> SEQ ID NO 104
<211> LENGTH: 378
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 104

```
caggtgcagc tgcaggagtc tgggggaggc tcggtgcagg ctggagggtc tctgagactc       60
tcctgtgcag cctctggatt tacctacagt aactactgca tggcctggtt ccgccaggct      120
ccagggaagg agcgcgaggg ggtcgcagct attgatagtg atggtagcac aagctacgca      180
gactccgtga agggccgatt caccatctcc aagacaacg ccaagaacac tctgtatctg      240
caaatgaaca gcctgaaacc tgaggacaca gccatgtact actgtgcggc agggaacaaa      300
aagccgtacc aactgtgtaa tactgactcc cgccgatatt accactgggg ccaggggacc      360
```

-continued caggtcaccg tctcctca                                              378

<210> SEQ ID NO 105
<211> LENGTH: 372
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 105
caggtgcagc tgcaggagtc tggaggaggc tcggtgcagg ctggagggtc tctgagactc      60
tcctgtgcgt cctctggata cagccgaact agtcgctgga tggcctggtt ccgccaggct     120
ccagggaagg agcgcgaggg ggtcgcagct atttatactg gtggtagtag tacattgtat     180
gccaactcca tggcggaccg agtcaccatc tcccaagaca cgccaagaa cacggtgtat      240 ctgcgaatga caacctgaa acccgaggac actgccatgt actactgtgc ggcagataaa      300
ttggccggtg atttttggtt ggtagatcgg tggcgtgcct ggggccaggg gacccaggtc     360
accgtctcct ca                                                         372

<210> SEQ ID NO 106
<211> LENGTH: 387
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 106
caggtgcagc tgcaggagtc tgggggaggc tcggtgcagg ctggagggtc tctgagactc      60
tcctgtagaa cctctggata caccaacaat ctgaagtcca tggcctggtt ccgccaggct     120
ccagggaagg agcgcgaggc cgtcgcaagt atccataata acggaggacc acatacgat      180 tactatgccg aatccgtgaa gggccgattc gccatctccc aagacaacgc caagaacacg     240
ctgtatctgc aaatgagcag cgcgaaacct gaggacactg ccgtgtatta ctgtgcggca     300
gataaccggt ttctggggtc gggttcgtgg cggttaccca gcctctataa ttactggggc     360 cagggggacccc aggtcaccgt ctcctca                                        387

<210> SEQ ID NO 107
<211> LENGTH: 384
<212> TYPE: DNA
<213> ORGANISM: Artificial Sequence
<220> FEATURE:
<223> OTHER INFORMATION: Description of Artificial Sequence: Synthetic
      nucleic acid

<400> SEQUENCE: 107
caggtgcagc tgcaggagtc tgggggaggc tcggtgcagg ctggagggtc tctgagactc      60
tcctgtgcag cctctggata caccttcaca actgcctaca tgggctggtt ccgccaggct     120
ccagggaagg agcgcgaggg ggtcgcagca attgacagtg acgtcgaac ggaatacgca      180 gacgccgtga agggccgatt caccatctct aaagacaacg ccaagaatac tctgtatctg     240
caaatgaaca gcctgaaacc tgaggacact gccatgtact actgtgcggc agacaaggat     300
gactggttac tgctacacgg cagatctttta ttcccttcgg cctttgctta ctggggccag    360 ggacccagg tcaccgtctc ctca                                              384

<210> SEQ ID NO 108
<211> LENGTH: 352
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

```
Gln Val Gln Leu Gln Glu Ser Gly Gly Gly Ser Val Gln Ala Gly Gly
1               5                   10                  15

Ser Leu Arg Leu Ser Cys Ala Ala Ser Arg Asp Thr Tyr Thr Arg Tyr
            20                  25                  30

Phe Met Gly Trp Phe Arg Gln Thr Pro Gly Lys Glu Gly Glu Gly Val
        35                  40                  45

Ala Val Leu Leu Pro Gly Gly Asp Tyr Thr Phe Tyr Ala Asp Ser Val
    50                  55                  60

Lys Gly Arg Phe Thr Ile Thr Gln Asp Ser Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Asp Val Thr Val Gly Ser Arg Trp Ser Gln Ala Ser Asn Tyr
            100                 105                 110

Asn Tyr Trp Gly Gln Gly Thr Gln Val Thr Val Ser Ser Asp Lys Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350
```

<210> SEQ ID NO 109
<211> LENGTH: 353

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Gly Tyr
            20                  25                  30

Cys Met Gly Trp Phe Arg Gln Ala Pro Gly Lys Glu His Glu Gly Val
        35                  40                  45

Ala Ser Ile Val Ser Gly Leu Gly Arg Pro Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Glu Trp Ala Thr Lys Leu Cys Ser Glu Ile Pro Ala Thr Glu
            100                 105                 110

Trp Asp Tyr Trp Gly Gln Gly Thr Gln Val Thr Val Ser Ser Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 110
<211> LENGTH: 352
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Val Asp Asp Ser
            20                  25                  30

Gly Met Gly Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Val Tyr Tyr Cys Ala
            85                  90                  95

Ala Pro Arg Val Gly Val Gly Trp Val Arg Pro Cys Asp Tyr Glu Tyr
        100                 105                 110

Asn Tyr Trp Gly Gln Gly Thr Gln Val Thr Val Ser Ser Asp Lys Thr
    115                 120                 125

His Thr Cys Pro Pro Cys Pro Ala Pro Glu Leu Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Asp Val Ser His Glu Asp Pro
            165                 170                 175

Glu Val Lys Phe Asn Trp Tyr Val Asp Gly Val Glu Val His Asn Ala
        180                 185                 190

Lys Thr Lys Pro Arg Glu Glu Gln Tyr Asn Ser Thr Tyr Arg Val Val
    195                 200                 205

Ser Val Leu Thr Val Leu His Gln Asp Trp Leu Asn Gly Lys Glu Tyr
210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
            245                 250                 255

Pro Pro Ser Arg Asp Glu Leu Thr Lys Asn Gln Val Ser Leu Thr Cys
        260                 265                 270

Leu Val Lys Gly Phe Tyr Pro Ser Asp Ile Ala Val Glu Trp Glu Ser
    275                 280                 285

Asn Gly Gln Pro Glu Asn Asn Tyr Lys Thr Thr Pro Pro Val Leu Asp
290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
            325                 330                 335

Leu His Asn His Tyr Thr Gln Lys Ser Leu Ser Leu Ser Pro Gly Lys
        340                 345                 350

<210> SEQ ID NO 111
<211> LENGTH: 343
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Val Gln Leu Gln Glu Ser Gly Gly Gly Leu Val Gln Ala Gly Gly
1               5                   10                  15

Ser Leu Lys Leu Ser Cys Thr Val Ser Gly Phe Ala Phe Gly Ser Ser
            20                  25                  30

His Met Ser Trp Val Arg Arg Ala Pro Gly Lys Gly Leu Glu Trp Val
        35                  40                  45

Ser Thr Ile His Ser Gly Gly Gly Phe Gly Asp Tyr Ala Asn Ser Val
    50                  55                  60

Gln Gly Arg Phe Thr Ile Ser Arg Asp Val Ala Lys Asn Thr Leu Tyr
65                  70                  75                  80

Leu Gln Met Asn Ser Leu Lys Pro Glu Asp Thr Ala Ile Tyr Tyr Cys
                85                  90                  95

Ala Leu Ala Thr Asp Trp Arg Lys Pro Gly Gln Gly Thr Gln Val
            100                 105                 110

Thr Val Ser Ser Asp Lys Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 112
<211> LENGTH: 349
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Gln Val Gln Leu Gln Glu Ser Gly Gly Gly Leu Val Gln Pro Gly Gly
1               5                   10                  15

Ser Leu Arg Leu Ser Cys Gly Ala Ser Gly Phe Thr Phe Ser Ser Thr
            20                  25                  30

Ala Met Trp Trp Phe Arg Gln Ala Pro Gly Lys Gly Leu Glu Trp Val
        35                  40                  45

Ser Ser Ile Thr Ser Asp Val Ser Gly Thr Tyr Tyr Ala Asp Ser Val
    50                  55                  60

Gln Gly Arg Phe Thr Ile Ser Arg Asp Asn Gly Lys Asn Thr Val Tyr
65                  70                  75                  80

Leu Gln Met Asn Ser Leu Arg Ser Glu Asp Thr Ala Leu Tyr Tyr Cys
                85                  90                  95

Ala Thr Ser Cys Gly Phe Ser Gly Gly Thr Trp Ser Cys Lys Tyr Arg
            100                 105                 110

Gly Gln Gly Thr Gln Val Thr Val Ser Ser Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345

<210> SEQ ID NO 113
<211> LENGTH: 343
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Gly Ser Ser
            20                  25                  30

His Met Ser Trp Val Arg Arg Ala Pro Gly Lys Gly Leu Glu Trp Val
        35                  40                  45

Ser Thr Ile His Ser Gly Gly Gly Phe Gly Asp Tyr Ala Asn Ser Val
    50                  55                  60

Gln Gly Arg Phe Thr Ile Ser Arg Asp Val Ala Lys Asn Thr Leu Tyr
65                  70                  75                  80

Leu Gln Met Asn Ser Leu Lys Pro Glu Asp Thr Ala Ile Tyr Tyr Cys
                85                  90                  95

Ala Leu Ala Thr Asp Trp Arg Lys Pro Gly Gln Gly Thr Gln Val
            100                 105                 110

Thr Val Ser Ser Asp Lys Thr His Thr Cys Pro Pro Cys Pro Ala Pro
            115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
            165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
            245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
            325                 330                 335

Leu Ser Leu Ser Pro Gly Lys
            340
```

<210> SEQ ID NO 114
<211> LENGTH: 355
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

```
Gln Val Gln Leu Gln Glu Ser Gly Gly Gly Ser Val Gln Ala Gly Gly
1               5                   10                  15
Ser Leu Arg Leu Ser Cys Ala Ala Ser Gly Tyr Thr Tyr Asn Lys Tyr
            20                  25                  30
Ser Trp Gly Trp Phe Arg Gln Ala Pro Gly Lys Glu Arg Glu Gly Val
        35                  40                  45
Ala Gly Ile Asp Ser Asp Gly Ser Thr Ser Tyr Ala Asp Ser Val Lys
 50                  55                  60
Gly Arg Phe Thr Ile Ser Lys Asp Asn Thr Lys Asn Thr Leu Tyr Leu
 65                  70                  75                  80
Gln Met Asn Ser Leu Lys Pro Glu Asp Thr Ala Met Tyr Tyr Cys Ala
                85                  90                  95
Ala Ser Asp Trp Val Ser Ala Ile Gln Ala Leu Gly Val Leu Ala Val
            100                 105                 110
Arg Pro Tyr Glu Tyr Trp Gly Gln Gly Thr Gln Val Thr Val Ser Ser
            115                 120                 125
Asp Lys Thr His Thr Cys Pro Pro Cys Pro Ala Pro Glu Leu Leu Gly
        130                 135                 140
Gly Pro Ser Val Phe Leu Phe Pro Pro Lys Pro Lys Asp Thr Leu Met
145                 150                 155                 160
Ile Ser Arg Thr Pro Glu Val Thr Cys Val Val Val Asp Val Ser His
            165                 170                 175
Glu Asp Pro Glu Val Lys Phe Asn Trp Tyr Val Asp Gly Val Glu Val
            180                 185                 190
His Asn Ala Lys Thr Lys Pro Arg Glu Glu Gln Tyr Asn Ser Thr Tyr
        195                 200                 205
Arg Val Val Ser Val Leu Thr Val Leu His Gln Asp Trp Leu Asn Gly
    210                 215                 220
Lys Glu Tyr Lys Cys Lys Val Ser Asn Lys Ala Leu Pro Ala Pro Ile
225                 230                 235                 240
Glu Lys Thr Ile Ser Lys Ala Lys Gly Gln Pro Arg Glu Pro Gln Val
            245                 250                 255
Tyr Thr Leu Pro Pro Ser Arg Asp Glu Leu Thr Lys Asn Gln Val Ser
            260                 265                 270
Leu Thr Cys Leu Val Lys Gly Phe Tyr Pro Ser Asp Ile Ala Val Glu
        275                 280                 285
Trp Glu Ser Asn Gly Gln Pro Glu Asn Asn Tyr Lys Thr Thr Pro Pro
    290                 295                 300
Val Leu Asp Ser Asp Gly Ser Phe Phe Leu Tyr Ser Lys Leu Thr Val
305                 310                 315                 320
Asp Lys Ser Arg Trp Gln Gln Gly Asn Val Phe Ser Cys Ser Val Met
            325                 330                 335
His Glu Ala Leu His Asn His Tyr Thr Gln Lys Ser Leu Ser Leu Ser
            340                 345                 350
Pro Gly Lys
        355

<210> SEQ ID NO 115
<211> LENGTH: 351
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115
```

Gln Val Gln Leu Gln Glu Ser Gly Gly Gly Ser Val Gln Ala Gly Gly
1               5                   10                  15

Ser Leu Arg Leu Ser Cys Ala Ser Gly Tyr Ser Arg Thr Ser Arg
            20                  25                  30

Trp Met Ala Trp Phe Arg Gln Ala Pro Gly Lys Glu Arg Glu Gly Val
                35                  40                  45

Ala Ala Ile Tyr Thr Gly Gly Ser Ser Thr Leu Tyr Ala Asn Ser Met
        50                  55                  60

Ala Asp Arg Val Thr Ile Ser Gln Asp Asn Ala Lys Asn Thr Val Tyr
65                  70                  75                  80

Leu Arg Met Asn Asn Leu Lys Pro Glu Asp Thr Ala Met Tyr Tyr Cys
                85                  90                  95

Ala Ala Asp Lys Leu Ala Gly Asp Phe Trp Leu Val Asp Arg Trp Arg
            100                 105                 110

Ala Trp Gly Gln Gly Thr Gln Val Thr Val Ser Ser Asp Lys Thr His
                115                 120                 125

Thr Cys Pro Pro Cys Pro Ala Pro Glu Leu Leu Gly Gly Pro Ser Val
        130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
            210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys
                340                 345                 350

<210> SEQ ID NO 116
<211> LENGTH: 343
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Val Gln Leu Gln Glu Ser Gly Gly Gly Leu Val Gln Pro Gly Gly

```
            1               5              10              15
          Ser Leu Arg Leu Ser Cys Ala Ala Ser Gly Phe Ala Phe Gly Ser Ser
                         20              25              30

His Met Ser Trp Phe Arg Arg Ala Pro Gly Lys Gly Leu Glu Trp Val
                         35              40              45

Ser Thr Ile His Ser Gly Gly Phe Gly Asp Tyr Ala Asp Ser Val
                         50              55              60

Lys Gly Arg Phe Thr Ile Ser Arg Asp Asn Ser Lys Asn Thr Leu Tyr
           65              70              75              80

Leu Gln Met Asn Ser Leu Arg Pro Glu Asp Thr Ala Val Tyr Tyr Cys
                         85              90              95

Ala Leu Ala Thr Asp Trp Arg Lys Pro Trp Gly Gln Gly Thr Leu Val
                        100             105             110

Thr Val Ser Ser Asp Lys Thr His Thr Cys Pro Pro Cys Pro Ala Pro
                        115             120             125

Glu Leu Leu Gly Gly Pro Ser Val Phe Leu Phe Pro Pro Lys Pro Lys
                        130             135             140

Asp Thr Leu Met Ile Ser Arg Thr Pro Glu Val Thr Cys Val Val Val
          145             150             155             160

Asp Val Ser His Glu Asp Pro Glu Val Lys Phe Asn Trp Tyr Val Asp
                        165             170             175

Gly Val Glu Val His Asn Ala Lys Thr Lys Pro Arg Glu Glu Gln Tyr
                        180             185             190

Asn Ser Thr Tyr Arg Val Val Ser Val Leu Thr Val Leu His Gln Asp
                        195             200             205

Trp Leu Asn Gly Lys Glu Tyr Lys Cys Lys Val Ser Asn Lys Ala Leu
                        210             215             220

Pro Ala Pro Ile Glu Lys Thr Ile Ser Lys Ala Lys Gly Gln Pro Arg
          225             230             235             240

Glu Pro Gln Val Tyr Thr Leu Pro Pro Ser Arg Asp Glu Leu Thr Lys
                        245             250             255

Asn Gln Val Ser Leu Thr Cys Leu Val Lys Gly Phe Tyr Pro Ser Asp
                        260             265             270

Ile Ala Val Glu Trp Glu Ser Asn Gly Gln Pro Glu Asn Asn Tyr Lys
                        275             280             285

Thr Thr Pro Pro Val Leu Asp Ser Asp Gly Ser Phe Phe Leu Tyr Ser
                        290             295             300

Lys Leu Thr Val Asp Lys Ser Arg Trp Gln Gln Gly Asn Val Phe Ser
          305             310             315             320

Cys Ser Val Met His Glu Ala Leu His Asn His Tyr Thr Gln Lys Ser
                        325             330             335

Leu Ser Leu Ser Pro Gly Lys
                        340

<210> SEQ ID NO 117
<211> LENGTH: 351
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Val Gln Leu Gln Glu Ser Gly Gly Gly Leu Val Gln Pro Gly Gly
          1               5              10              15
```

```
Ser Leu Arg Leu Ser Cys Ala Ala Ser Gly Tyr Ser Arg Thr Ser Arg
            20                  25                  30

Trp Met Ala Trp Phe Arg Gln Ala Pro Gly Lys Gly Leu Glu Gly Val
        35                  40                  45

Ala Ala Ile Tyr Thr Gly Gly Ser Ser Thr Leu Tyr Ala Asp Ser Val
50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
            85                  90                  95

Ala Ala Asp Lys Leu Ala Gly Asp Phe Trp Leu Val Asp Arg Trp Arg
            100                 105                 110

Ala Trp Gly Gln Gly Thr Leu Val Thr Val Ser Ser Asp Lys Thr His
        115                 120                 125

Thr Cys Pro Pro Cys Pro Ala Pro Glu Leu Leu Gly Gly Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
            165                 170                 175

Val Lys Phe Asn Trp Tyr Val Asp Gly Val Glu Val His Asn Ala Lys
        180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
            245                 250                 255

Pro Ser Arg Asp Glu Leu Thr Lys Asn Gln Val Ser Leu Thr Cys Leu
        260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
            325                 330                 335

His Asn His Tyr Thr Gln Lys Ser Leu Ser Leu Ser Pro Gly Lys
            340                 345                 350

<210> SEQ ID NO 118
<211> LENGTH: 480
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Ser Arg Thr Ser Arg
            20                  25                  30
```

```
Trp Met Ala Trp Phe Arg Gln Ala Pro Gly Lys Gly Leu Glu Gly Val
        35                  40                  45

Ala Ala Ile Tyr Thr Gly Gly Ser Ser Thr Leu Tyr Ala Asp Ser Val
 50                  55                  60

Lys Gly Arg Phe Thr Ile Ser Arg Asp Asn Ala Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Ala Asp Lys Leu Ala Gly Asp Phe Trp Leu Val Asp Arg Trp Arg
                100                 105                 110

Ala Trp Gly Gln Gly Thr Leu Val Thr Val Ser Ser Asp Lys Thr His
                115                 120                 125

Thr Cys Pro Pro Cys Pro Ala Pro Glu Leu Leu Gly Gly Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
                180                 185                 190

Thr Lys Pro Arg Glu Glu Gln Tyr Asn Ser Thr Tyr Arg Val Val Ser
                195                 200                 205

Val Leu Thr Val Leu His Gln Asp Trp Leu Asn Gly Lys Glu Tyr Lys
                210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Arg Asp Glu Leu Thr Lys Asn Gln Val Ser Leu Thr Cys Leu
                260                 265                 270

Val Lys Gly Phe Tyr Pro Ser Asp Ile Ala Val Glu Trp Glu Ser Asn
                275                 280                 285

Gly Gln Pro Glu Asn Asn Tyr Lys Thr Thr Pro Pro Val Leu Asp Ser
                290                 295                 300

Asp Gly Ser Phe Phe Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu Ser Pro Gly Lys Gly
                340                 345                 350

Gly Gly Gly Ser Gln Val Gln Leu Gln Glu Ser Gly Gly Gly Leu Val
                355                 360                 365

Gln Pro Gly Gly Ser Leu Arg Leu Ser Cys Ala Ala Ser Gly Tyr Ser
370                 375                 380

Arg Thr Ser Arg Trp Met Ala Trp Phe Arg Gln Ala Pro Gly Lys Gly
385                 390                 395                 400

Leu Glu Gly Val Ala Ala Ile Tyr Thr Gly Gly Ser Ser Thr Leu Tyr
                405                 410                 415

Ala Asp Ser Val Lys Gly Arg Phe Thr Ile Ser Arg Asp Asn Ala Lys
                420                 425                 430

Asn Ser Val Tyr Leu Gln Met Asn Ser Leu Arg Ala Glu Asp Thr Ala
                435                 440                 445
```

```
Val Tyr Tyr Cys Ala Ala Asp Lys Leu Ala Gly Asp Phe Trp Leu Val
    450                 455                 460

Asp Arg Trp Arg Ala Trp Gly Gln Gly Thr Leu Val Thr Val Ser Ser
465                 470                 475                 480

<210> SEQ ID NO 119
<211> LENGTH: 480
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Ser Arg Thr Ser Arg
            20                  25                  30

Trp Met Ala Trp Phe Arg Gln Ala Pro Gly Lys Gly Leu Glu Gly Val
        35                  40                  45

Ala Ala Ile Tyr Thr Gly Gly Ser Thr Leu Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Ala Asp Lys Leu Ala Gly Asp Phe Trp Leu Val Asp Arg Trp Arg
            100                 105                 110

Ala Trp Gly Gln Gly Thr Leu Val Thr Val Ser Ser Gly Gly Gly Gly
        115                 120                 125

Ser Gln Val Gln Leu Gln Glu Ser Gly Gly Gly Leu Val Gln Pro Gly
    130                 135                 140

Gly Ser Leu Arg Leu Ser Cys Ala Ala Ser Gly Tyr Ser Arg Thr Ser
145                 150                 155                 160

Arg Trp Met Ala Trp Phe Arg Gln Ala Pro Gly Lys Gly Leu Glu Gly
                165                 170                 175

Val Ala Ala Ile Tyr Thr Gly Gly Ser Ser Thr Leu Tyr Ala Asp Ser
            180                 185                 190

Val Lys Gly Arg Phe Thr Ile Ser Arg Asp Asn Ala Lys Asn Ser Val
        195                 200                 205

Tyr Leu Gln Met Asn Ser Leu Arg Ala Glu Asp Thr Ala Val Tyr Tyr
    210                 215                 220

Cys Ala Ala Asp Lys Leu Ala Gly Asp Phe Trp Leu Val Asp Arg Trp
225                 230                 235                 240

Arg Ala Trp Gly Gln Gly Thr Leu Val Thr Val Ser Ser Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335
```

Ser Val Leu Thr Val Leu His Gln Asp Trp Leu Asn Gly Lys Glu Tyr
                340                 345                 350

Lys Cys Lys Val Ser Asn Lys Ala Leu Pro Ala Pro Ile Glu Lys Thr
            355                 360                 365

Ile Ser Lys Ala Lys Gly Gln Pro Arg Glu Pro Gln Val Tyr Thr Leu
370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
                420                 425                 430

Ser Asp Gly Ser Phe Phe Leu Tyr Ser Lys Leu Thr Val Asp Lys Ser
            435                 440                 445

Arg Trp Gln Gln Gly Asn Val Phe Ser Cys Ser Val Met His Glu Ala
        450                 455                 460

Leu His Asn His Tyr Thr Gln Lys Ser Leu Ser Leu Ser Pro Gly Lys
465                 470                 475                 480

<210> SEQ ID NO 120
<211> LENGTH: 475
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Ser Arg Thr Ser Arg
            20                  25                  30

Trp Met Ala Trp Phe Arg Gln Ala Pro Gly Lys Gly Leu Glu Gly Val
        35                  40                  45

Ala Ala Ile Tyr Thr Gly Gly Ser Ser Thr Leu Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Ala Asp Lys Leu Ala Gly Asp Phe Trp Leu Val Asp Arg Trp Arg
            100                 105                 110

Ala Trp Gly Gln Gly Thr Leu Val Thr Val Ser Ser Gln Val Gln Leu
        115                 120                 125

Gln Glu Ser Gly Gly Gly Leu Val Gln Pro Gly Gly Ser Leu Arg Leu
    130                 135                 140

Ser Cys Ala Ala Ser Gly Tyr Ser Arg Thr Ser Arg Trp Met Ala Trp
145                 150                 155                 160

Phe Arg Gln Ala Pro Gly Lys Gly Leu Glu Gly Val Ala Ala Ile Tyr
                165                 170                 175

Thr Gly Gly Ser Ser Thr Leu Tyr Ala Asp Ser Val Lys Gly Arg Phe
            180                 185                 190

Thr Ile Ser Arg Asp Asn Ala Lys Asn Ser Val Tyr Leu Gln Met Asn
        195                 200                 205

Ser Leu Arg Ala Glu Asp Thr Ala Val Tyr Tyr Cys Ala Ala Asp Lys

Leu Ala Gly Asp Phe Trp Leu Val Asp Arg Trp Arg Ala Trp Gly Gln
225                 230                 235                 240

Gly Thr Leu Val Thr Val Ser Ser Asp Lys Thr His Thr Cys Pro Pro
            245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys
465                 470                 475

<210> SEQ ID NO 121
<211> LENGTH: 227
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Gly Gly Gly Ser
1               5

<210> SEQ ID NO 123
<211> LENGTH: 136
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
        35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu
    130                 135
```

```
<210> SEQ ID NO 124
<211> LENGTH: 116
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Gly Ser Ser
            20                  25                  30

His Met Ser Trp Phe Arg Ala Pro Gly Lys Gly Leu Glu Trp Val
        35                  40                  45

Ser Thr Ile His Ser Gly Gly Phe Gly Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Leu Ala Thr Asp Trp Arg Lys Pro Trp Gly Gln Gly Thr Leu Val
            100                 105                 110

Thr Val Ser Ser
        115

<210> SEQ ID NO 125
<211> LENGTH: 124
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Val Gln Leu Gln Glu Ser Gly Gly Gly Leu Val Gln Pro Gly Gly
1               5                   10                  15

Ser Leu Arg Leu Ser Cys Ala Ala Ser Gly Tyr Ser Arg Thr Ser Arg
            20                  25                  30

Trp Met Ala Trp Phe Arg Gln Ala Pro Gly Lys Gly Leu Glu Gly Val
        35                  40                  45

Ala Ala Ile Tyr Thr Gly Gly Ser Ser Thr Leu Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Ala Asp Lys Leu Ala Gly Asp Phe Trp Leu Val Asp Arg Trp Arg
            100                 105                 110

Ala Trp Gly Gln Gly Thr Leu Val Thr Val Ser Ser
        115                 120

<210> SEQ ID NO 126
<211> LENGTH: 684
<212> TYPE: DNA
<213> ORGANISM: Artificial Sequence
<220> FEATURE:
<223> OTHER INFORMATION: Description of Artificial Sequence: Synthetic
      nucleic acid
```

```
<400> SEQUENCE: 126
gacaaaaccc acacctgtcc cccttgtcct gctcccgagc tcctgggagg accttccgtg      60
ttcctcttcc ctcccaaacc caaggacacc ctgatgatta gcaggacacc cgaggtgacc     120
tgtgtggtgg tggatgtgag ccatgaggac cccgaggtga agtttaactg gtacgtggac     180
ggcgtcgagg tgcacaacgc taagaccaaa cccagggagg agcagtacaa ctccacatac     240
cgggtcgtga gcgtgctgac cgtcctgcac caggattggc tgaatggcaa ggagtacaag     300
tgcaaggtga gcaacaaggc cctgcccgcc cccatcgaga agaccatcag caaggccaaa     360
ggacagcctc gggagcccca ggtttatact ctccccccca gccgggacga actgaccaag     420
aatcaggtgt ccctcacctg cctcgtgaag ggctttttacc ccagcgacat tgccgtggag     480
tgggagagca atggacagcc cgaaaacaac tacaagacca cccccccgt cctggactcc      540 gatggcagct tcttcctgta cagcaagctg accgtggaca gagcaggtg gcagcagggc     600 aacgtgttta gctgcagcgt catgcacgag gctctccaca accactacac ccagaagtcc     660
ctgagcctga gccccggaaa gtga                                            684

<210> SEQ ID NO 127
<211> LENGTH: 142
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
        35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu His His His His His
    130                 135                 140
```